United States Patent
Oniciu et al.

(10) Patent No.: US 12,312,308 B2
(45) Date of Patent: May 27, 2025

(54) SALTS AND ESTERS OF APX3330 AND THERAPEUTIC USES THEREOF

(71) Applicant: Opus Genetics, Inc., Farmington Hills, MI (US)

(72) Inventors: Daniela Carmen Oniciu, Gainesville, FL (US); Corina-Mihaela Manta, Bucharest (RO); Anthony Carestia, Greensboro, NC (US); Jon Housley, Summerfield, NC (US)

(73) Assignee: Opus Genetics, Inc., Farmington Hills, MI (US)

( * ) Notice: Subject to any disclaimer, the term of this patent is extended or adjusted under 35 U.S.C. 154(b) by 0 days.

(21) Appl. No.: 18/590,387

(22) Filed: Feb. 28, 2024

(65) Prior Publication Data

US 2024/0199523 A1    Jun. 20, 2024

Related U.S. Application Data

(63) Continuation of application No. 18/367,631, filed on Sep. 13, 2023.

(60) Provisional application No. 63/375,647, filed on Sep. 14, 2022.

(51) Int. Cl.
  C07C 57/42    (2006.01)
  C07C 69/88    (2006.01)

(52) U.S. Cl.
  CPC .............. *C07C 57/42* (2013.01); *C07C 69/88* (2013.01); *C07B 2200/13* (2013.01)

(58) Field of Classification Search
  CPC .......................... C07C 57/42; C07B 2200/13
  See application file for complete search history.

(56) References Cited

U.S. PATENT DOCUMENTS

| | | |
|---|---|---|
| 5,210,239 A | 5/1993 | Abe et al. |
| 5,385,942 A | 1/1995 | Abe et al. |
| 9,040,505 B2 | 5/2015 | Kelley |
| 9,089,605 B2 | 7/2015 | Kelley et al. |
| 9,193,700 B2 | 11/2015 | Kelley et al. |
| 9,877,936 B2 | 1/2018 | Kelley et al. |
| 10,058,523 B2 | 8/2018 | Kelley |
| 10,154,973 B2 | 12/2018 | Kelley et al. |
| 11,160,770 B2 | 11/2021 | Kelley et al. |
| 11,331,294 B2 | 5/2022 | Kelley |
| 11,351,130 B2 | 6/2022 | Kelley et al. |
| 11,566,005 B2 | 1/2023 | Oniciu |
| 11,648,226 B2 | 5/2023 | Kelley et al. |
| 11,723,886 B2 | 8/2023 | Kelley et al. |
| 2010/0285008 A1 | 11/2010 | Kelley |
| 2010/0297113 A1 | 11/2010 | Kelley et al. |
| 2014/0094464 A1 | 4/2014 | Kelley et al. |
| 2014/0128398 A1 | 5/2014 | Kelley et al. |
| 2015/0265564 A1 | 9/2015 | Kelley |
| 2016/0045461 A1 | 2/2016 | Kelley et al. |
| 2016/0166521 A1 | 6/2016 | Kelley et al. |
| 2017/0304222 A1 | 10/2017 | Kelley et al. |
| 2018/0133175 A1 | 5/2018 | Kelley et al. |
| 2018/0325853 A1 | 11/2018 | Kelley |
| 2019/0117602 A1 | 4/2019 | Kelley et al. |
| 2019/0160034 A1 | 5/2019 | Kelley et al. |
| 2019/0231728 A1 | 8/2019 | Kelley |
| 2019/0274988 A1 | 9/2019 | Kelley |
| 2019/0365671 A1 | 12/2019 | Kelley et al. |
| 2020/0215001 A1 | 7/2020 | Kelley et al. |
| 2020/0253904 A1 | 8/2020 | Kelley et al. |
| 2021/0038553 A1 | 2/2021 | Kelley et al. |
| 2021/0393556 A1 | 12/2021 | Kelley et al. |
| 2022/0062205 A1 | 3/2022 | Kelley et al. |
| 2022/0184016 A1 | 6/2022 | Kelley |
| 2022/0249421 A1 | 8/2022 | Kelley |
| 2022/0388965 A1 | 12/2022 | Oniciu |
| 2023/0146674 A1 | 5/2023 | Oniciu |
| 2023/0293471 A1 | 9/2023 | Kelley et al. |
| 2023/0330046 A1 | 10/2023 | Kelley et al. |
| 2024/0101505 A1 | 3/2024 | Oniciu et al. |

FOREIGN PATENT DOCUMENTS

| | | | |
|---|---|---|---|
| WO | WO-2009042542 A1 | 4/2009 | |
| WO | WO-2009042544 A1 | 4/2009 | |
| WO | WO-2012162589 A1 | 11/2012 | |

(Continued)

OTHER PUBLICATIONS

Akhtar M et al., "Survivin: role in diagnosis, prognosis, and treatment of bladder cancer", Adv Anat Pathol., 2006, 13(3):122-126.
Antoni S et al., "Bladder cancer incidence and mortality: a global overview and recent trends" Eur Urol 2017,71(1):96-108.
Bapat A, et al., "Going Ape as an approach to cancer therapeutics", Antioxid Redox Signal, 2009, 11(3):651-667.
Bardia A, et al., "Functional polymorphisms in XRCC-1 and APE-1 contribute to increased apoptosis and risk of ulcerative colitis" Inflamm Res, 2012, 61(4):359-365.
Bates D O, et al., "Vascular endothelial growth factors and vascular permeability" Cardiovasc Res. 2010, 87(2): 262-271.

(Continued)

*Primary Examiner* — Marcos L Sznaidman
(74) *Attorney, Agent, or Firm* — Dechert LLP

(57) ABSTRACT

This invention relates to Compound 1 (APX3330) salts and esters. The invention also provides compositions comprising a Compound 1 salt or ester. The invention also provides compounds of formula (I) and formula (II) and pharmaceutically acceptable salts thereof. The invention further provides compositions comprising a compound of formula (I) or formula (II), or a pharmaceutically acceptable salt thereof; and a pharmaceutically acceptable carrier or vehicle. The invention also provides methods for treating or preventing a disease, such as cancer, a liver disorder, an ocular disorder, a cardiovascular disorder, fibrosis, or an inflammatory disorder, comprising administering to a subject in need thereof an effective amount of a Compound 1 salt or ester; or compound of formula (I) or formula (II), or pharmaceutically acceptable salt thereof.

27 Claims, 16 Drawing Sheets

(56) References Cited

FOREIGN PATENT DOCUMENTS

| | | |
|---|---|---|
| WO | WO-2012167122 A1 | 12/2012 |
| WO | WO-2018175429 A1 | 9/2018 |
| WO | WO-2018194976 A1 | 10/2018 |
| WO | WO-2019157163 A1 | 8/2019 |
| WO | WO-2022232597 A1 | 11/2022 |
| WO | WO-2022245964 A1 | 11/2022 |
| WO | WO-2023147297 A2 | 8/2023 |
| WO | WO-2024059664 A2 | 3/2024 |

OTHER PUBLICATIONS

Bhakat KK, et al., "Transcriptional regulatory functions of mammalian AP-endonuclease (APE1/Ref-1), an essential multifunctional protein" Antioxid Redox Signal, 2009, 11(3):621-637.

Biankin AV, et al., "Pancreatic cancer genomes reveal aberrations in axon guidance pathway genes" Nature, 2012, 491(7424):399-405.

Biswas A, et al., "Endothelial cell tumor growth is Ape/ref-1 dependent" Am J Physiol Cell Physiol, 2015, 309(5): C296-C307.

Bobola MS et al., "Apurinic/apyrimidinic endonuclease activity is associated with response to radiation and chemotherapy in medulloblastoma and primitive neuroectodermal tumors" Clin Cancer Res, 2005, 11(20):7405-7414.

Bobola MS, et al., "Apurinic/apyrimidinic endonuclease activity is elevated in human adult gliomas" Clin Cancer Res, 2001, 7(11):3510-3518.

Boyer et al. "The safety of APX3330, an oral drug candidate for the treatment of diabetic eye disease, in the ongoing masked 24-week ZETA-1 Phase 2 clinical trial", Investigative Ophthalmology & Visual Science Jun. 2022, vol. 63, 675-F0129, 2 pages.

Bria E, et al., "Gemcitabine-based combinations for inoperable pancreatic cancer: have we made real progress?" A meta-analysis of 20 phase 3 trials, 2007, Cancer 110(3):525-533.

Brown JM, et al., "Exploiting tumour hypoxia in cancer treatment" Nat Rev Cancer, 2004, 4(6):437-447.

Brown JM. et al., "Tumor hypoxia, drug resistance, and metastases" J Natl Cancer Inst, 1990, 82(5):338-339.

Buisine MP et al., "Mucin gene expression in intestinal epithelial cells in Crohn's disease" Gut, 2001, 49(4):544-551.

Cardoso AA, et al., "APE1/Ref-1 regulates STAT3 transcriptional activity and APE1/Ref-1-STAT3 dual-targeting effectively Inhibits pancreatic cancer cell survival" PLoS One, 2012, 7(10):e47462, 13 pages.

Chandra M, et al., "Incidence, histopathologic and electron microscopic features of spontaneous nephroblastomas in rats" Toxicol Lett, 1992, 62:179-190.

Chandrasekharan B, et al., "Colonic motor dysfunction in human diabetes is associated with enteric neuronal loss and increased oxidative stress" Neurogastroenterol Motil, 2011, 23(2):131-138.

Chang Q et al., "Hypoxia predicts aggressive growth and spontaneous metastasis formation from orthotopically grown primary xenografts of human pancreatic cancer" Cancer Res, 2011, 71(8):3110-3120.

Chen D, et al., "Detection of survivin expression in bladder cancer and renal cell carcinoma using specific monoclonal antibodies" Oncol Rep, 2018, 39(6):2817-2828.

Chen Y, et al., "Photoreceptor degeneration and retinal inflammation induced by very low-density lipoprotein receptor deficiency" Microvasc Res, 2009, 78(1):119-127.

Chiarini LB, et al., "Evidence that the bifunctional redox factor/AP endonuclease Ref-1 is an anti-apoptotic protein associated with differentiation in the developing retina" Cell Death Differ, 2000, 7(3):272-281.

Choi S, et al, "Urinary APE1/Ref-1: a potential bladder cancer biomarker" Dis Markers, 2016: 7276502, 8 pages.

Cummins EP, et al., "Hypoxia-responsive transcription factors" Pflugers Arch, 2005, 450(6):363-371.

Day S, et al., "Ocular complications after anti-vascular endothelial growth factor therapy in Medicare patients with age-related macular degeneration" Am. J. Ophthalmol, 2011, 152 (2):266-272.

Demple B, et al., "Cloning and expression of APE, the cDNA encoding the major human apurinic endonuclease; definition of a family of DNA repair enzymes" Proc Natl Acad Sci USA, 1991, 88(24):11450-11454.

D'Haens G, et al., "Risks and benefits of biologic therapy for inflammatory bowel diseases" Gut, 2007; 56(5):725-732.

Dhir R, et al., "Stat3 activation in prostatic carcinomas" Prostate, 2002, 51(4):241-246.

Di Maso V. al., "Transcriptional up-regulation of APE1/Ref-1 in hepatic tumor: role in hepatocytes resistance to oxidative stress and apoptosis" PLoS One, 2015, 10(12):e0143289, 14 pages.

Don-Doncow N, et al., "Expression of STAT3 in Prostate Car tastases" Eur Urol, 2017, 71(3):313-316.

Dorrell MI, et al., "Antioxidant or neurotrophic factor treatment preserves function in a mouse model of neovascularization-associated oxidative stress" J Clin Invest, 2009, 119(3):611-623.

Edelman JL, et al., "Corticosteroids inhibit VEGF-induced vascular leakage in a rabbit model of blood-retinal and blood-aqueous barrier breakdown" Exp Eye, 2005, Res 80(2):249-258.

Eri RD, et al., "An intestinal epithelial defect conferring ER stress results in inflammation involving both innate and adaptive immunity" Mucosal Immunol, 2010, 4:354-364.

Erkan M, et al., "Tumor microenvironment and progression of pancreatic cancer" Exp Oncol, 2010, 32(3):128-131.

Evans AR, et al., "Going APE over ref-1" Mutat Res, 2002, 461(2):83-108.

Falavarjani KG, et al., "Adverse events and complications associated with intravitreal injection of anti-VEGF agents: a review of literature" Eye (Lond), 2013, 27(7):787-794.

Fehrenbacher JC, et al., "DNA damage mediates changes in neuronal sensitivity induced by the inflammatory mediators, MCP-1 and LPS, and can be reversed by enhancing the DNA repair function of APE1" Neuroscience, 2017, 366:23-35.

Ferrante M, et al., "The value of myenteric plexitis to predict early postoperative Crohn's disease recurrence" Gastroenterol, 2006, 130(6):1595-1606.

Fishel ML, et al., "Apurinic/apyrimidinic endonuclease/redox factor-1 (APE1/Ref-1) redox function negatively regulates NRF2" J Biol Chem, 2014, 290(5):3057-3068.

Fishel ML, et al., "Development of STAT3 dual-targeting strategies for the treatment of pancreatic cancer" In: Proceedings of the 107th Annual Meeting of the American Association for Cancer Research, New Orleans, LA, 2016, Abstract 1246, 2 pages.

Fishel ML, et al., "Impact of APE1/Ref-1 redox inhibition on pancreatic tumor growth" Mol Cancer Ther, 2011, 10(9);1698-1708.

Fishel ML, et al., "Inhibition of the redox function of APE1/Ref-1 in myeloid leukemia cell lines results in a hypersensitive response to retinoic acid-induced differentiation and apoptosis" Exp Hematol, 2010, 38(12):1178-1188.

Fishel ML, et al., "Knockdown of the DNA repair and redox signaling protein Ape1/Ref-1 blocks ovarian cancer cell and tumor growth" DNA Repair (Amst), 2008, 7(2):177-186.

Fishel ML, et al., "Manipulation of base excision repair to sensitize ovarian cancer cells to alkylating agent temozolomide" Clin Cancer Res, 2007, 13(1):260-267.

Fishel ML, et al., "Targeting APE1/Ref-1 pathway inhibition in pancreatic cancer using APX3330 for clinical trials" In: Proceedings of the 107th Annual Meeting of the American Association for Cancer Research. New Orleans, LA., 2016, Abstract 4740, 2 pages.

Fishel ML, et al., "The DNA base excision repair protein Ape1/Ref-1 as a therapeutic and chemopreventive target" Mol Aspects Med, 2007, 28(3-4): 375-395.

Folkman J, et al., "Angiogenesis inhibition and tumor regression caused by heparin or a heparin fragment in the presence of cortisone" Science, 1983, 221(4612):719-725.

Frese KK, et al., "nab-Paclitaxel potentiates gemcitabine activity by reducing cytidine deaminase levels in a mouse model of pancreatic cancer" Cancer Discov, 2012, 2(3):260-269.

Garcea G, et al., "Hypoxia and angiogenesis in pancreatic cancer" ANZ J Surg, 2006, 76(9):830-842.

(56) References Cited

OTHER PUBLICATIONS

Georgiadis MM, et al., "Evolution of the redox function in mammalian apurinic/apyrimidinic endonuclease" Mutat Res, 2008, 643(1-2):54-63.
Gilmore TD, et al., "Inhibitors of NF-κB signaling: 785 and counting" Oncogene, 2006, 25(51):6887-6899.
Gleichenhagen J, et al., "Evaluation of a new survivin ELISA and UBC® rapid for the detection of bladder cancer in urine" Int J Mol Sci, 2018, 19(1):226, 13 pages.
Gonzalez V. et al., "25-LB: Oral APX3330 Reduces the DRSS Worsening after 24-weeks of Daily Treatment—Efficacy and Safety Results of the ZETA-1 Phase 2 Trial in Diabetic Retinopathy", Diabetes Jun. 2023, vol. 72(Supplement 1):25-LB, 3 pages.
Gonzalez-Villasana V, et al., "Bisphosphonates inhibit stellate cell activity and enhance antitumor effects of nanoparticle albumin-bound paclitaxel in pancreatic ductal adenocarcinoma" Mol Cancer Ther, 2014, 13(11):2583-2594.
Grossniklaus HE, et al., "Animal models of choroidal and retinal neovascularization" Prog Retin Eye Res, 2010, 29(6):500-519.
Guan G, et al., "Implications of antioxidant systems in inflammatory bowel disease" Biomed Res Int, 2018 : 1290179, 7 pages.
Guerreiro PS, et al., "The APE1 redox inhibitor E3330 reduces collective cell migration of human breast cancer cells and decreases chemoinvasion and colony formation when combined with docetaxel" Chem Biol Drug Des, 2017, 90(4): 561-57.
Haines JL, et al., "Functional candidate genes in age-related macular degeneration: significant association with VEGF, VLDLR, and LRP6" Invest Ophthalmol Vis Sci, 2006, 47(1):329-335.
Harrison L, et al., "Can DNA repair cause enhanced cell killing following treatment with ionizing radiation?" Pathophysiology, 2002, 8(3):149-159.
Heazlewood CK, et al., "Aberrant Mucin Assembly in Mice Causes Endoplasmic Reticulum Stress and Spontaneous Inflammation Resembling Ulcerative Colitis" PLOS Med, 2008, 5(3):e54, 21 pages.
Heckenlively JR, et al., "Mouse model of subretinal neovascularization with choroidal anastomosis" Retina, 2003, 23(4):518-522.
Hershman DL, et al., "Prevention and management of chemotherapy-induced peripheral neuropathy in survivors of adult cancers: American Society of Clinical Oncology clinical practice guideline" J Clin Oncol, 2014, 32(18):1941-1967.
Hiramoto M, et al., "Nuclear targeted suppression of NF-κB activity by the novel quinone derivative E3330" Journal of Immunology, 1998, 160(2): 810-819.
Hofseth LJ, et al., "The adaptive imbalance in base excision-repair enzymes generates microsatellite instability in chronic inflammation" J Clin Invest, 2003, 112(12):1887-1894.
Hu W, et al., "Expression of VLDLR in the retina and evolution of subretinal neovascularization in the knockout mouse model's retinal angiomatous proliferation" Invest Ophthalmol Vis Sci, 2008, 49(1): 407-415.
Huang LE, et al., "Activation of hypoxia-inducible transcription factor depends primarily upon redox-sensitive stabilization of its alpha subunit" J Biol Chem, 1996, 271(50):32253-32259.
Invitation to pay additional fees for International Application No. PCT/US2023/074113, dated Nov. 17, 2023, 3 pages.
Jedinak A, et al., "Apurinic/apyrimidinic endonuclease 1 regulates inflammatory response in macrophages" Anticancer Res, 2011, 31(2):379-385.
Jiang A, et al., "Inhibition of APE1/Ref-1 Redox activity with APX3330 blocks retinal angiogenesis in vitro and in vivo" Vision Res, 2011, 51(1):93-100.
Jiang S, et al., "Ape1 regulates WNT/beta-catenin signaling through its redox functional domain in pancreatic cancer cells" Int J Oncol, 2015, 47(2):610-620.
Jiang Y, et al., "Implications of apurinic/apyrimidinic endonuclease in reactive oxygen signaling response after cisplatin treatment of dorsal root ganglion neurons" Cancer Res, 2008, 68(15):6425-6434.
Jiang Y, et al., "Reduced expression of DNA repair and redox signaling protein APE1/Ref-1 impairs human pancreatic cancer cell survival, proliferation, and cell cycle progression" Cancer Invest, 2010, 28(9):885-895.
Jiang Y, Get al., "Role of APE1 in differentiated neuroblastoma SH-SY5Y cells in response to oxidative stress: use of APE1 small molecule inhibitors to delineate APE1 functions" DNA Repair (Amst), 2009, 8(11):1273-1282.
Jones S, et al., "Core signaling pathways in human pancreatic cancers revealed by global genomic analyses" Science, 2008, 321(5897):1801-1806.
Kakolyris S, et al., "Human AP endonuclease 1 (HAP1) protein expression in breast cancer correlates with lymph node status and angiogenesis" Br J Cancer, 1998, 77(7):1169-1173.
Kakolyris S, et al., "Human apurinic endonuclease 1 expression in a colorectal adenoma-carcinoma sequence" Cancer Res, 1997, 57(9): 1794-1797.
Kang BH, et al., "Combinatorial drug design targeting multiple cancer signaling networks controlled by mitochondrial Hsp90" J Clin Invest. 2009, 119(3):454-464.
Keleg S, et al., "Adrenomedullin is induced by hypoxia and enhances pancreatic cancer cell invasion" Int J Cancer, 2007, 121(1):21-32.
Kelley MR, et al., "APE1/Ref-1 role in redox signaling; translational applications of targeting the redox function of the DNA repair/redox protein APE1/Ref-1" Curr Mol Pharmacol, 2012, 5(1):36-53.
Kelley MR, et al., "DNA repair and redox signaling. In: Bagley RG, editor" The tumor microenvironment, New York: Human Press, 2010, p. 133-168.
Kelley MR, et al., "Elevated and altered expression of the multifunctional DNA base excision repair and redox enzyme Ape1/ref-1 in prostate cancer" Clin Cancer Res, 2001, 7(4):824-830.
Kelley MR, et al., et al., "Role of the DNA base excision repair protein, APE1 in cisplatin, oxaliplatin, or carboplatin induced sensory neuropathy" PLoS One, 2014, 9(9):e106485, 15 pages.
Kelley MR, et al., "FDNA repair proteins as molecular targets for cancer therapeutics" Anticaricer Agents Med Chem, 2008, 8(4):417-425.
Kelley MR, et al., "Functional analysis of new and novel analogs of E3330 that block the redox signaling activity of the multifunctional AP endonuclease/redox signaling enzyme APE1/Ref-1" Antioxid Redox Signal, 2011, 14(8):1387-1401.
Kelley MR, et al., "Targeting DNA repair pathways for cancer treatment: what's new?" Future Oncol, 2014, 10(7):1215-1237.
Kim SY, et al., "Recent advances in developing inhibitors for hypoxia-inducible factor prolyl hydroxylases and their therapeutic implications" Molecules, 2015, 20(11):20551-20568.
Klein R. "Overview of progress in the epidemiology of age-related macular degeneration" Ophthalmic Epidemiol, 2007, 14(4):184-187.
Koike, H. et al., "Gene expression of survivin and its spliced isoforms associated with proliferation and aggressive phenotypes of prostate cancer." Urology, 2008, 72(6):1229-1233.
Koong AC, et al., "Pancreatic tumors show high levels of hypoxia" Int J Radiat Oncol Biol Phys, 2000, 48(4):919-922.
Koukourakis MI, et al., "Nuclear expression of human apurinic/apyrimidinic endonuclease (HAP1/Ref-1) in head-and-neck cancer is associated with resistance to chemoradiotherapy and poor outcome" Int J Radiat Oncol Biol Phys, 2001, 50(1):27-36.
Lando D, et al., "A redox mechanism controls differential DNA binding activities of hypoxia-inducible factor (HIF) 1alpha and the HIF-like factor" J Biol Chem, 2000, 275(7):4618-4627.
Lau JP, et al., "Effects of gemcitabine on APE/ref-1 endonuclease activity in pancreatic cancer cells, and the therapeutic potential of antisense oligonucleotides" Br J Cancer, 2004, 91(6):1166-1173.
Lee R, et al., "Epidemiology of diabetic retinopathy, diabetic macular edema and related vision loss" Eye Vis, 2015, 2:17, 25 pages.
Li C, et al., "Biochemical alterations in the retinas of very low-density lipoprotein receptor knockout mice: an animal model of retinal angiomatous proliferation" Arch Ophthalmol, 2007, 125(6):795-803.

(56) References Cited

OTHER PUBLICATIONS

Li L, et al., "Modulation of gene expression and tumor cell growth by redox modification of STAT3" Cancer Res, 2010, 70(20):8222-8232.

Li Y., et al., "Inhibition of APE1/Ref-1 redox activity rescues human retinal pigment epithelial cells from oxidative stress and reduces choroidal neovascularization," Redox Biol, 2014, vol. 2, pp. 485-494.

Li Y., et al., "Suppression of choroidal neovascularization through inhibition of APE1/Ref-1 redox & activity," Invest Ophthalmol Vis Sci, 2014, vol. 55, No. 7, pp. 4461-4469.

Liu X, et al., "Correlation analysis of JAK-STAT pathway components on prognosis of patients with prostate cancer" Pathol Oncol Res, 2012, 18(1):17-23.

Logsdon D.P., et al., "Regulation of HIF1α under hypoxia by APE1/Ref-1 impacts CA9 expression: dual targeting in patient-derived 3D pancreatic cancer models," Mol Cancer Ther, 2016, vol. 15 No. 11, pp. 2722-2732.

Longobardi T et al., "Work losses related to inflammatory bowel disease in the United States. Results from the National Health Interview Survey," Am J Gastroenterol, 2003, vol. 98, No. 5, pp. 1064-1072.

Lou D., et al., "Aberrant expression of redox protein Ape1 in colon cancer stem cells," Oncol Lett, 2014, vol. 7, No. 4, pp. 1078-1082.

Luo M., et al., "Characterization of the redox activity and disulfide bond formation in apurinic/apyrimidinic endonuclease," Biochemistry, 2012, vol. 51, No. 2, pp. 695-705.

Luo M., et al., "Redox regulation of DNA repair: implications for human health and cancer therapeutic development," Antioxid Redox Signal, 2010, vol. 12, No. 11, pp. 1247-1269.

Luo M., et al., "Role of the multifunctional DNA repair and redox signaling protein Ape1/Ref-1 in cancer and endothelial cells: small-molecule inhibition of the redox function of Ape1," Antioxid Redox Signal, 2008, vol. 10, No. 11, pp. 1853-1867.

Lux A., et al., "Non-responders to bevacizumab (Avastin) therapy of choroidal neovascular lesions," Br J Ophthalmol, 2007, vol. 91, No. 10, pp. 1318-1322.

Masoud G.N., et al., "HIF-1α pathway: role, regulation and intervention for cancer therapy," Acta Pharm Sin B, 2015, vol. 5, No. 5, pp. 378-389.

McElyea K., et al., "Efficacy study of APX3330, Ref-1 redox inhibitor, and gemcitabine in a mouse pancreatic ductal adenocarcinoma model," Proceedings of the 107th Annual Meeting; American Association for Cancer Research, New Orleans, LA. Abstract 5183, 2016, 2 pages.

McIlwain D.W., et al., "APE1/Ref-1 redox-specific inhibition decreases survivin protein levels and induces cell cycle arrest in prostate cancer cells," Oncotarget, 2018, vol. 9, No. 13, pp. 10962-10977.

McNeill D.R., et al., "A dominant-negative form of the major human abasic endonuclease enhances cellular sensitivity to laboratory and clinical DNA-damaging agents," Mol Cancer Res, 2007, vol. 5, No. 1, pp. 61-70.

McQuade R.M., et al., "Gastrointestinal dysfunction and enteric neurotoxicity following treatment with anticancer chemotherapeutic agent 5-fluorouracil," Neurogastroenterol Motil, 2016, vol. 28. No. 12, pp. 1861-1875.

McQuade R.M., et al., et al., "Role of oxidative stress in oxaliplatin-induced enteric neuropathy and colonic dysmotility in mice," B J Pharmacol, 2016, vol. 173, No. 24, pp. 3502-3521.

McQuade R.M., et al., "Irinotecan-induced gastrointestinal dysfunction is associated with enteric neuropathy, but increased numbers of cholinergic myenteric neurons," Front Physiol, 2017, vol. 8, No. 391, 18 pages.

Miyamoto K., et al., "Suppressive effects of E3330, a novel quinone derivative, on tumor necrosis factor-α generation from monocytes and macrophages," Agents Actions, 1992, vol. 37, No. 3-4, pp. 297-304.

Mora L.B., et al., "Constitutive activation of Stat3 in human prostate tumors and cell lines: direct inhibition of Stat3 signaling induces apoptosis of prostate cancer cells," Cancer Res, 2002, vol. 62, No. 22, pp. 6659-6666.

Nagathihalli N.S., et al., "Signal transducer and activator of transcription 3, mediated remodeling of the tumor microenvironment results in enhanced tumor drug delivery in a mouse model of pancreatic cancer," Gastroenterology, 2015, vol. 149, No. 7, pp. 1932-1943.

NCT03375086 ClinicalTrials.gov, "A Study of APX3330 in Patients with Advanced Solid tumors (APX3330)", Apexian Paharmaceuticals, Inc., Sep. 7, 2020, 9 pages.

NCT04692688 ClinicalTrials.gov, "Study of the Safety and Efficacy of APX3330 in diabetic Retinopathy (ZETA-1)", Ocuphire Pharma, Inc., Feb. 27, 2023, 11 pages.

Ni Z et al., "Inhibition of constitutively activated Stat3 signaling pathway suppresses growth of prostate cancer cells," Cancer Res, 2000, vol. 60, No. 5, pp. 1225-1228.

Nishi T., et al., "Spatial redox regulation of a critical cysteine residue of NF-kappa B in vivo," J. Biol Chem, 2002, vol. 277, No. 46 pp. 44548-44556.

[No Author] "Ocuphire Pharma Announces In-License of Phase 2 Oral Small Molecule Drug Candidate for Diabetic Retinopathy and Diabetic Macular Edema from Apexian Pharmaceuticals", Ocuphire Pharma Press Release, Jan. 22, 2020, 4 pages.

Noike T., et al., "Increased expression of thioredoxin-1, vascular endothelial growth factor, and redox factor-1 is associated with poor prognosis in patients with liver metastasis from colorectal cancer," Hum Pathol, 2008, vol. 39, No. 2, pp. 201-208.

Nyland R.L., et al., "Design and synthesis of novel quinone inhibitors targeted to the redox function of apurinic/apyrimidinic endonuclease 1/Redox enhancing factor-1 (Ape1/Ref-1)," J Med Chem, 2010, vol. 53, No. 3, pp. 1200-1210.

Philip P.A., et al., "Consensus report of the national cancer institute clinical trials planning meeting on pancreas cancer treatment," J Clin Oncol, 2009, vol. 27, No. 33, pp. 5660-5669.

Prasad P.S., et al., "Age-related macular degeneration: current and novel therapies," Maturitas, 2010, vol. 66, No. 1, pp. 46-50.

Pubchem CID 6439397, "(2E)-2-[(4, 5-dimethoxy-2-methyl-3,6-dioxocyclohexa-1,4-dien-1-yl)methylidene]undecanoic acid," National Library of Medicine, 2006, 31 pages.

Puglisi F., et al., "Prognostic role of Ape/Ref-1 subcellular expression in stage I-III breast carcinomas," Oncol Rep, 2002, vol. 9, No. 1, pp. 11-17.

Puglisi F., et al., "Prognostic significance of Ape1/Ref-1 subcellular localization in non-small cell lung carcinomas," Anticancer Res, 2001, vol. 21, No. 6A, pp. 4041-4049.

Qing Y., et al., "Upregulation of PD-L1 and APE1 is associated with tumorigenesis and poor prognosis of gastric cancer," Drug Des Devel Ther, 2015, vol. 9 pp. 901-909.

Rahman A.A., et al., "Alterations in the distal colon innervation in Winnie mouse model of spontaneous chronic colitis," Cell Tissue Res, 2015, vol. 362, No. 3, pp. 497-512.

Robertson K.A., et al., Altered expression of Ape1/Ref-1 in germ cell tumors and overexpression in NT2 cells confers resistance to bleomycin and radiation, Cancer Res, 2001, vol. 61, No. 5, pp. 2220-2225.

Robinson A.M., et al., "Fecal microbiota and metabolome in a mouse model of spontaneous chronic colitis: relevance to human inflammatory bowel disease," Inflamm Bowel Dis, 2016, vol. 22, No. 12, pp. 2767-2787.

Rouanne M.M., et al., "Development of immunotherapy in bladder cancer: present and future on targeting PD(L)1 and CTLA-4 pathways," World J Urol, 2018, vol. 36, No. 11, pp. 1727-1740.

Rucki A.A., et al., "Heterogeneous stromal signaling within the tumor microenvironment controls the metastasis of pancreatic cancer," Cancer Res, 2017, vol. 77, No. 1, pp. 41-52.

Sardar Pasha SPB., et al., "Ref-1/APE1 inhibition with novel small molecules blocks ocular neovascularization," J Pharmacol Exp Ther, 2018, vol. 367, No. 1, pp. 108-118.

Sempere L.F., et al., "A novel 3-dimensional culture system uncovers growth stimulatory actions by TGFbeta in pancreatic cancer cells," Cancer Biol Ther, 2011, vol. 12, No. 3, pp. 198-207.

(56) References Cited

OTHER PUBLICATIONS

Seo Kelley M.R., et al., "Selenomethionine regulation of p53 by a ref1-dependent redox mechanism," Proc Natl Acad Sci USA, 2002, vol. 99, No. 22, pp. 14548-14553.

Shah F., et al., et al., "Exploiting the Ref-1-APE1 node in cancer signaling and other diseases: from bench to clinic," NPJ Precis Oncol, 2017, vol. 1, pp. 1-19.

Shannon H.E., et al., "Longitudinal bioluminescence imaging of primary versus abdominal metastatic tumor growth in orthotopic pancreatic tumor models in NSG mice," Pancreas, 2015, vol. 44, No. 1, pp. 64-75.

Sharbeen G. J., et al., "Exploiting base excision repair to improve therapeutic approaches for pancreatic cancer," Front Nutr, 2015, vol. 2:10, 11 pages.

Shariat S.F., et al., "Survivin expression is associated with features of biologically aggressive prostate carcinoma," Cancer, 2004, vol. 100, No. 4, pp. 751-757.

Shen J., et al., "Knockdown of survivin expression by siRNAs enhances chemosensitivity of prostate cancer cells and attenuates its tumorigenicity," Acta Biochim Biophys Sin (Shanghai), 2009, vol. 41, No. 3, pp. 223-230.

Shi Z., et al., "S-Phase arrest by nucleoside analogues and abrogation of survival without cell cycle progression by 7-hydroxystaurosporine," Cancer Res, 2001, vol. 61, No. 3, pp. 1065-1072.

Shimizu N., et al., "High-performance affinity beads for identify drug receptors," Nat Biotechnol, 2000, vol. 18, No. 8, pp. 877-881.

Shin J.H., et al., "APE1/Ref-1 as a serological biomarker for the detection of bladder cancer," Cancer Res Treat, 2015, vol. 47, No. 4, pp. 823-833.

Siegel R.L., et al., "Cancer statistics, 2016" CA Cancer J Clin, 2016, vol. 66, No. 1, pp. 7-30.

Siegel R.L., et al., "Cancer statistics, 2017," CA Cancer J Clin, 2017, vol. 67, No. 1, pp. 7-30.

Sokol Polin V., et al., "Plexitis as a predictive factor of early postoperative clinical recurrence In Crohn's disease," Gut, 2009, vol. 58, No. 9, pp. 1218-1225.

Su D., et al., "Interactions of APE1 with a redox inhibitor: Evidence for an alternate conformation of the enzyme," Biochemistry, 2011, vol. 50, No. 1, pp. 82-92.

Su X., et al., "Isolation and characterization of murine retinal endothelial cells," Mol Vis, 2003, vol. 9, pp. 171-178.

Tam L., et al., "Expression levels of the JAK/STAT pathway in the transition from hormone-sensitive to hormone-refractory prostate cancer," Br J Cancer, 2007, vol. 97, No. 3, pp. 378-383.

Tell G., et al., "The intracellular localization of APE 1/Ref-1: more than a passive phenomenon?" Antioxidants & Redox Signaling, 2005, vol. 7(3-4), pp. 367-384.

Tell G., et al., "The many functions of APE1/Ref-1: not only a DNA repair enzyme," Antioxid Redox Signal, 2009, vol. 11, No. 3, pp. 601-620.

Thomson B., et al., "Histology-specific expression of a DNA repair protein in pediatric rhabdomyosarcomas," Am J Pediatr Hematol Oncol, 2001, vol. 23, No. 4, pp. 234-239.

Tian T., et al., "Pathomechanisms of oxidative stress in inflammatory bowel disease and potential antioxidant therapies," Oxid Med Cell Longev, 2017:4535194, 18 pages.

Triantafillidis J.K., et al., "Current and emerging drugs for the treatment of inflammatory bowel disease" Drug Des Devel Ther, 2011, vol. 5, pp. 185-210.

Van Klinken B.J., et al., "Sulphation and secretion of the predominant secretory human colonic mucin MUC2 in ulcerative colitis," Gut, 1999, vol. 44, No. 3, pp. 387-393.

Vasko M., et al., "Enhancing the expression of the DNA repair/redox enzyme, Ape1/Ref-1, reduces neurotoxicity induced by ionizing radiation: Implications for decreasing neurocognitive dysfunction.," Pediatric Academic Societies' Annual Meeting Toronto, Canada (Abstract), 2006, p. 491 (1 page).

Vasko M.R., et al., "The multifunctional DNA repair/redox enzyme Ape1/Ref-1 promotes survival of neurons after oxidative stress," DNA Repair (Amst), 2005, vol. 4, No. 3, pp. 367-379.

Vasko M.R., et al., "The repair function of the multifunctional DNA repair/redox protein APE1 is neuroprotective after ionizing radiation," DNA Repair (Amst), 2011, vol. 10, pp. 942-962.

Wafai L., et al., "Effects of oxaliplatin on mouse myenteric neurons and colonic motility," Front Neurosci, 2013, vol. 7:30, 8 pages.

Wang Y.T., et al., "APE1/Ref-1 prevents oxidative inactivation of ERK for G1-to-S progression following lead acetate exposure," Toxicology, 2013, vol. 305, pp. 120-129.

Whipple C., et al., "Targeting angiogenesis in pancreatic cancer: rationale and pitfalls," Langenbecks Arch Surg, 2008, vol. 393, No. 6, pp. 901-910.

Woods C.M., et al., "Taxol-induced mitotic block triggers rapid onset of a p53-independent apoptotic pathway," Mol Med, 1995, vol. 1, No. 5, pp. 506-526.

Wu P.F., et al., "Role of CXCL12/CXCR4 signaling axis in pancreatic cancer," Chin Med J (Eng), 2013, vol. 126, No. 17, pp. 3371-3374.

Xanthoudakis S., et al., "Identification and characterization of Ref-1, a nuclear protein that facilitates AP-1 DNA-binding activity," EMBO J, 1992, vol. 11, No. 2, pp. 653-665.

Xanthoudakis S., et al., "Redox activation of Fos-Jun DNA binding activity is mediated by a DNA repair enzyme," EMBO J, 1992, vol. 11, No. 9, pp. 3323-3335.

Xiang D.B., et al., "Chimeric adenoviral vector Ad5/F35-mediated APE1 siRNA enhances sensitivity of human colorectal cancer cells to radiotherapy in vitro and in vivo," Cancer Gene Ther, 2008, vol. 15, No. 10, pp. 625-635.

Xie K., et al., "Transcriptional anti-angiogenesis therapy of human pancreatic cancer," Cytokine Growth FR, 2008, vol. 17, No. 3, pp. 147-156.

Xu X., et al., "Combined use of urinary Survivin detection and liquid-based cytology for the early diagnosis of bladder urothelial carcinoma," Oncol Lett, 2018, vol. 15, No. 5, pp. 7739-7743.

Yang Z. Z., et al., "Experimental study enhancing the chemosensitivity of multiple myeloma to melphalan by using a tissue-specific APE1-silencing RNA expression vector," Clin Lymphoma Myeloma, 2007, vol. 7, No. 4296-304.

Yan T., et al., "APX3330 promotes neurorestorative effects after stroke in type one diabetic rats" Aging Dis. 2018, vol. 9, No. 3, pp. 453-466.

Yoshida T., et al., "Influence of cytidine deaminase on antitumor activity of 2'-deoxycytidine analogs in vitro and in vivo," Drug Metab Dispos, 2010, vol. 38, No. 10, pp. 1814-1819.

Zhang J., et al., "Inhibition of apurinic/apyrimidinic endonuclease 1's redox activity revisited," Biochemistry, 2013, vol. 52, No. 17, pp. 2955-2966.

Zou G.M., "Ape1 regulates hematopoietic differentiation of embryonic stem cells through its redox functional domain," Blood, 2007, vol. 109, No. 5, pp. 1917-1922.

Zou G.M., et al., "The Ape-1/Ref-1 redox antagonist E3330 inhibits the growth of tumor endothelium and endothelial progenitor cells: therapeutic implications in tumor angiogenesis," J Cell Physiol, 2009, vol. 219, No. 1, pp. 209-218.

Zou G.M., "Small-molecule inhibitor of the AP endonuclease 1/REF-1 E3330 inhibits pancreatic cancer cell growth and migration," Mol Cancer Ther, 2008, vol. 7, No. 7, pp. 2012-2021.

International Preliminary Report on Patentability for International Application No. PCT/US2022/027062, dated Oct. 24, 2023, 8 pages.

International Search Report and Written Opinion for International Application No. PCT/US2022/027062, dated Jul. 29, 2022, 10 pages.

Silva et al. "Bridging population pharmacokinetic and semimechanistic absorption modeling of APX3330," CPT Pharmacometrics & Systems Pharmacology, 2024, 13(1), pp. 106-117.

Co-Pending U.S. Appl. No. 18/288,435, inventor Mina Sooch et al., filed Oct. 26, 2023.

(56) References Cited

OTHER PUBLICATIONS

Hartman, et al., "Inhibition of APE1/Ref-1 for Neovascular Eye Diseases: From Biology to Therapy", Sep. 24, 2021 (Sep. 24, 2021), International Journal of Molecular Sciences, 22(19), 10279, pp. 1-27.

International Search Report and Written Opinion for International Application No. PCT/US2023/074113 dated Mar. 15, 2024, 14 pages.

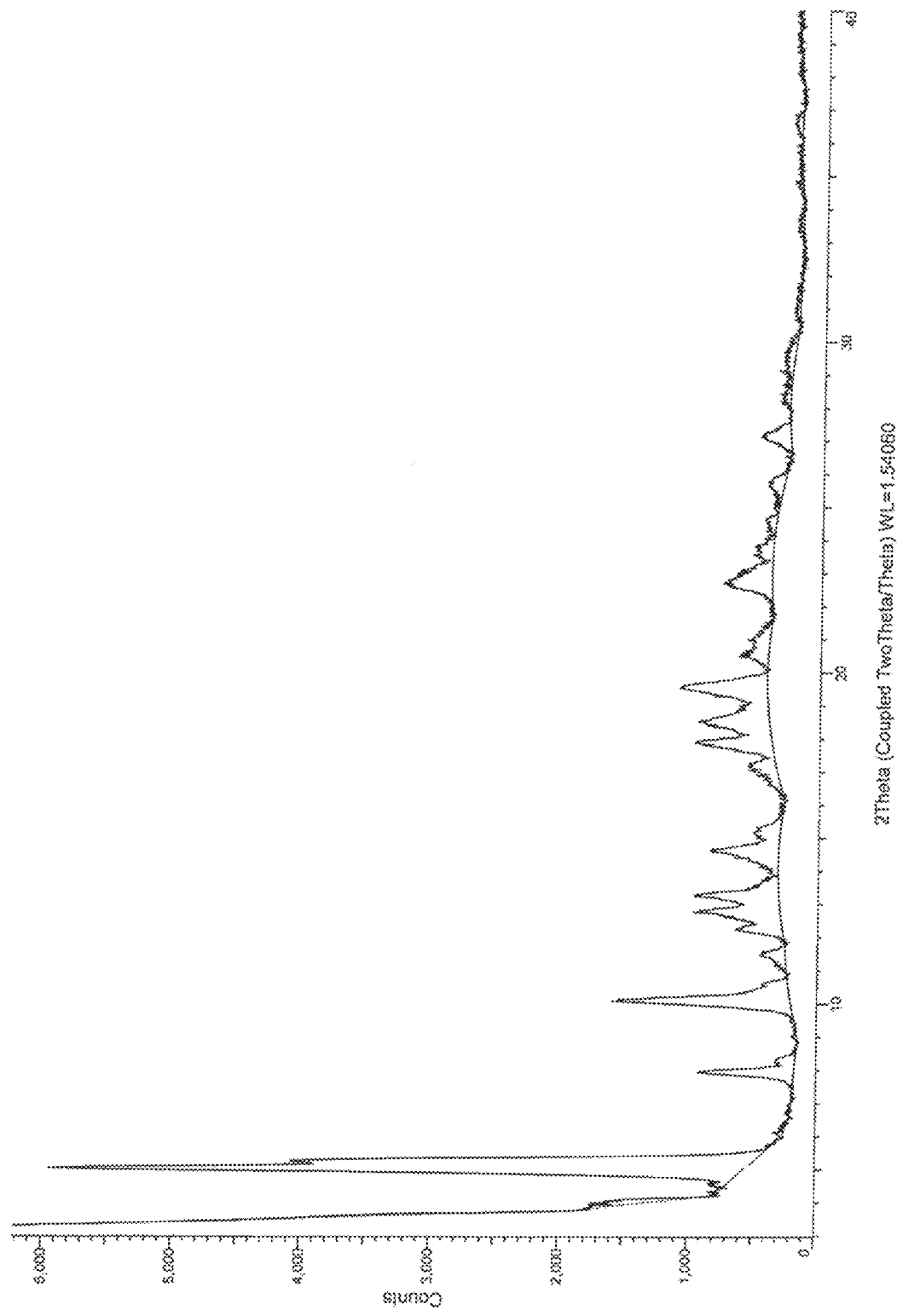

SALTS AND ESTERS OF APX3330 AND THERAPEUTIC USES THEREOF

CROSS-REFERENCE TO RELATED APPLICATIONS

This application is a continuation of U.S. patent application Ser. No. 18/367,631, filed Sep. 13, 2023, which claims the benefit of U.S. Provisional Application No. 63/375,647, filed Sep. 14, 2022, the disclosure of each of which is incorporated by reference herein in its entirety.

FIELD OF THE INVENTION

This invention relates to Compound 1 (APX3330) salts and esters, and processes for making Compound 1 salts and esters thereof. The invention also provides compositions comprising a Compound 1 salt or ester. The invention also provides compound of formula (I) and formula (II) and pharmaceutically acceptable salts thereof. The invention further provides compositions comprising a compound of formula (I) or formula (II), or a pharmaceutically acceptable salt thereof. The invention also provides methods for treating or preventing a disease, such as cancer, a liver disorder, an ocular disorder, a cardiovascular disorder, fibrosis, or an inflammatory disorder, comprising administering to a subject in need thereof an effective amount of a Compound 1 salt or ester; or compound of formula (I) or formula (II), or pharmaceutically acceptable salt thereof.

BACKGROUND OF THE INVENTION

Compound 1 (APX3330), also known as (2E)-2-[(4,5-Dimethoxy-2-methyl-3,6-dioxo-1,4-cyclohexadien-1-yl) methylene]-undecanoic acid, (2E)-2-[(4,5-dimethoxy-2-methyl-3,6-dioxocyclohexa-1,4-dien-1-yl)methylidene] undecanoic acid, (2E)-3-[2-(5,6-dimethoxy-3-methyl-1,4-benzoquinoyl)]-2-nonylpropenoic acid, "APX-3330" or "E3330", is undergoing clinical trials to evaluate its safety and efficacy to treat diabetic retinopathy and diabetic macular edema.

SUMMARY OF THE INVENTION

The present invention provides Compound 1 calcium salt that exhibits an X-ray powder diffraction (XRPD) pattern comprising a peak at 5.8±0.2 degrees 2-theta and a peak at 6.3±0.2 degrees 2-theta.

The invention further provides a Compound 1 calcium salt that exhibits an XRPD pattern comprising a peak at 5.8±0.2 degrees 2-theta, a peak at 6.3±0.2 degrees 2-theta, a peak at 13.7±0.2 degrees 2-theta, or a peak at 14.1±0.2 degrees 2-theta.

The invention further provides a Compound 1 calcium salt that exhibits an XRPD pattern comprising a peak at 4.1±0.2 degrees 2-theta, a peak at 5.3±0.2 degrees 2-theta, and a peak at 6.3±0.2 degrees 2-theta.

The invention further provides a Compound 1 calcium salt that exhibits an XRPD pattern that is substantially the same as that depicted in FIG. 1A.

The invention further provides a Compound 1 calcium salt that exhibits an XRPD pattern comprising the Table 1 peaks having at least 10% relative intensity.

The invention further provides a Compound 1 calcium salt that exhibits an XRPD pattern comprising a peak at 8.0±0.2 degrees 2-theta and a peak at 10.1±0.2 degrees 2-theta.

The invention further provides a Compound 1 calcium salt that exhibits an XRPD pattern comprising a peak at 8.0±0.2 degrees 2-theta, a peak at 10.1±0.2 degrees 2-theta, a peak at 13.3±0.2 degrees 2-theta, or a peak at 14.6±0.2 degrees 2-theta.

The present invention further provides a Compound 1 calcium salt that exhibits an XRPD pattern comprising a peak at 5.1±0.2 degrees 2-theta, a peak at 5.3±0.2 degrees 2-theta, and a peak at 10.1±0.2 degrees 2-theta.

The invention further provides a Compound 1 calcium salt that exhibits an XRPD pattern that is substantially the same as that depicted in FIG. 2A.

The invention further provides a Compound 1 calcium salt that exhibits an XRPD pattern comprising the Table 3 peaks having at least 10% relative intensity.

The present invention further provides a Compound 1 L-arginine salt that exhibits an XRPD pattern comprising a peak at 11.9±0.2 degrees 2-theta, a peak at 19.7±0.2 degrees 2-theta, and a peak at 20.2±0.2 degrees 2-theta.

The present invention further provides a Compound 1 L-arginine salt that exhibits an XRPD pattern that is substantially the same as that depicted in FIG. 4A.

The present invention further provides a Compound 1 L-arginine salt that exhibits an XRPD pattern comprising a peak at 3.9±0.2 degrees 2-theta, a peak at 13.1±0.2 degrees 2-theta, and a peak at 20.3±0.2 degrees 2-theta.

The present invention further provides a Compound 1 L-arginine salt that exhibits an XRPD pattern that is substantially the same as that depicted in FIG. 4B.

The present invention further provides a Compound 1 L-phenylalanine salt.

The present invention further provides a Compound 1 L-histidine salt.

The present invention further provides Compound 1 esters, which are compounds having the structure:

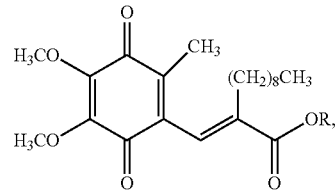

wherein R is $C_{10}$-$C_{24}$ hydrocarbyl group.

Each of the above compounds is a "compound of the invention".

The present invention further provides compositions comprising a compound of the invention and a pharmaceutically acceptable carrier or vehicle (each composition being a "composition of the invention").

The present invention further provides methods for treating or preventing an ocular disease, comprising administering to a subject in need thereof an effective amount of: a compound of the invention; a composition of the invention; a compound of formula (I)

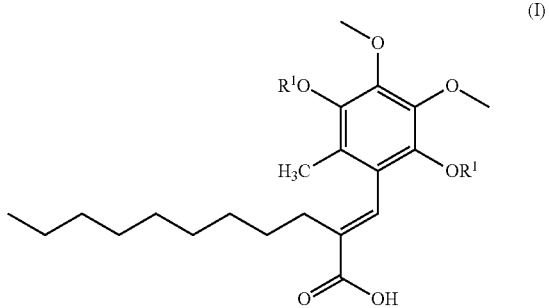

or a pharmaceutically acceptable salt thereof, wherein $R^1$ is each independently H, $C_1$-$C_6$ alkyl, or —C(O)($C_1$-$C_6$ alkyl); a compound of formula (II)

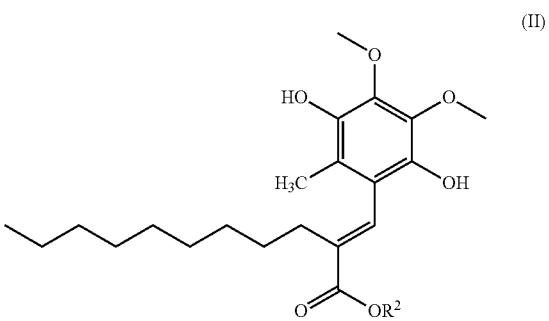

or a pharmaceutically acceptable salt thereof, wherein $R^2$ is $C_1$-$C_{24}$ hydrocarbyl group; a composition comprising a compound of formula (I) or a pharmaceutically acceptable salt thereof and a pharmaceutically acceptable carrier or vehicle; or a composition comprising a compound of formula (II) or a pharmaceutically acceptable salt thereof and a pharmaceutically acceptable carrier or vehicle.

The present invention further provides methods for treating or preventing cancer, cardiovascular disease, inflammation, chronic inflammatory disease, rheumatoid arthritis, idiopathic pulmonary fibrosis, acute adult respiratory distress syndrome, asthma, endometriosis, a keloid, systemic sclerosis, chemotherapy-induced peripheral neuropathy, stroke, gastro-intestinal dysfunction, chronic gastroesophageal reflux disease, von Hippel-Lindau syndrome, or a skin disorder, comprising administering to a subject in need thereof an effective amount of a compound of the invention, a composition of the invention, a compound of formula (I) or a pharmaceutically acceptable salt thereof, a compound of formula (II) or a pharmaceutically acceptable salt thereof, a composition comprising a compound of formula (I) or a pharmaceutically acceptable salt thereof and a pharmaceutically acceptable carrier or vehicle, or a composition comprising a compound of formula (II) or a pharmaceutically acceptable salt thereof and a pharmaceutically acceptable carrier or vehicle.

The present invention further provides methods for inhibiting angiogenesis, comprising administering to a subject in need thereof an effective amount of a compound of the invention, a composition of the invention, a compound of formula (I) or a pharmaceutically acceptable salt thereof, a compound of formula (II) or a pharmaceutically acceptable salt thereof, a composition comprising a compound of formula (I) or a pharmaceutically acceptable salt thereof and a pharmaceutically acceptable carrier or vehicle, or a composition comprising a compound of formula (II) or a pharmaceutically acceptable salt thereof and a pharmaceutically acceptable carrier or vehicle.

The present invention further provides methods for inhibiting vascular endothelial growth factor (VEGF) or VEGF protein expression, comprising administering to a subject in need thereof an effective amount of a compound of the invention, a composition of the invention, a compound of formula (I) or a pharmaceutically acceptable salt thereof, a compound of formula (II) or a pharmaceutically acceptable salt thereof, a composition comprising a compound of formula (I) or a pharmaceutically acceptable salt thereof and a pharmaceutically acceptable carrier or vehicle, or a composition comprising a compound of formula (II) or a pharmaceutically acceptable salt thereof and a pharmaceutically acceptable carrier or vehicle.

The present invention further provides methods for inhibiting capillary tube formation, comprising administering to a subject in need thereof an effective amount of a compound of the invention, a composition of the invention, a compound of formula (I) or a pharmaceutically acceptable salt thereof, a compound of formula (II) or a pharmaceutically acceptable salt thereof, a composition comprising a compound of formula (I) or a pharmaceutically acceptable salt thereof and a pharmaceutically acceptable carrier or vehicle, or a composition comprising a compound of formula (II) or a pharmaceutically acceptable salt thereof and a pharmaceutically acceptable carrier or vehicle.

The present invention further provides methods for treating or preventing a hepatic disease, comprising administering to a subject in need thereof an effective amount of a compound of the invention or a composition of the invention.

The present invention further provides methods for suppressing neuronal sensitivity, comprising administering to a subject in need thereof an effective amount of a compound of the invention, a composition of the invention, a compound of formula (I) or a pharmaceutically acceptable salt thereof, a compound of formula (II) or a pharmaceutically acceptable salt thereof, a composition comprising a compound of formula (I) or a pharmaceutically acceptable salt thereof and a pharmaceutically acceptable carrier or vehicle, or a composition comprising a compound of formula (II) or a pharmaceutically acceptable salt thereof and a pharmaceutically acceptable carrier or vehicle.

The present invention further provides methods for treating pain, comprising administering to a subject in need thereof an effective amount of a compound of the invention, a composition of the invention, a compound of formula (I) or a pharmaceutically acceptable salt thereof, a compound of formula (II) or a pharmaceutically acceptable salt thereof, a composition comprising a compound of formula (I) or a pharmaceutically acceptable salt thereof and a pharmaceutically acceptable carrier or vehicle, or a composition comprising a compound of formula (II) or a pharmaceutically acceptable salt thereof and a pharmaceutically acceptable carrier or vehicle.

The present invention further provides methods for enhancing DNA base excision repair, comprising administering to a subject in need thereof an effective amount of a compound of the invention, a composition of the invention, a compound of formula (I) or a pharmaceutically acceptable salt thereof, a compound of formula (II) or a pharmaceutically acceptable salt thereof, a composition comprising a compound of formula (I) or a pharmaceutically acceptable salt thereof and a pharmaceutically acceptable carrier or vehicle, or a composition comprising a compound of formula (II) or a pharmaceutically acceptable salt thereof and a pharmaceutically acceptable carrier or vehicle.

The present invention further provides methods for enhancing neuronal DNA repair function, comprising administering to a subject in need thereof an effective amount of a compound of the invention, a composition of the invention, a compound of formula (I) or a pharmaceutically acceptable salt thereof, a compound of formula (II) or a pharmaceutically acceptable salt thereof, a composition comprising a compound of formula (I) or a pharmaceutically acceptable salt thereof and a pharmaceutically acceptable carrier or vehicle, or a composition comprising a compound of formula (II) or a pharmaceutically acceptable salt thereof and a pharmaceutically acceptable carrier or vehicle.

The present invention further provides methods for treating or preventing geographic atrophy, choroidal neovascularization, or corneal graft rejection, comprising administering to a subject in need thereof an effective amount of a compound of the invention, a composition of the invention, a compound of formula (I) or a pharmaceutically acceptable salt thereof, a compound of formula (II) or a pharmaceutically acceptable salt thereof, a composition comprising a compound of formula (I) or a pharmaceutically acceptable salt thereof and a pharmaceutically acceptable carrier or vehicle, or a composition comprising a compound of formula (II) or a pharmaceutically acceptable salt thereof and a pharmaceutically acceptable carrier or vehicle.

The present invention further provides methods for treating diabetic retinopathy (DR), comprising administering to a subject in need thereof an effective amount of a Compound 1 calcium salt exhibiting an X-ray powder diffraction (XRPD) pattern comprising a peak at 5.8±0.2 degrees 2-theta and a peak at 6.3±0.2 degrees 2-theta.

The present invention further provides methods for treating diabetic retinopathy (DR), comprising administering to a subject in need thereof an effective amount of a Compound 1 calcium salt exhibiting an X-ray powder diffraction (XRPD) pattern comprising a peak at 4.1±0.2 degrees 2-theta, a peak at 5.3±0.2 degrees 2-theta, and a peak at 6.3±0.2 degrees 2-theta.

The present invention further provides methods for treating diabetic retinopathy (DR), comprising administering to a subject in need thereof an effective amount of a Compound 1 calcium salt exhibiting an X-ray powder diffraction (XRPD) pattern comprising a peak at 8.0±0.2 degrees 2-theta and a peak at 10.1±0.2 degrees 2-theta.

The present invention further provides methods for treating diabetic retinopathy (DR), comprising administering to a subject in need thereof an effective amount of a Compound 1 calcium salt exhibiting an X-ray powder diffraction (XRPD) pattern comprising a peak at 5.1±0.2 degrees 2-theta, a peak at 5.3±0.2 degrees 2-theta, and a peak at 10.1±0.2 degrees 2-theta.

The present invention further provides methods for treating diabetic macular edema (DME), comprising administering to a subject in need thereof an effective amount of a Compound 1 calcium salt exhibiting an X-ray powder diffraction (XRPD) pattern comprising a peak at 5.8±0.2 degrees 2-theta and a peak at 6.3±0.2 degrees 2-theta.

The present invention further provides methods for treating diabetic macular edema (DME), comprising administering to a subject in need thereof an effective amount of a Compound 1 calcium salt exhibiting an X-ray powder diffraction (XRPD) pattern comprising a peak at 4.1±0.2 degrees 2-theta, a peak at 5.3±0.2 degrees 2-theta, and a peak at 6.3±0.2 degrees 2-theta.

The present invention further provides methods for treating diabetic macular edema (DME), comprising administering to a subject in need thereof an effective amount of a Compound 1 calcium salt exhibiting an X-ray powder diffraction (XRPD) pattern comprising a peak at 8.0±0.2 degrees 2-theta and a peak at 10.1±0.2 degrees 2-theta.

The present invention further provides methods for treating diabetic macular edema (DME), comprising administering to a subject in need thereof an effective amount of a Compound 1 calcium salt exhibiting an X-ray powder diffraction (XRPD) pattern comprising a peak at 5.1±0.2 degrees 2-theta, a peak at 5.3±0.2 degrees 2-theta, and a peak at 10.1±0.2 degrees 2-theta.

Each of the above methods is a "method of the invention".

BRIEF DESCRIPTION OF THE DRAWINGS

FIG. 2A shows an XRPD pattern of the Compound 1 calcium salt obtained as described in Example 2.

DETAILED DESCRIPTION OF THE INVENTION

Definitions

Figure 1A:
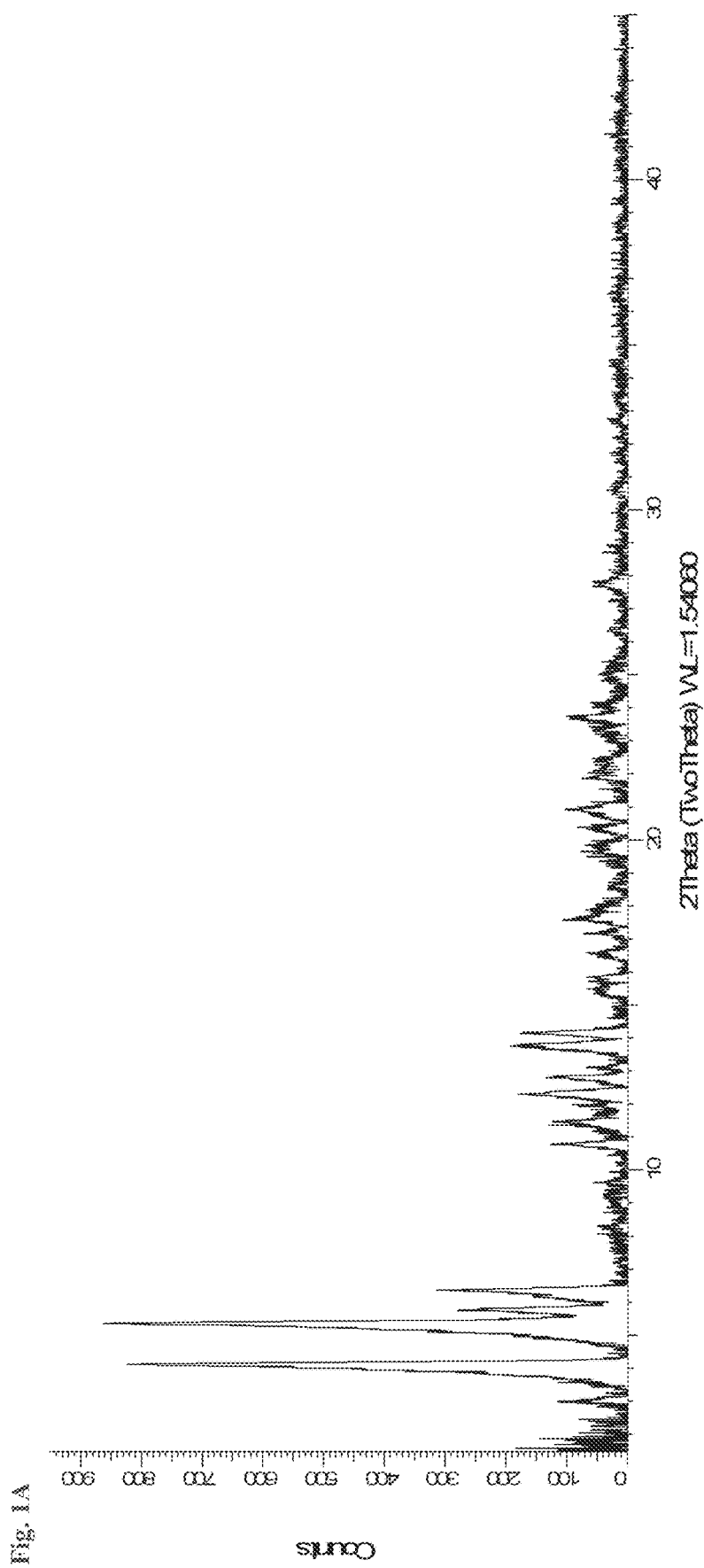
FIG. 1A shows an XRPD pattern of a Compound 1 calcium salt obtained as described in Example 1.

The term "about" when immediately preceding a numerical value means ±10% of the numerical value.

Throughout the present specification, numerical ranges are provided for certain quantities. These ranges comprise all subranges therein. Thus, the range "from 50 to 80" includes all possible ranges therein (e.g., 51-79, 52-78, 53-77, 54-76, 55-75, 60-70, etc.). Furthermore, all values within a given range may be an endpoint for the range encompassed thereby (e.g., the range 50-80 includes the ranges with endpoints such as 55-80, 50-75, etc.).

As used herein, "effective amount" refers to an amount of a compound or composition that is effective to treat or prevent an ocular disease; treat or prevent cancer, cardiovascular disease, inflammation, chronic inflammatory disease, rheumatoid arthritis, idiopathic pulmonary fibrosis, acute adult respiratory distress syndrome, asthma, endometriosis, a keloid, systemic sclerosis, chemotherapy-induced peripheral neuropathy, stroke, gastro-intestinal dysfunction, chronic gastroesophageal reflux disease, von Hippel-Lindau syndrome, or a skin disorder; inhibit angiogenesis; inhibit vascular endothelial growth factor (VEGF) or VEGF protein expression; inhibit capillary tube formation; treat or prevent a hepatic disease; suppress neuronal sensitivity; treat pain; enhance DNA base excision repair; enhance neuronal DNA repair function; or treat or prevent geographic atrophy, choroidal neovascularization, corneal graft rejection, or Barrett's esophagus.

All weight percentages (i.e., "% by weight" and "wt. %" and w/w) referenced herein, unless otherwise indicated, are relative to the total weight of the compound or composition of the invention, as the case may be.

The term "pharmaceutically acceptable salt" includes a base addition salt. Pharmaceutically acceptable salts can be obtained by reacting a compound of the invention functioning as an acid, with an inorganic or organic base to form a salt, for example, a sodium, potassium, lithium, ammonium, calcium, magnesium, iron, zinc, copper, manganese, aluminum, ammonium, isopropylammonium, trimethylammonium, phenylalanine, arginine, or histidine salt. In some embodiments, the pharmaceutically acceptable salt is a mono-salt. In some embodiments, the pharmaceutically acceptable salt is a di-salt. In some embodiments, the pharmaceutically acceptable salt is a tri-salt. Those skilled in the art will further recognize that pharmaceutically acceptable salts can be prepared by reaction of a compound with an appropriate inorganic or organic acid or base via any of a number of known methods.

As used herein in connection with a compound of the invention, an "impurity" is a compound or substance other than the compound of the invention.

As used herein, "isolated" means isolated from a chemical synthesis reaction mixture. In some embodiments, an isolated compound is at least 95% pure and comprises no more than 5% of one or more impurities by weight, moles, or volume. By "x % pure" means that a compound includes no more than (100-x) % of one or more impurities by weight, moles, or volume. In some embodiments, an isolated compound is at least 96%, at least 97%, at least 98%, or at least 99% pure, and comprises no more than 4%, no more than 3%, no more than 2%, or no more than 1% of an impurity, respectively, by weight, moles, or volume. In some embodiments, the one or more impurities, if any, are present in the compound as a percent by weight. In some embodiments, the one or more impurities, if any, are present in the compound as a percent by mole. In some embodiments, the one or more impurities, if any, are present in the compound as a percent by volume.

As used herein, "predominantly amorphous" when used in connection with a compound means an admixture of the compound in amorphous form and the compound in crystalline form, wherein the admixture contains at least 50% of the compound in amorphous form by weight of the admixture.

As used herein, "substantially the same as" when used in connection with an XRPD pattern means that each peak (having an at least 2% relative intensity) of the XRPD pattern differs from a respective peak of a reference or comparative XRPD pattern by no more than ±0.2 degrees 2-theta. The most intense peak in an XRPD pattern is assigned 100% relative peak intensity and the intensities of all other peaks in the XRPD pattern is measured relative to the most intense peak (relative peak intensity).

As used herein, "substantially the same as" when used in connection with a DSC thermogram means that each peak of the DSC thermogram differs from a respective peak of a reference or comparative DSC thermogram by no more than ±3° C.

As used herein, "substantially the same as" when used in connection with a TG thermogram means that each peak of the TG thermogram differs from a respective peak of a reference or comparative TG thermogram by no more than ±2%.

As used herein, "substantially the same as" when used in connection with a FT-IR spectrum means that each peak of the spectrum differs from a respective peak of a reference or comparative FT-IR spectrum by no more than ±5 cm$^{-1}$.

As used herein, "substantially the same as" when used in connection with a FT-Raman spectrum means that each peak of the spectrum differs from a respective peak of a stated reference or comparative FT-Raman spectrum by no more than ±5 cm$^{-1}$.

As used herein, "stable" when used in connection with a compound means that the compound comprises no more than 10% of a degradation product by weight of the compound.

Compounds of the Invention

The present invention provides Compound 1 salts, Compound 1 esters and pharmaceutically acceptable salts of the Compound 1 esters.
Compound 1 has the Structure:

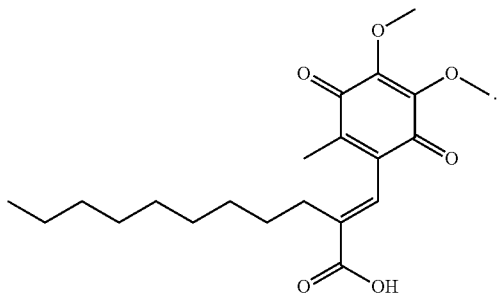 [SMILES: CCCCCCCCC/C(=C\C1=C(C)C(=O)C(OC)=C(OC)C1=O)C(=O)O]

In some embodiments, the Compound 1 salt is a Compound 1 calcium salt, a Compound 1 L-arginine salt, a Compound 1 phenylalanine salt, or a Compound 1 histidine salt. In some embodiments, the Compound 1 salt is a crystalline salt.

In some embodiments, the compound of the invention is a Compound 1 calcium salt.

In some embodiments, the Compound 1 calcium salt exhibits an XRPD pattern comprising a peak at 4.1±0.2 degrees 2-theta, a peak at 5.3±0.2 degrees 2-theta, and a peak at 6.3±0.2 degrees 2-theta. In some embodiments, the XRPD pattern further comprises a peak at 5.8±0.2 degrees 2-theta or a peak at 14.1±0.2 degrees 2-theta. In some embodiments, the XRPD pattern further comprises a peak at 12.8±0.2 degrees 2-theta or a peak at 13.7±0.2 degrees 2-theta. In some embodiments, the XRPD pattern further comprises a peak at 10.8±0.2 degrees 2-theta. In some embodiments, the XRPD pattern further comprises a peak at 6.1±0.2 degrees 2-theta or a peak at 11.4±0.2 degrees 2-theta. In some embodiments, the XRPD pattern further comprises a peak at 17.6±0.2 degrees 2-theta or a peak at 20.3±0.2 degrees 2-theta. In some embodiments, the XRPD pattern further comprises a peak at 3.0±0.2 degrees 2-theta or a peak at 12.3±0.2 degrees 2-theta. In some embodiments, the XRPD pattern further comprises a peak at 11.4±0.2 degrees 2-theta, a peak at 17.6±0.2 degrees 2-theta, and a peak at 21.9±0.2 degrees 2-theta.

In some embodiments, the Compound 1 calcium salt exhibits an XRPD pattern comprising a peak at 4.1±0.2 degrees 2-theta, a peak at 5.3±0.2 degrees 2-theta, and a peak at 6.3±0.2 degrees 2-theta. In some embodiments, the XRPD pattern further comprises a peak at 5.8±0.2 degrees 2-theta or a peak at 13.7±0.2 degrees 2-theta. In some embodiments, the XRPD pattern further comprises a peak at 12.8±0.2 degrees 2-theta or a peak at 14.1±0.2 degrees 2-theta. In some embodiments, the XRPD pattern further comprises a peak at 12.3±0.2 degrees 2-theta. In some embodiments, the XRPD pattern further comprises a peak at 11.4±0.2 degrees 2-theta. In some embodiments, the XRPD pattern further comprises a peak at 10.8±0.2 degrees 2-theta In some embodiments, the Compound 1 calcium salt exhibits an XRPD pattern comprising a peak at 4.1±0.2 degrees 2-theta, a peak at 5.4±0.2 degrees 2-theta, and a peak at 6.4±0.2 degrees 2-theta. In some embodiments, the XRPD pattern further comprises a peak at 5.8±0.2 degrees 2-theta or a peak at 13.8±0.2 degrees 2-theta. In some embodiments, the XRPD pattern further comprises a peak at 12.8±0.2 degrees 2-theta or a peak at 14.2±0.2 degrees 2-theta. In some embodiments, the XRPD pattern further comprises a peak at 12.3±0.2 degrees 2-theta. In some embodiments, the XRPD pattern further comprises a peak at 12.0±0.2 degrees 2-theta or a peak at 11.4±0.2 degrees 2-theta. In some embodiments, the XRPD pattern further comprises a peak at 10.8±0.2 degrees 2-theta or a peak at 20.9±0.2 degrees 2-theta. In some embodiments, the XRPD pattern further comprises a peak at 13.1±0.2 degrees 2-theta, a peak at 17.6±0.2 degrees 2-theta, and a peak at 23.7±0.2 degrees 2-theta.

In some embodiments, the Compound 1 calcium salt exhibits an XRPD pattern comprising a peak at 4.1±0.2 degrees 2-theta, a peak at 5.3±0.2 degrees 2-theta, and a peak at 6.3±0.2 degrees 2-theta, wherein the peak at 4.1±0.2 degrees 2-theta, the peak at 5.3±0.2 degrees 2-theta, and the peak at 6.3±0.2 degrees 2-theta, have a relative peak intensity (%) of greater than 30%. In some embodiments, the XRPD pattern further comprises a peak at 5.8±0.2 degrees 2-theta or a peak at 14.1±0.2 degrees 2-theta, wherein the peak at 5.8±0.2 degrees 2-theta and the peak at 14.1±0.2 degrees 2-theta have a relative peak intensity (%) of greater than 15%. In some embodiments, the XRPD pattern further comprises a peak at 12.8±0.2 degrees 2-theta or a peak at 13.7±0.2 degrees 2-theta, wherein the peak at 12.8±0.2 degrees 2-theta and the peak at 13.7±0.2 degrees 2-theta have a relative peak intensity (%) of greater than 10%. In some embodiments, the XRPD pattern further comprises a peak at 10.8±0.2 degrees 2-theta, wherein the peak has a relative peak intensity (%) of greater than 10%. In some embodiments, the XRPD pattern further comprises a peak at 6.1±0.2 degrees 2-theta or a peak at 11.4±0.2 degrees 2-theta, wherein the peak at 6.1±0.2 degrees 2-theta and the peak at 11.4±0.2 degrees 2-theta have a relative peak intensity (%) of greater than 10%. In some embodiments, the XRPD pattern further comprises a peak at 17.6±0.2 degrees 2-theta or a peak at 20.3±0.2 degrees 2-theta, wherein the peak at 17.6±0.2 degrees 2-theta and the peak at 20.3±0.2 degrees 2-theta have a relative peak intensity (%) of greater than 8%. In some embodiments, the XRPD pattern further comprises a peak at 3.0±0.2 degrees 2-theta or a peak at 12.3±0.2 degrees 2-theta, wherein the peak at 3.0±0.2 degrees 2-theta and the peak at 12.3±0.2 degrees 2-theta have a relative peak intensity (%) of greater than 5%. In some embodiments, the XRPD pattern further comprises a peak at 11.4±0.2 degrees 2-theta, a peak at 17.6±0.2 degrees 2-theta, or a peak at 21.9±0.2 degrees 2-theta, wherein the peak at 11.4±0.2 degrees 2-theta, the peak at 17.6±0.2 degrees 2-theta, and the peak at 21.9±0.2 degrees 2-theta have a relative peak intensity (%) of greater than 5%.

In some embodiments, the Compound 1 calcium salt exhibits an XRPD pattern comprising a peak at 4.1±0.2 degrees 2-theta, a peak at 5.4±0.2 degrees 2-theta, and a peak at 6.4±0.2 degrees 2-theta, wherein the peak at 4.1±0.2 degrees 2-theta, the peak at 5.4±0.2 degrees 2-theta, and the peak at 6.4±0.2 degrees 2-theta have a relative peak intensity (%) of greater than 30%. In some embodiments, the XRPD pattern further comprises a peak at 5.8±0.2 degrees 2-theta or a peak at 13.8±0.2 degrees 2-theta, wherein the peak at 5.8±0.2 degrees 2-theta and the peak at 13.8±0.2 degrees 2-theta have a relative peak intensity (%) of greater than 15%. In some embodiments, the XRPD pattern further comprises a peak at 12.8±0.2 degrees 2-theta or a peak at 14.2±0.2 degrees 2-theta, wherein the peak at 12.8±0.2 degrees 2-theta and the peak at 14.2±0.2 degrees 2-theta have a relative peak intensity (%) of greater than 10%. In some embodiments, the XRPD pattern further comprises a peak at 12.3±0.2 degrees 2-theta, wherein the peak has a relative peak intensity (%) of greater than 10%. In some embodiments, the XRPD pattern further comprises a peak at 12.0±0.2 degrees 2-theta or a peak at 11.4±0.2 degrees 2-theta, wherein the peak at 12.0±0.2 degrees 2-theta and the peak at 11.4±0.2 degrees 2-theta have a relative peak intensity (%) of greater than 10%. In some embodiments, the XRPD pattern further comprises a peak at 10.8±0.2 degrees 2-theta or a peak at 20.9±0.2 degrees 2-theta, wherein the peak at 10.8±0.2 degrees 2-theta and the peak at 20.9±0.2 degrees 2-theta have a relative peak intensity (%) of greater than 6%. In some embodiments, the XRPD pattern further comprises a peak at 13.1±0.2 degrees 2-theta, a peak at 17.6±0.2 degrees 2-theta, or a peak at 23.7±0.2 degrees 2-theta, wherein the peak at 13.1±0.2 degrees 2-theta, the peak at 17.6±0.2 degrees 2-theta, and the peak at 23.7±0.2 degrees 2-theta have a relative peak intensity (%) of greater than 5%.

In some embodiments, the Compound 1 calcium salt exhibits an XRPD pattern comprising a peak at 6.3±0.2 degrees 2-theta. In some embodiments, the Compound 1 calcium salt exhibits an XRPD pattern comprising a peak at 5.8±0.2 degrees 2-theta. In some embodiments, the Compound 1 calcium salt exhibits an XRPD pattern comprising a peak at 13.7±0.2 degrees 2-theta. In some embodiments, the Compound 1 calcium salt exhibits an XRPD pattern comprising a peak at 14.1±0.2 degrees 2-theta.

In some embodiments, the Compound 1 calcium salt exhibits an XRPD pattern comprising a peak at 6.3±0.2 degrees 2-theta and a peak at 5.8±0.2 degrees 2-theta. In some embodiments, the Compound 1 calcium salt exhibits an XRPD pattern comprising a peak at 6.3±0.2 degrees 2-theta and a peak at 14.1±0.2 degrees 2-theta. In some embodiments, the Compound 1 calcium salt exhibits an XRPD pattern comprising a peak at 6.3±0.2 degrees 2-theta, a peak at 5.8±0.2 degrees 2-theta, and a peak at 14.1±0.2 degrees 2-theta. In some embodiments, the Compound 1 calcium salt exhibits an XRPD pattern comprising a peak at 5.8±0.2 degrees 2-theta, a peak at 6.3±0.2 degrees 2-theta, and a peak at 13.7±0.2 degrees 2-theta. In some embodiments, the Compound 1 calcium salt exhibits an XRPD pattern comprising a peak at 5.8±0.2 degrees 2-theta, a peak at 6.3±0.2 degrees 2-theta, a peak at 13.7±0.2 degrees 2-theta, or a peak at 14.1±0.2 degrees 2-theta. In some embodiments, the Compound 1 calcium salt exhibits an XRPD pattern comprising a peak at 5.8±0.2 degrees 2-theta, a peak at 6.3±0.2 degrees 2-theta, a peak at 13.7±0.2 degrees 2-theta, and a peak at 14.1±0.2 degrees 2-theta.

In some embodiments, the Compound 1 calcium salt exhibits an XRPD pattern comprising a peak at 5.8±0.2 degrees 2-theta and a peak at 6.3±0.2 degrees 2-theta. In some embodiments, the XRPD pattern further comprises a peak at 13.7±0.2 degrees 2-theta or a peak at 14.1±0.2 degrees 2-theta.

In some embodiments, the Compound 1 calcium salt exhibits an XRPD pattern comprising a peak at 5.8±0.2 degrees 2-theta and a peak at 6.3±0.2 degrees 2-theta. In some embodiments, the XRPD pattern further comprises a peak at 13.7±0.2 degrees 2-theta or a peak at 14.1±0.2 degrees 2-theta.

In some embodiments, the Compound 1 calcium salt exhibits an XRPD pattern comprising a peak at 6.4±0.2 degrees 2-theta. In some embodiments, the Compound 1 calcium salt exhibits an XRPD pattern comprising a peak at 5.8±0.2 degrees 2-theta. In some embodiments, the Compound 1 calcium salt exhibits an XRPD pattern comprising a peak at 13.8±0.2 degrees 2-theta. In some embodiments, the Compound 1 calcium salt exhibits an XRPD pattern comprising a peak at 14.2±0.2 degrees 2-theta.

In some embodiments, the Compound 1 calcium salt exhibits an XRPD pattern comprising a peak at 6.4±0.2 degrees 2-theta and a peak at 5.8±0.2 degrees 2-theta. In some embodiments, the Compound 1 calcium salt exhibits an XRPD pattern comprising a peak at 6.4±0.2 degrees 2-theta and a peak at 14.2±0.2 degrees 2-theta. In some embodiments, the Compound 1 calcium salt exhibits an XRPD pattern comprising a peak at 6.4±0.2 degrees 2-theta, a peak at 5.8±0.2 degrees 2-theta, and a peak at 14.2±0.2 degrees 2-theta. In some embodiments, the Compound 1 calcium salt exhibits an XRPD pattern comprising a peak at 5.8±0.2 degrees 2-theta, a peak at 6.4±0.2 degrees 2-theta, and a peak at 13.8±0.2 degrees 2-theta. In some embodiments, the Compound 1 calcium salt exhibits an XRPD pattern comprising a peak at 6.4±0.2 degrees 2-theta, a peak at 5.8±0.2 degrees 2-theta, a peak at 13.8±0.2 degrees 2-theta, or a peak at 14.2±0.2 degrees 2-theta. In some embodiments, the Compound 1 calcium salt exhibits an XRPD pattern comprising a peak at 6.4±0.2 degrees 2-theta, a peak at 5.8±0.2 degrees 2-theta, a peak at 13.8±0.2 degrees 2-theta, and a peak at 14.2±0.2 degrees 2-theta.

In some embodiments, the Compound 1 calcium salt exhibits an XRPD pattern comprising a peak at 5.8±0.2 degrees 2-theta and a peak at 6.4±0.2 degrees 2-theta. In some embodiments, the XRPD pattern further comprises a peak at 13.8±0.2 degrees 2-theta or a peak at 14.2±0.2 degrees 2-theta.

In some embodiments, the Compound 1 calcium salt exhibits an XRPD pattern comprising a peak at 5.8±0.2 degrees 2-theta and a peak at 6.4±0.2 degrees 2-theta. In some embodiments, the XRPD pattern further comprises a peak at 13.8±0.2 degrees 2-theta or a peak at 14.2±0.2 degrees 2-theta.

In some embodiments, the Compound 1 calcium salt exhibits an XRPD pattern comprising a peak at 6.3±0.2 degrees 2-theta and 1 peak, 2 peaks, 3 peaks, 4 peaks, 5 peaks, 6 peaks, 7 peaks, 8 peaks, or 9 peaks of Table 1. In some embodiments, the Compound 1 calcium salt exhibits an XRPD pattern comprising a peak at 6.3±0.2 degrees 2-theta and 1 peak, 2 peaks, 3 peaks, 4 peaks, 5 peaks, 6 peaks, 7 peaks, 8 peaks, or 9 peaks of the following peaks: a peak at 4.1±0.2 degrees 2-theta, a peak at 5.3±0.2 degrees 2-theta, a peak at 5.8±0.2 degrees 2-theta, a peak at 6.1±0.2 degrees 2-theta, a peak at 10.8±0.2 degrees 2-theta, a peak at 11.4±0.2 degrees 2-theta, a peak at 12.8±0.2 degrees 2-theta, a peak at 13.7±0.2 degrees 2-theta, and 14.1±0.2 degrees 2-theta.

In some embodiments, the Compound 1 calcium salt exhibits an XRPD pattern comprising a peak at 6.4±0.2 degrees 2-theta and 1 peak, 2 peaks, 3 peaks, 4 peaks, 5 peaks, 6 peaks, 7 peaks, 8 peaks, or 9 peaks of Table 1. In some embodiments, the Compound 1 calcium salt exhibits an XRPD pattern comprising a peak at 6.4±0.2 degrees 2-theta and 1 peak, 2 peaks, 3 peaks, 4 peaks, 5 peaks, 6 peaks, 7 peaks, 8 peaks, or 9 peaks of the following peaks: a peak at 4.1±0.2 degrees 2-theta, a peak at 5.4±0.2 degrees 2-theta, a peak at 5.8±0.2 degrees 2-theta, a peak at 11.4±0.2 degrees 2-theta, a peak at 12.0±0.2 degrees 2-theta, a peak at 12.3±0.2 degrees 2-theta, a peak at 12.8±0.2 degrees 2-theta, a peak at 13.8±0.2 degrees 2-theta, and 14.2±0.2 degrees 2-theta.

In some embodiments, the Compound 1 calcium salt exhibits an XRPD pattern comprising a Table 1 peak having a relative peak intensity (%) of greater than 30%. In some embodiments, the Compound 1 calcium salt exhibits an XRPD pattern comprising a Table 1 peak having a relative peak intensity (%) of greater than 20%. In some embodiments, the Compound 1 calcium salt exhibits an XRPD pattern comprising a Table 1 peak having a relative peak intensity (%) of greater than 15%. In some embodiments, the Compound 1 calcium salt exhibits an XRPD pattern comprising a Table 1 peak having a relative peak intensity (%) of greater than 5%.

In some embodiments, the Compound 1 calcium salt exhibits an XRPD pattern that is substantially the same as that depicted in FIG. 1A.

In some embodiments, the Compound 1 calcium salt exhibits a DSC thermogram comprising an endothermic peak having a peak maximum of from about 80° C. to about 84° C. In some embodiments, the Compound 1 calcium salt exhibits a DSC thermogram comprising an endothermic peak having a peak maximum of from about 81° C. to about 83° C. In some embodiments, the Compound 1 calcium salt exhibits a DSC thermogram comprising an endothermic peak having a peak maximum of about 83° C. In some embodiments, the Compound 1 calcium salt exhibits a DSC thermogram comprising an endothermic peak that onsets at about 58° C. In some embodiments, the Compound 1 calcium salt exhibits a DSC thermogram comprising an endothermic peak that onsets at about 54° C.

In some embodiments, the Compound 1 calcium salt exhibits a DSC thermogram comprising an exothermic peak having a peak maximum of from about 213° C. to about 216° C. In some embodiments, the Compound 1 calcium salt exhibits a DSC thermogram comprising an exothermic peak having a peak maximum of from about 215° C. to about 216° C. In some embodiments, the Compound 1 calcium salt exhibits a DSC thermogram comprising an exothermic peak having a peak maximum of from about 208° C. to about 216° C. In some embodiments, the Compound 1 calcium salt exhibits a DSC thermogram comprising an exothermic peak having a peak maximum of from about 210° C. to about 214° C. In some embodiments, the Compound 1 calcium salt exhibits a DSC thermogram comprising an exothermic peak that onsets at about 212° C.

Figure 1B:
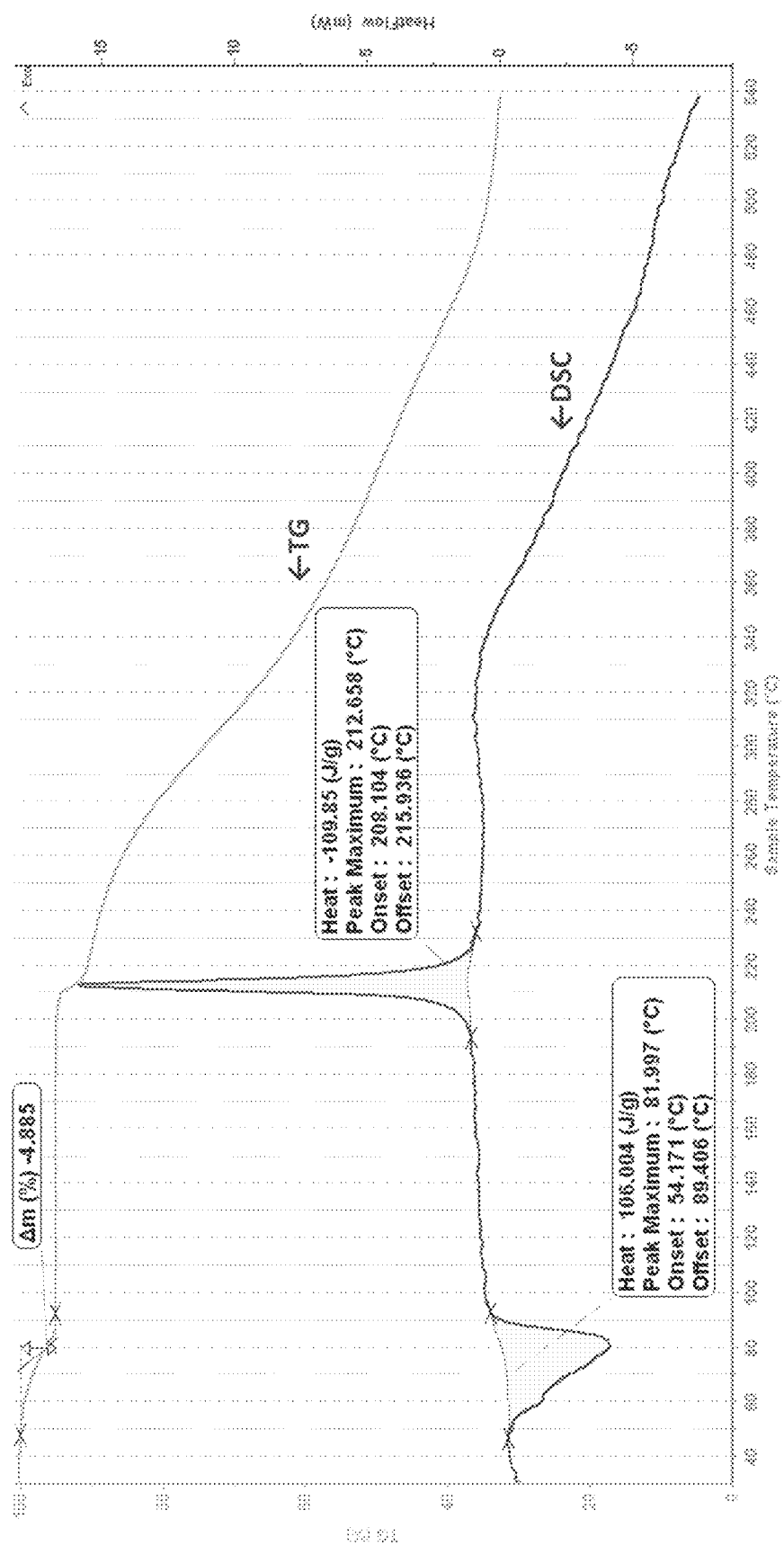
FIG. 1B shows an overlay of a thermo-gravimetric (TG) thermogram and a differential scanning calorimetry (DSC) thermogram of the Compound 1 calcium salt obtained as described in Example 1.

In some embodiments, the Compound 1 calcium salt exhibits a DSC thermogram that is substantially the same as that depicted in FIG. 1B.

In some embodiments, the Compound 1 calcium salt exhibits a thermo-gravimetric (TG) thermogram that is substantially the same as that depicted in FIG. 1B.

Figure 1C:
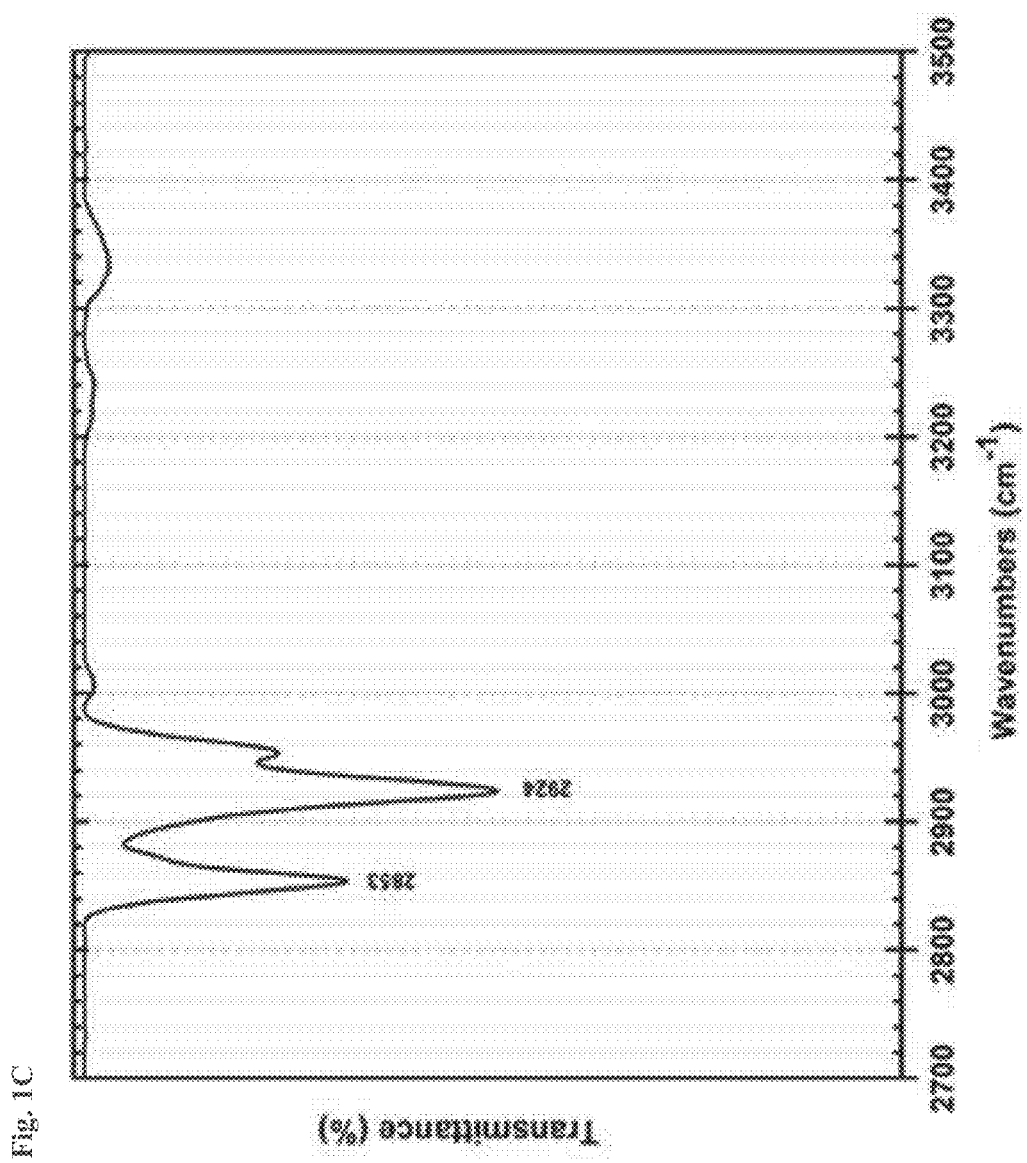
FIG. 1C and FIG. 1D show an FT-IR spectrum of the Compound 1 calcium salt obtained as described in Example 1.
Figure 1D:
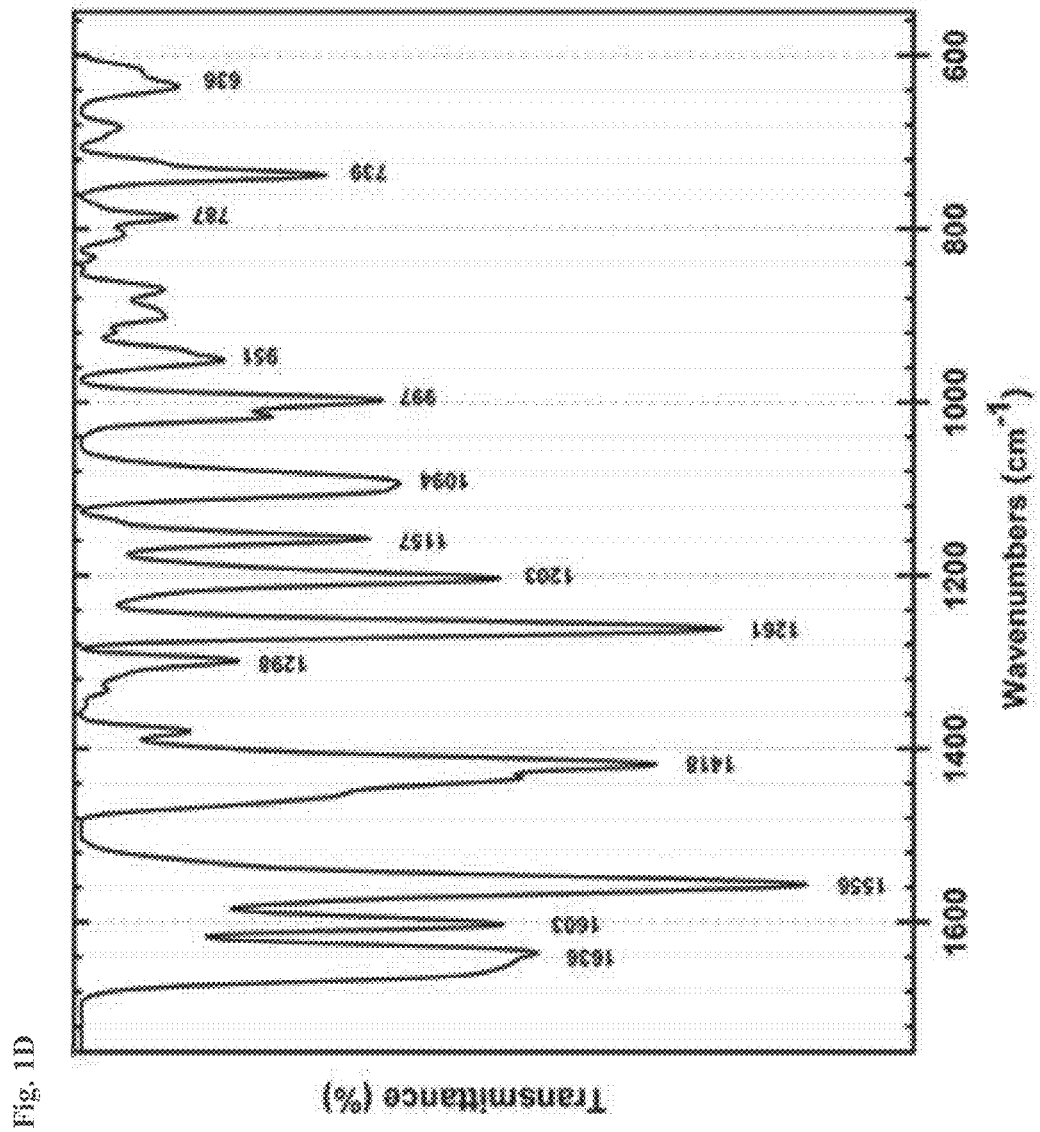

In some embodiments, the Compound 1 calcium salt exhibits an FT-IR spectrum that is substantially the same in the spectrum's region from 2700 $cm^{-1}$ to 3500 $cm^{-1}$ as that depicted in FIG. 1C. In some embodiments, the Compound 1 calcium salt exhibits an FT-IR spectrum that is substantially the same in the spectrum's region from 560 $cm^{-1}$ to 1700 $cm^{-1}$ as that depicted in FIG. 1D.

Figure 1E:
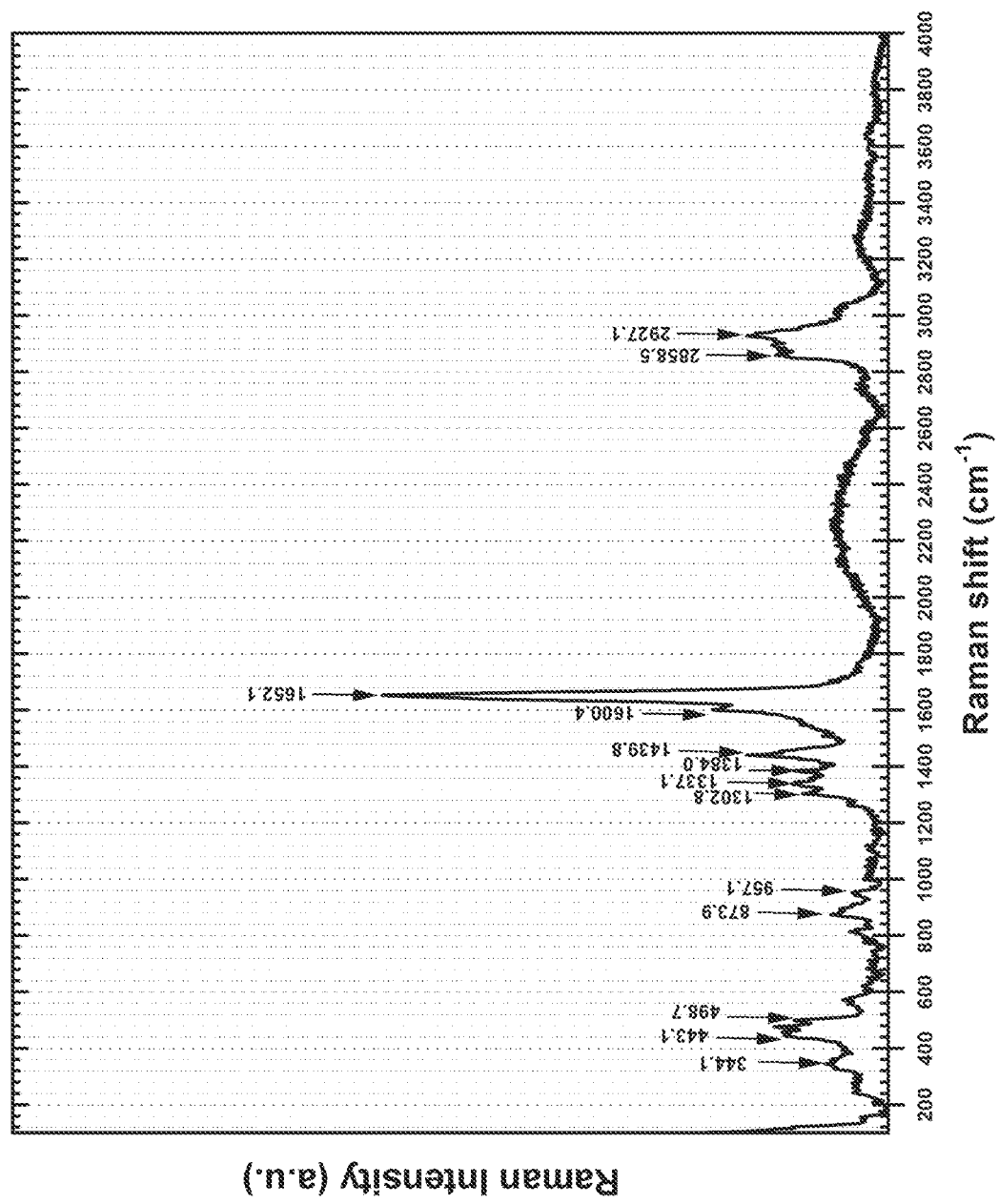
FIG. 1E shows FT-Raman spectrum of the Compound 1 calcium salt obtained as described in Example 1.

In some embodiments, the Compound 1 calcium salt exhibits an FT-Raman spectrum that is substantially the same as that depicted in FIG. 1E.

Figure 1F:
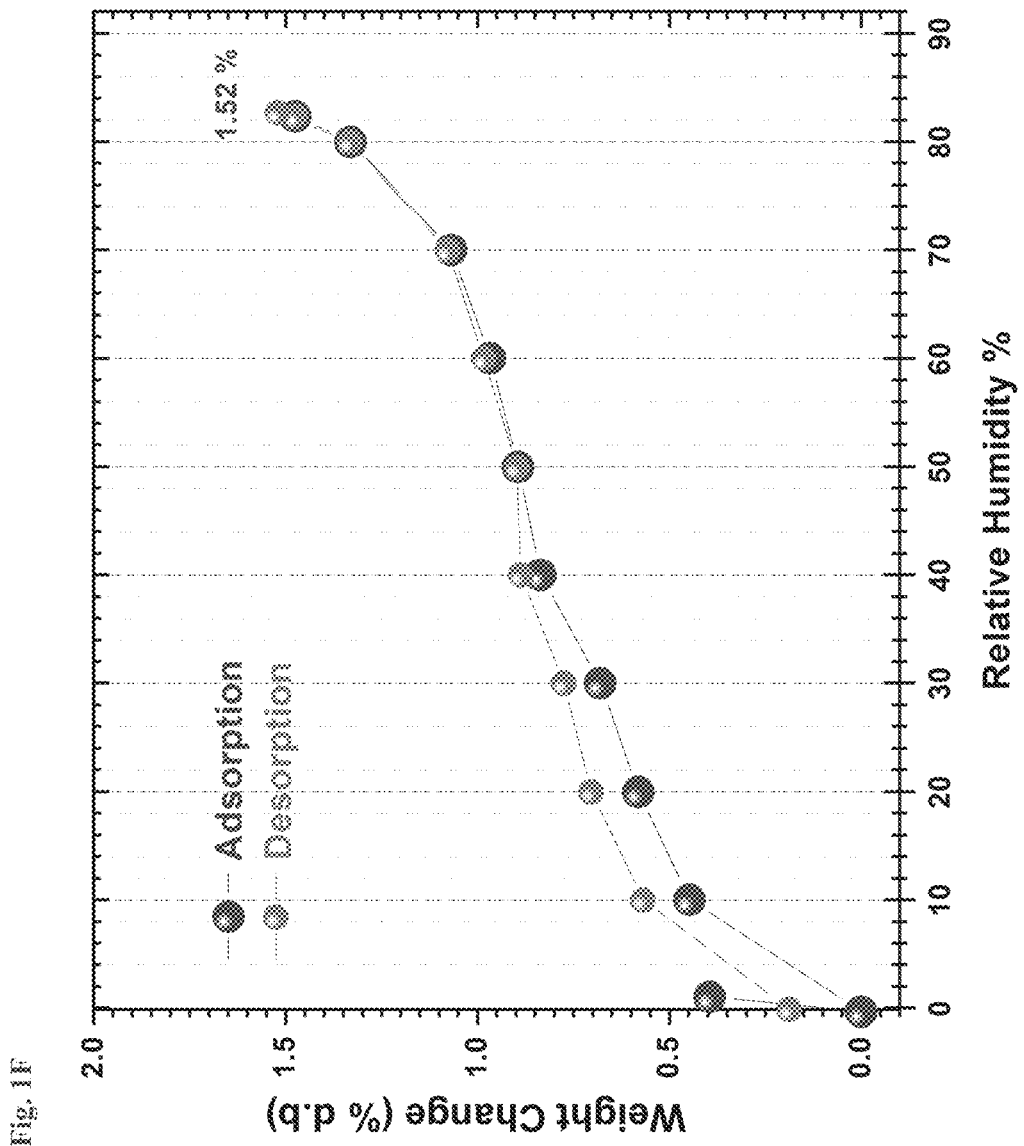
FIG. 1F shows a dynamic vapor sorption (DVS) spectrum of the Compound 1 calcium salt obtained as described in Example 1.

In some embodiments, the Compound 1 calcium salt exhibits a DVS spectrum that is substantially the same as that depicted in FIG. 1F.

Figure 1G:
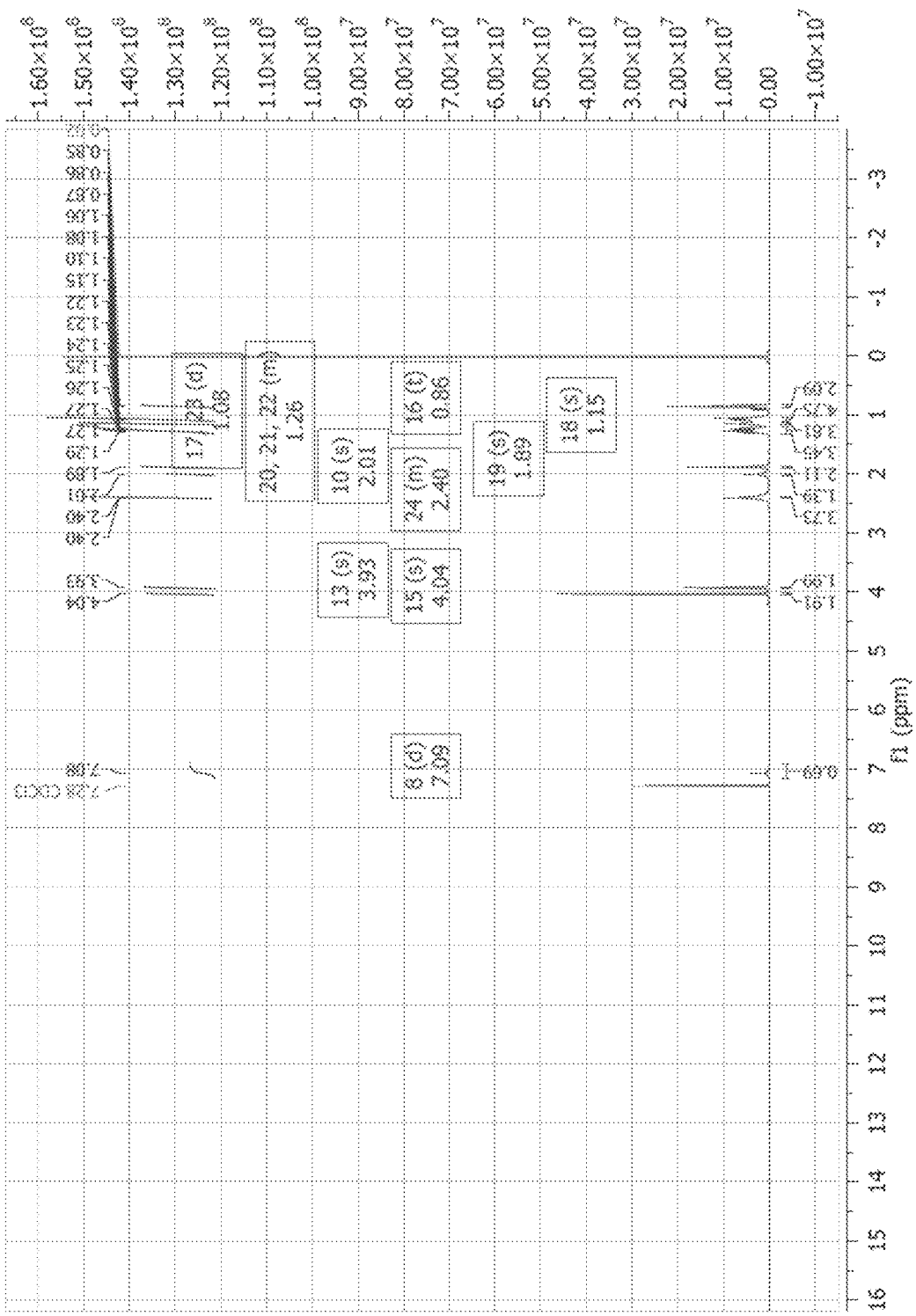
FIG. 1G shows a 1H NMR spectrum of the Compound 1 calcium salt obtained as described in Example 1.

In some embodiments, the Compound 1 calcium salt exhibits a 1H NMR spectrum that is substantially the same as that depicted in FIG. 1G.

In some embodiments, the Compound 1 calcium salt is a monohydrate.

In some embodiments, the Compound 1 calcium salt obtained according to Example 1 is a calcium salt monohydrate.

In some embodiments, the Compound 1 calcium salt obtained according to Example 1 is at least about 98% pure by weight. In some embodiments, the Compound 1 calcium salt obtained according to Example 1 is at least about 99% pure by weight.

In some embodiments, the Compound 1 calcium salt obtained according to Example 1 is at least about 98% pure by weight. In some embodiments, the Compound 1 calcium salt obtained according to Example 1 is at least about 99% pure by weight.

In some embodiments, the Compound 1 calcium salt obtained according to Example 1 is at least about 98% pure by weight after being exposed to 40° C./75% RH for 1 week. In some embodiments, the Compound 1 calcium salt obtained according to Example 1 is at least about 99% pure by weight after being exposed to 40° C./75% RH for 1 week.

In some embodiments, the Compound 1 calcium salt exhibits an X-ray powder diffraction (XRPD) pattern comprising a peak at 5.1±0.2 degrees 2-theta, a peak at 5.3±0.2 degrees 2-theta, and a peak at 10.1±0.2 degrees 2-theta. In some embodiments, the XRPD pattern further comprises a peak at a peak at 8.0±0.2 degrees 2-theta or a peak at 12.8±0.2 degrees 2-theta. In some embodiments, the XRPD pattern further comprises a peak at 13.3±0.2 degrees 2-theta, a peak at 17.9±0.2 degrees 2-theta, or a peak at 19.6±0.2 degrees 2-theta. In some embodiments, the XRPD pattern further comprises a peak at 14.6±0.2 degrees 2-theta or a peak at 18.5±0.2 degrees 2-theta.

In some embodiments, the Compound 1 calcium salt exhibits an XRPD pattern comprising a peak at 5.1±0.2 degrees 2-theta, a peak at 5.3±0.2 degrees 2-theta, and a peak at 10.1±0.2 degrees 2-theta, wherein the peak at 5.1±0.2 degrees 2-theta, the peak at 5.3±0.2 degrees 2-theta, and the peak at 10.1±0.2 degrees 2-theta have a relative peak intensity (%) of greater than 25%. In some embodiments, the XRPD pattern further comprises a peak at 8.0±0.2 degrees 2-theta or a peak at 12.8±0.2 degrees 2-theta, wherein the peak at 8.0±0.2 degrees 2-theta and the peak at 12.8±0.2 degrees 2-theta have a relative peak intensity (%) of greater than 10%. In some embodiments, the XRPD pattern further comprises a peak at 13.3±0.2 degrees 2-theta, a peak at 17.9±0.2 degrees 2-theta, or a peak at 19.6±0.2 degrees 2-theta, wherein the peak at 13.3±0.2 degrees 2-theta, the peak at 17.9±0.2 degrees 2-theta, and the peak at 19.6±0.2 degrees 2-theta have a relative peak intensity (%) of greater than 10%. In some embodiments, the XRPD pattern further comprises a peak at 14.6±0.2 degrees 2-theta or a peak at 18.5±0.2 degrees 2-theta, wherein the peak at 14.6±0.2 degrees 2-theta or the peak at 18.5±0.2 degrees 2-theta have a relative peak intensity (%) of greater than 8%.

In some embodiments, the Compound 1 calcium salt exhibits an XRPD pattern comprising a peak at 10.1±0.2 degrees 2-theta. In some embodiments, the Compound 1 calcium salt exhibits an XRPD pattern comprising a peak at 8.0±0.2 degrees 2-theta. In some embodiments, the Compound 1 calcium salt exhibits an XRPD pattern comprising a peak at 13.3±0.2 degrees 2-theta. In some embodiments, the Compound 1 calcium salt exhibits an XRPD pattern comprising a peak at 14.6±0.2 degrees 2-theta.

In some embodiments, the Compound 1 calcium salt exhibits an XRPD pattern comprising a peak at 8.0±0.2 degrees 2-theta and a peak at 10.1±0.2 degrees 2-theta. In some embodiments, the Compound 1 calcium salt exhibits an XRPD pattern comprising a peak at 10.1±0.2 degrees 2-theta and a peak at 14.6±0.2 degrees 2-theta. In some embodiments, the Compound 1 calcium salt exhibits an XRPD pattern comprising a peak at 8.0±0.2 degrees 2-theta, a peak at 10.1±0.2 degrees 2-theta, and a peak at 13.3±0.2 degrees 2-theta. In some embodiments, the Compound 1 calcium salt exhibits an XRPD pattern comprising a peak at 8.0±0.2 degrees 2-theta, a peak at 10.1±0.2 degrees 2-theta, and a peak at 14.6±0.2 degrees 2-theta. In some embodiments, the Compound 1 calcium salt exhibits an XRPD pattern comprising a peak at 8.0±0.2 degrees 2-theta, a peak at 10.1±0.2 degrees 2-theta, a peak at 13.3±0.2 degrees 2-theta, or a peak at 14.6±0.2 degrees 2-theta. In some embodiments, the Compound 1 calcium salt exhibits an XRPD pattern comprising a peak at 8.0±0.2 degrees 2-theta, a peak at 10.1±0.2 degrees 2-theta, a peak at 13.3±0.2 degrees 2-theta, and a peak at 14.6±0.2 degrees 2-theta.

In some embodiments, the Compound 1 calcium salt exhibits an XRPD pattern comprising a peak at 10.1±0.2 degrees 2-theta and 1 peak, 2 peaks, 3 peaks, 4 peaks, 5 peaks, 6 peaks, 7 peaks, 8 peaks, or 9 peaks of Table 3. In some embodiments, the Compound 1 calcium salt exhibits an XRPD pattern comprising a peak at 10.1±0.2 degrees 2-theta and 1 peak, 2 peaks, 3 peaks, 4 peaks, 5 peaks, 6 peaks, 7 peaks, 8 peaks, or 9 peaks of the following peaks: a peak at 5.1±0.2 degrees 2-theta, a peak at 5.3±0.2 degrees 2-theta, a peak at 7.9±0.2 degrees 2-theta, a peak at 12.8±0.2 degrees 2-theta, a peak at 13.3±0.2 degrees 2-theta, a peak at 14.6±0.2 degrees 2-theta, a peak at 17.9±0.2 degrees 2-theta, a peak at 18.5±0.2 degrees 2-theta, and a peak at 19.6±0.2 degrees 2-theta.

In some embodiments, the Compound 1 calcium salt exhibits an XRPD pattern comprising a peak from Table 3 having a relative peak intensity (%) of greater than 25%. In some embodiments, the Compound 1 calcium salt exhibits an XRPD pattern comprising a peak from Table 3 having a relative peak intensity (%) of greater than 15%. In some embodiments, the Compound 1 calcium salt exhibits an XRPD pattern comprising a peak from Table 3 having a relative peak intensity (%) of greater than 12%.

Figure 2B:
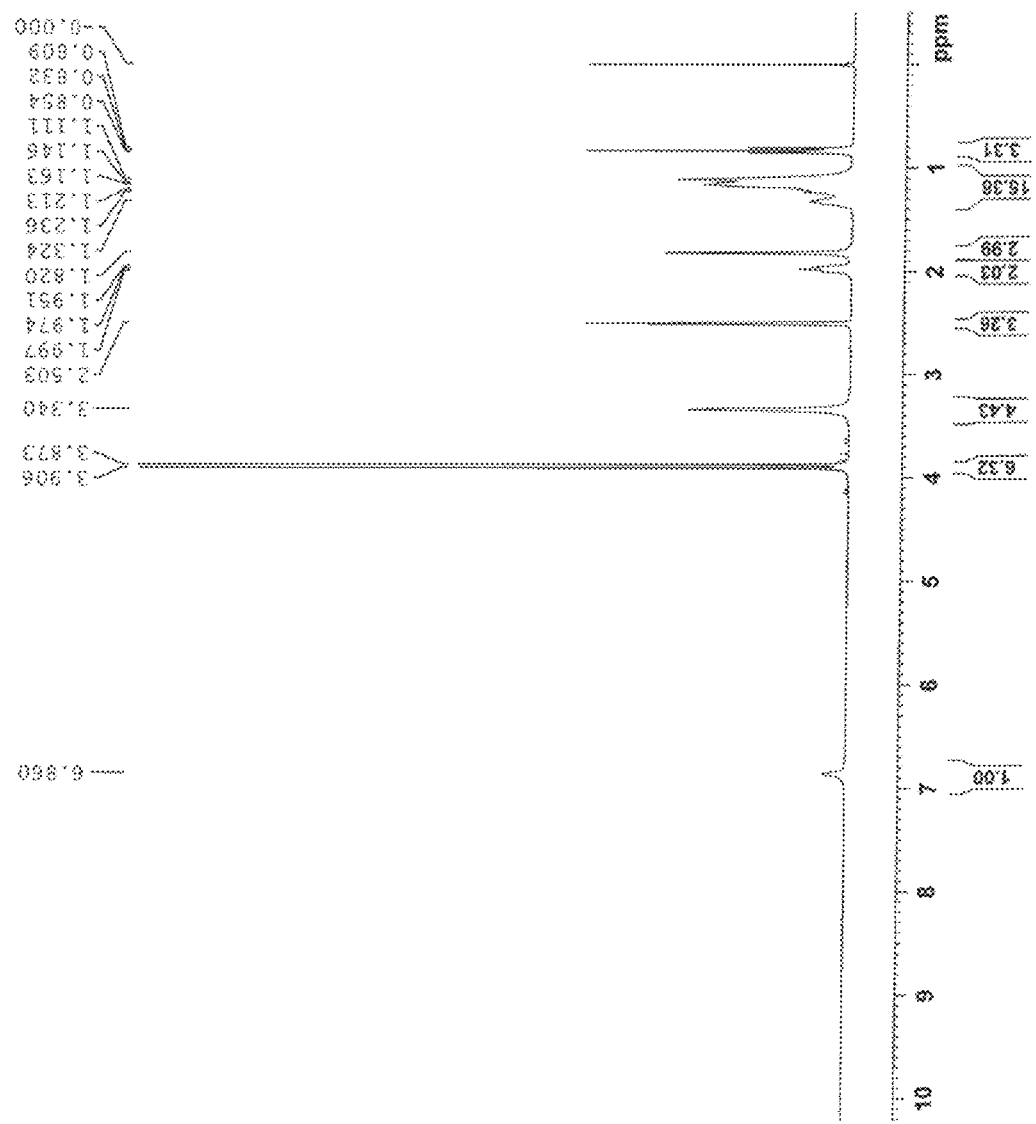
FIG. 2B shows a 1H NMR spectrum of the Compound 1 calcium salt obtained as described in Example 2.

In some embodiments, the Compound 1 calcium salt exhibits an XRPD pattern that is substantially the same as that depicted in FIG. 2A.

In some embodiments, the Compound 1 calcium salt exhibits a differential scanning calorimetry (DSC) thermogram comprising an endothermic peak having a peak maximum of from about 80° C. to about 105° C. In some embodiments, the Compound 1 calcium salt exhibits a DSC thermogram comprising an endothermic peak having a peak maximum of from about 90° C. to about 105° C. In some embodiments, the Compound 1 calcium salt exhibits a DSC thermogram comprising an endothermic peak having a peak maximum of from about 95° C. to about 105° C. In some embodiments, the Compound 1 calcium salt exhibits a DSC thermogram comprising an endothermic peak having a peak maximum of from about 98° C. to about 103° C. In some embodiments, the Compound 1 calcium salt exhibits a DSC thermogram comprising an endothermic peak having a peak maximum of about 101° C. In some embodiments, the Compound 1 calcium salt exhibits a DSC thermogram comprising an endothermic peak that onsets at about 77° C.

In some embodiments, the Compound 1 calcium salt exhibits a DSC thermogram comprising an exothermic peak having a peak maximum of from about 210° C. to about 216° C. In some embodiments, the Compound 1 calcium salt exhibits a DSC thermogram comprising an exothermic peak having a peak maximum of from about 212° C. to about 215° C. In some embodiments, the Compound 1 calcium salt exhibits a DSC thermogram comprising an exothermic peak having a peak maximum of from about 213° C. to about 215° C. In some embodiments, the Compound 1 calcium salt exhibits a DSC thermogram comprising an exothermic peak having a peak maximum at about 214° C. In some embodiments, the Compound 1 calcium salt exhibits a DSC thermogram comprising an exothermic peak that onsets at about 211° C.

Figure 2C:
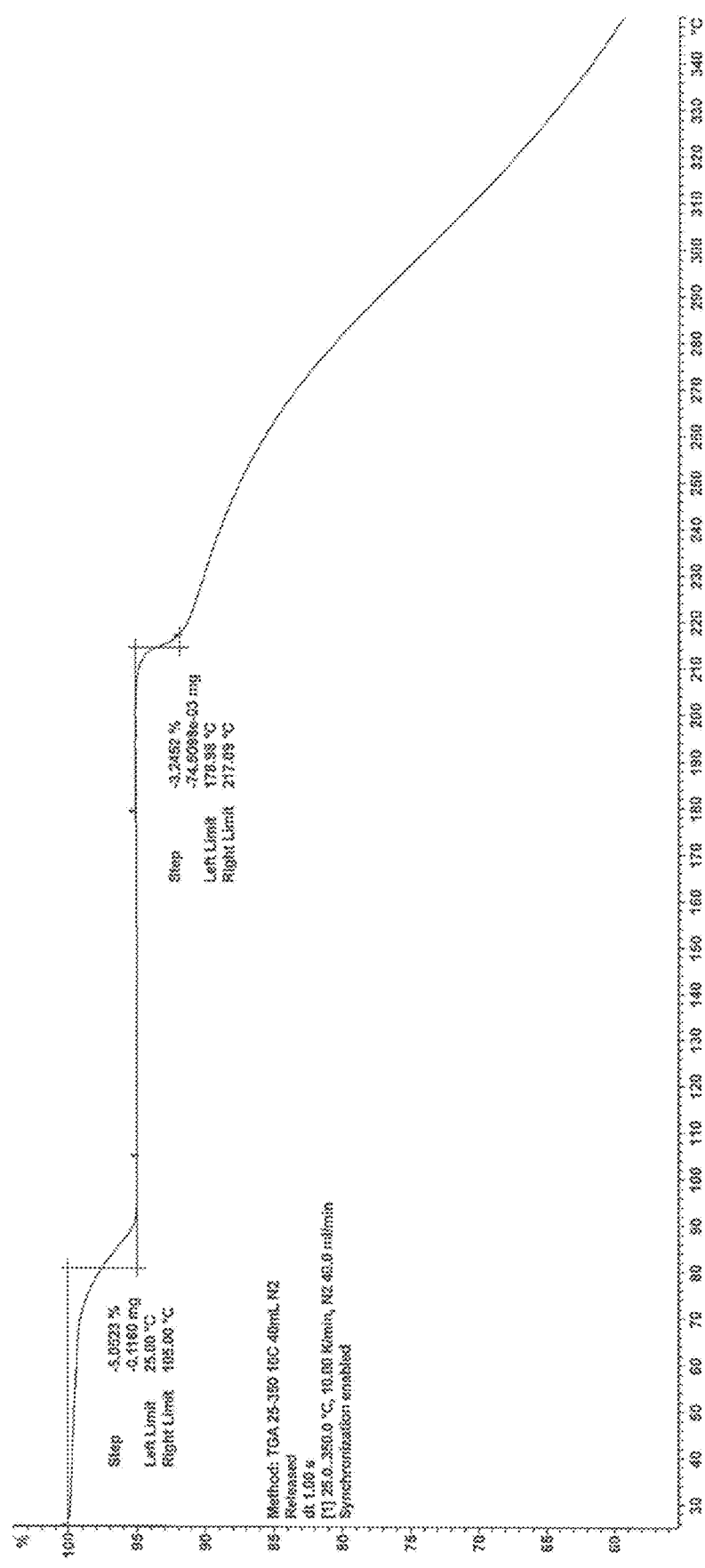
FIG. 2C shows a thermo-gravimetric (TG) thermogram of Compound 1 calcium salt obtained as described in Example 2.
Figure 2D:
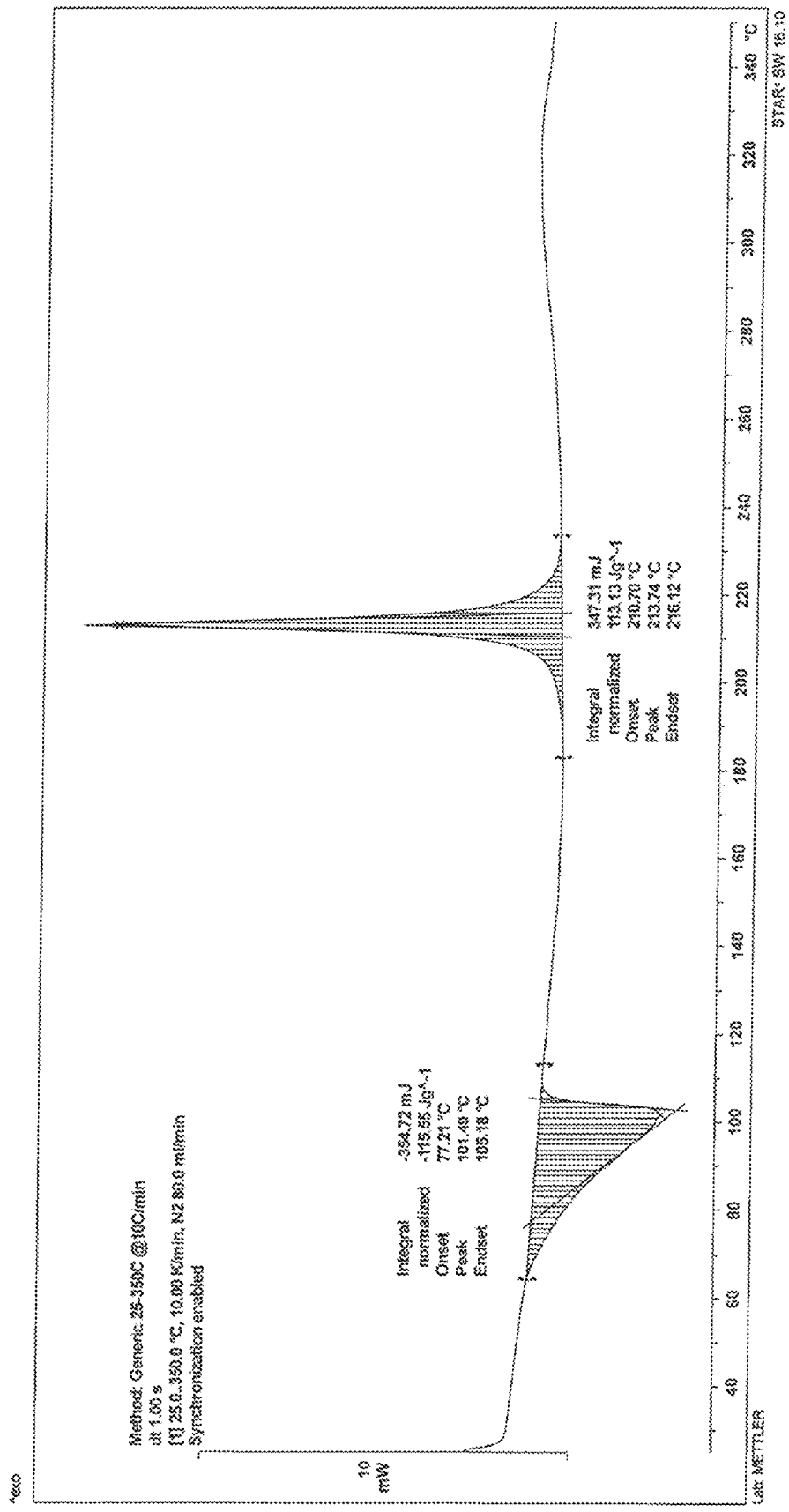
FIG. 2D shows a DSC thermogram of the Compound 1 calcium salt obtained as described in Example 2.

In some embodiments, the Compound 1 calcium salt exhibits a DSC thermogram that is substantially the same as that depicted in FIG. 2D.

In some embodiments, the Compound 1 calcium salt exhibits a thermo-gravimetric (TG) thermogram that is substantially the same as that depicted in FIG. 2C.

In some embodiments, the Compound 1 calcium salt obtained according to Example 2 is a monohydrate.

In some embodiments, the Compound 1 calcium salt obtained according to Example 2 is at least about 98% pure by weight. In some embodiments, the Compound 1 calcium salt obtained according to Example 2 is at least about 99% pure by weight.

In some embodiments, the Compound 1 calcium salt obtained according to Example 2 is at least about 98% pure by weight after being exposed to 40° C./75% RH for 1 week. In some embodiments, the Compound 1 calcium salt obtained according to Example 2 is at least about 99% pure by weight after being exposed to 40° C./75% RH for 1 week.

In some embodiments, the Compound 1 calcium salt has a solubility of about 500 µg/mL to about 600 µg/mL at pH 5 and 37° C., after 4 hours of being added to a pH 5 and 37° C. solution of Fed State Simulated Intestinal Fluid (FeSSIF) when determined by high-performance liquid chromatography (HPLC) at 236 nm or at 266 nm. In some embodiments, the Compound 1 calcium salt has a solubility of about 600 µg/mL to about 700 µg/mL at pH 5 and 37° C., after 24 hours of being added to a pH 5 and 37° C. solution of FeSSIF when determined by HPLC at 236 nm or at 266 nm.

In some embodiments, the Compound 1 calcium salt has a solubility of about 250 µg/mL to about 350 µg/mL at pH 5 and 25° C., after 4 hours of being added to a pH 5 and 25° C. solution of FeSSIF when determined by HPLC at 236 nm or at 266 nm. In some embodiments, the Compound 1 calcium salt has a solubility of about 250 µg/mL to about 350 µg/mL at pH 5 and 25° C., after 24 hours of being added to a pH 5 and 25° C. solution of FeSSIF when determined by HPLC at 236 nm or at 266 nm.

In some embodiments, the Compound 1 calcium salt has a solubility of about 350 µg/mL to about 450 µg/mL at pH 6.5 and 37° C., after 4 hours of being added to a pH 6.5 and 37° C. solution of Fasted State Simulated Intestinal Fluid (FaSSIF) when determined by HPLC at 236 nm or at 266 nm. In some embodiments, the Compound 1 calcium salt has a solubility of about 300 µg/mL to about 400 µg/mL at pH 6.5 and 37° C., after 24 hours of being added to a pH 6.5 and 37° C. solution of FaSSIF when determined by HPLC at 236 nm or at 266 nm.

In some embodiments, the Compound 1 calcium salt has a solubility of about 300 µg/mL to about 400 µg/mL at pH 6.5 and 25° C., after 4 hours of being added to a pH 6.5 and 25° C. solution of FaSSIF when determined by HPLC at 236 nm or at 266 nm. In some embodiments, the Compound 1 calcium salt has a solubility of about 200 µg/mL to about 300 µg/mL at pH 6.5 and 25° C., after 24 hours of being added to a pH 6.5 and 25° C. solution of FaSSIF when determined by HPLC at 236 nm or at 266 nm.

In some embodiments, the Compound 1 calcium salt is at least about 98% pure by weight, and the calcium salt comprises no more than about 2% of an impurity by weight of the calcium salt. In some embodiments, the Compound 1 calcium salt is about 95.0% to 100% pure by weight, and the calcium salt comprises 0% to about 5% of an impurity by weight of the calcium salt. In some embodiments, the Compound 1 calcium salt is about 98% to 100% pure by weight, and the calcium salt comprises 0% to about 2% of an impurity by weight of the calcium salt. In some embodiments, the Compound 1 calcium salt is about 98%, about 98.5%, about 99%, about 99.5%, or 100% pure by weight, and the calcium salt comprises about 2%, about 1.5%, about 1%, about 0.5%, or 0%, respectively, of an impurity by weight of the calcium salt. In some embodiments, the Compound 1 calcium salt is about 99.5%, about 99.9%, or about 99.95% pure by weight, and the calcium salt comprises about 0.5%, about 0.1%, or about 0.05%, respectively, of an impurity by weight of the calcium salt. In some embodiments, the purity or the impurity are determined by high-performance liquid chromatography (HPLC). In some embodiments, the purity or impurity is determined by HPLC at 236 nm. In some embodiments, the purity or impurity is determined by HPLC at 266 nm. In some embodiments, the purity or impurity is determined by titration.

In some embodiments, the Compound 1 calcium salt is at least about 98% pure by weight after being exposed to 40° C./75% RH for 1 week. In some embodiments, the Compound 1 calcium salt is at least about 99% pure by weight after being exposed to 40° C./75% RH for 1 week.

In some embodiments, the Compound 1 calcium salt is amorphous.

In some embodiments, the Compound 1 calcium salt is predominantly amorphous, wherein the predominantly amorphous calcium salt exhibits an XRPD pattern comprising a peak at 4.5±0.2 degrees 2-theta and a peak at 6.0±0.2 degrees 2-theta.

Figure 3A:
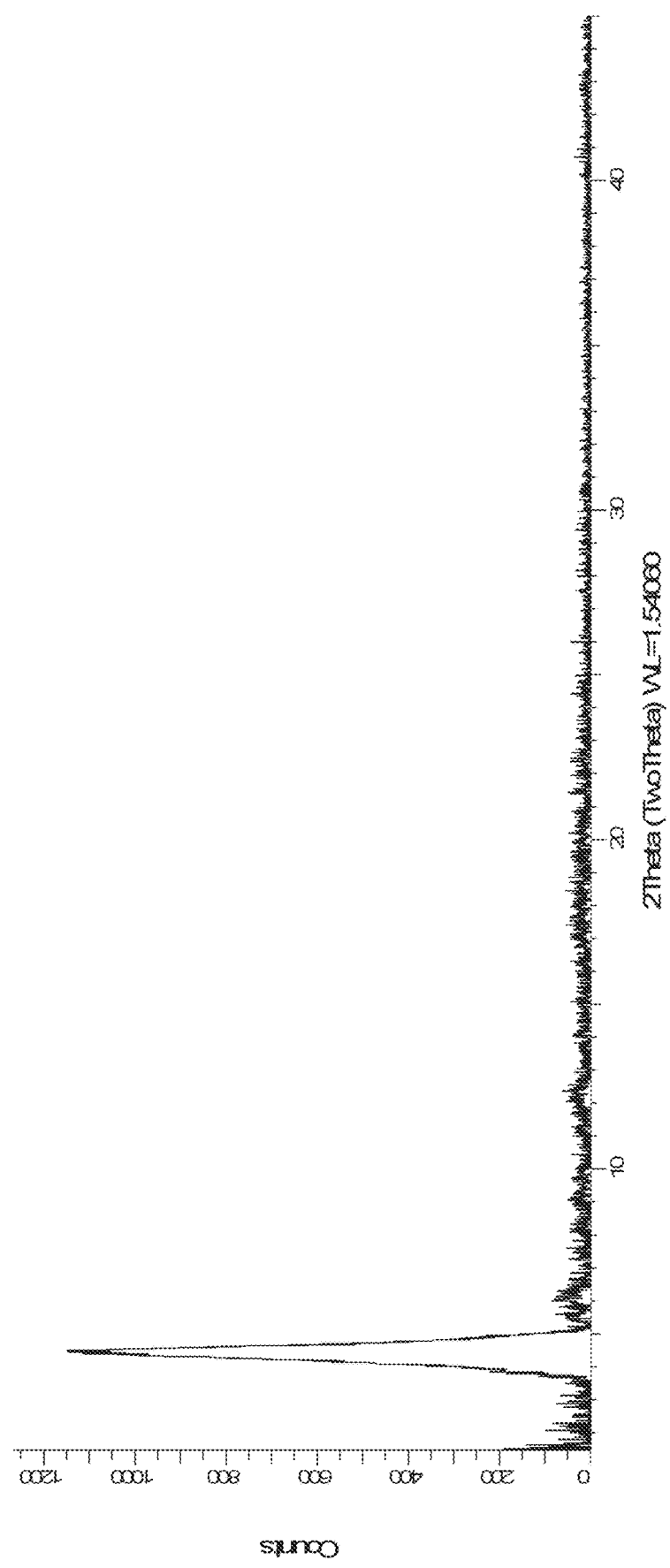
FIG. 3A shows an XRPD pattern of a Compound 1 calcium salt obtained as described in Example 3.

In some embodiments, the predominantly amorphous Compound 1 calcium salt exhibits an XRPD pattern that is predominantly the same as that depicted in FIG. 3A.

In some embodiments, the predominantly amorphous Compound 1 calcium salt is an anhydrate. In some embodiments, the predominantly amorphous Compound 1 calcium salt obtained according to Example 3 is a calcium salt anhydrate.

In some embodiments, the predominantly amorphous Compound 1 calcium salt obtained according to Example 3 is at least 50% amorphous by weight. In some embodiments, the predominantly amorphous Compound 1 calcium salt obtained according to Example 3 is at least 60% amorphous by weight. In some embodiments, the predominantly amorphous Compound 1 calcium salt obtained according to Example 3 is at least 70% amorphous by weight. In some embodiments, the predominantly amorphous Compound 1 calcium salt obtained according to Example 3 is at least 80% amorphous by weight. In some embodiments, the predominantly amorphous Compound 1 calcium salt obtained according to Example 3 is at least 90% amorphous by weight. In some embodiments, the predominantly amorphous Compound 1 calcium salt obtained according to Example 3 is at least 95% amorphous by weight. In some embodiments, the predominantly amorphous Compound 1 calcium salt obtained according to Example 3 is predominantly amorphous.

In some embodiments, the predominantly amorphous Compound 1 calcium salt is a calcium salt anhydrate.

In some embodiments, the compound of the invention is a Compound 1 L-arginine salt. In some embodiments, the Compound 1 L-arginine salt is crystalline.

In some embodiments, the Compound 1 L-arginine salt exhibits an X-ray powder diffraction (XRPD) pattern comprising a peak at 11.9±0.2 degrees 2-theta, a peak at 19.7±0.2 degrees 2-theta, and a peak at 20.2±0.2 degrees 2-theta. In some embodiments, the Compound 1 L-arginine salt exhibits an XRPD pattern comprising a peak at 11.9±0.2 degrees 2-theta, a peak at 19.7±0.2 degrees 2-theta, and a peak at 20.2±0.2 degrees 2-theta, wherein the peak at 20.2±0.2 degrees 2-theta is the most intense peak in the XRPD pattern. In some embodiments, the XRPD pattern further comprises a peak at 13.1±0.2 degrees 2-theta or a peak at 22.7±0.2 degrees 2-theta. In some embodiments, the XRPD pattern further comprises a peak at 10.4±0.2 degrees 2-theta, at 11.6±0.2 degrees 2-theta, or a peak at 21.7±0.2 degrees 2-theta. In some embodiments, the XRPD pattern further comprises a peak at 23.5±0.2 degrees 2-theta. In some embodiments, the XRPD pattern further comprises a peak at 3.9±0.2 degrees 2-theta or a peak at 19.3±0.2 degrees 2-theta. In some embodiments, the XRPD pattern further comprises a peak at 3.9±0.2 degrees 2-theta. In some embodiments, the XRPD pattern further comprises a peak at 12.8±0.2 degrees 2-theta or a peak at 18.3±0.2 degrees 2-theta. In some embodiments, the XRPD pattern further comprises a peak at 15.4±0.2 degrees 2-theta, a peak at 18.4±0.2 degrees 2-theta, a peak at 21.5±0.2 degrees 2-theta, and a peak at 23.5±0.2 degrees 2-theta.

In some embodiments, the Compound 1 L-arginine salt exhibits an XRPD pattern comprising 1 peak, 2 peaks, 3 peaks, 4 peaks, 5 peaks, 6 peaks, 7 peaks, 8 peaks, 9 peaks, or 10 peaks of Table 5A. In some embodiments, the Compound 1 L-arginine salt exhibits an XRPD pattern comprising 1 peak, 2 peaks, 3 peaks, 4 peaks, 5 peaks, 6 peaks, 7 peaks, 8 peaks, 9 peaks, or 10 peaks of the following peaks: a peak at 10.4±0.2 degrees 2-theta, a peak at 11.6±0.2 degrees 2-theta, a peak at 11.9±0.2 degrees 2-theta, a peak at 13.1±0.2 degrees 2-theta, a peak at 19.3±0.2 degrees 2-theta, a peak at 19.7±0.2 degrees 2-theta, a peak at 20.2±0.2 degrees 2-theta, a peak at 21.7±0.2 degrees 2-theta, a peak at 22.7±0.2 degrees 2-theta, and a peak at 23.5±0.2 degrees 2-theta.

In some embodiments, the Compound 1 L-arginine salt exhibits an XRPD pattern comprising a Table 5A peak having a relative peak intensity (%) of greater than 50%. In some embodiments, the Compound 1 L-arginine salt exhibits an XRPD pattern comprising a Table 5A peak having a relative peak intensity (%) of greater than 35%. In some embodiments, the Compound 1 L-arginine salt exhibits an XRPD pattern comprising a Table 5A peak having a relative peak intensity (%) of greater than 20%. In some embodiments, the Compound 1 L-arginine salt exhibits an XRPD pattern comprising a Table 5A peak having a relative peak intensity (%) of greater than 15%. In some embodiments, the Compound 1 L-arginine salt exhibits an XRPD pattern comprising a Table 5A peak having a relative peak intensity (%) of greater than 10%.

Figure 4A:
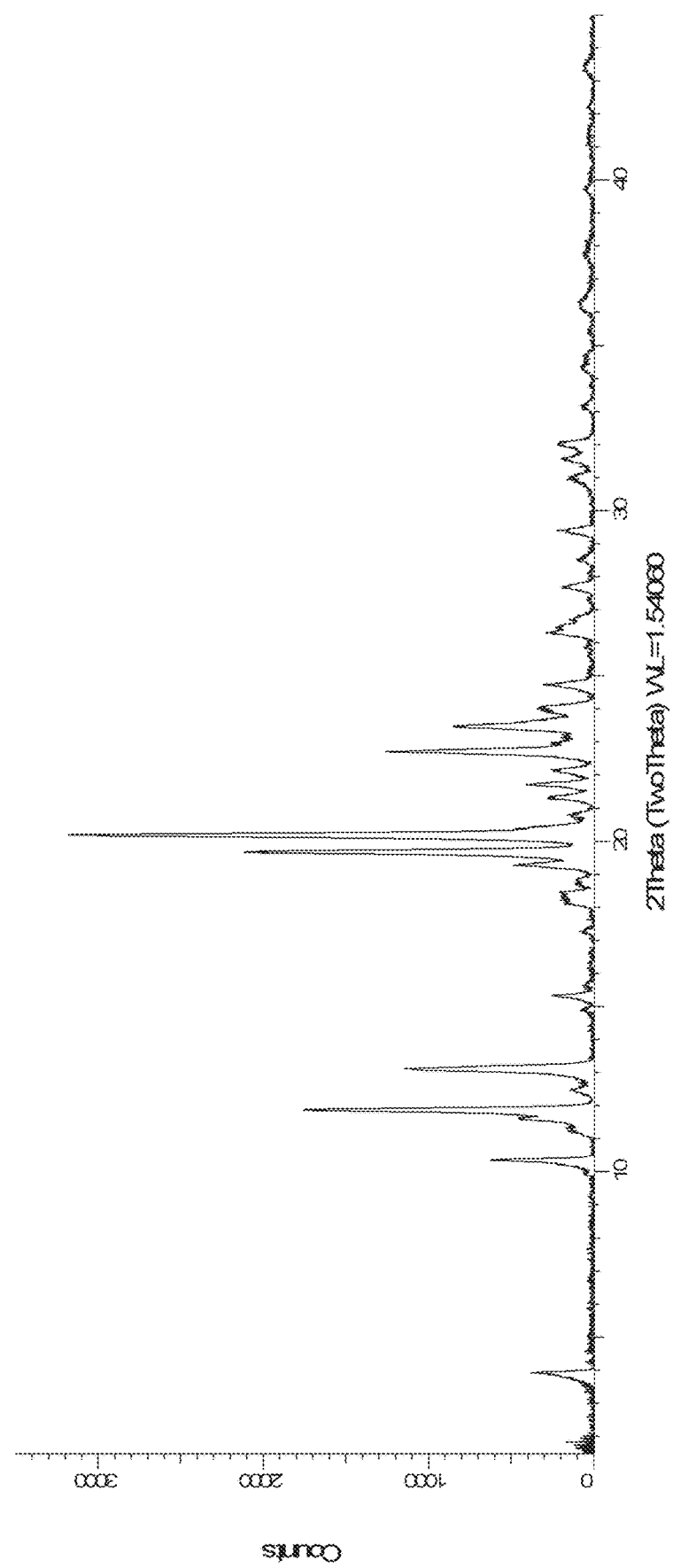
FIG. 4A shows an XRPD pattern of a Compound 1 L-arginine salt obtained as described in Procedure A of Example 4.

In some embodiments, the Compound 1 L-arginine salt exhibits an XRPD pattern that is substantially the same as that depicted in FIG. 4A.

In some embodiments, the Compound 1 L-arginine salt exhibits an X-ray powder diffraction (XRPD) pattern comprising a peak at 3.9±0.2 degrees 2-theta, a peak at 13.1±0.2 degrees 2-theta, and a peak at 20.3±0.2 degrees 2-theta. In some embodiments, the Compound 1 L-arginine salt exhibits an XRPD pattern comprising a peak at 3.9±0.2 degrees 2-theta, a peak at 13.1±0.2 degrees 2-theta, and a peak at 20.3±0.2 degrees 2-theta, wherein the peak at 3.9±0.2 degrees 2-theta is the most intense peak in the XRPD pattern. In some embodiments, the Compound 1 L-arginine salt exhibits an XRPD pattern further comprising a peak at 19.8±0.2 degrees 2-theta, 19.9±0.2 degrees 2-theta or a peak at 20.4±0.2 degrees 2-theta. In some embodiments, the Compound 1 L-arginine salt exhibits an XRPD pattern further comprising a peak at 10.4±0.2 degrees 2-theta, at 11.9±0.2 degrees 2-theta, or a peak at 20.4±0.2 degrees 2-theta.

In some embodiments, the Compound 1 L-arginine salt exhibits an XRPD pattern comprising 1 peak, 2 peaks, 3 peaks, 4 peaks, 5 peaks, 6 peaks, 7 peaks, 8 peaks, 9 peaks, or 10 peaks of Table 5B. In some embodiments, the Compound 1 L-arginine salt exhibits an XRPD pattern comprising 1 peak, 2 peaks, 3 peaks, 4 peaks, 5 peaks, 6 peaks, 7 peaks, 8 peaks, 9 peaks, or 10 peaks of the following peaks: a peak at 3.9±0.2 degrees 2-theta, a peak at 10.4±0.2 degrees 2-theta, a peak at 11.9±0.2 degrees 2-theta, a peak at 12.8±0.2 degrees 2-theta, a peak at 13.1±0.2 degrees 2-theta, a peak at 19.8±0.2 degrees 2-theta, a peak at 19.9±0.2 degrees 2-theta, a peak at 20.3±0.2 degrees 2-theta, a peak at 20.4±0.2 degrees 2-theta, and a peak at 21.7±0.2 degrees 2-theta. In some embodiments, the Compound 1 L-arginine salt exhibits an XRPD pattern comprising 1 peak, 2 peaks, 3 peaks, 4 peaks, 5 peaks, 6 peaks, 7 peaks, 8 peaks, 9 peaks, or 10 peaks of the following peaks: a peak at 10.4±0.2 degrees 2-theta, a peak at 11.7±0.2 degrees 2-theta, a peak at 11.9±0.2 degrees 2-theta, a peak at 13.1±0.2 degrees 2-theta, a peak at 19.8±0.2 degrees 2-theta, a peak at 19.9±0.2 degrees 2-theta, a peak at 20.3±0.2 degrees 2-theta, a peak at 20.4±0.2 degrees 2-theta, a peak at 21.7±0.2 degrees 2-theta, and a peak at 22.8±0.2 degrees 2-theta.

In some embodiments, the Compound 1 L-arginine salt exhibits an XRPD pattern comprising a Table 5B peak having a relative peak intensity (%) of greater than 65%. In some embodiments, the Compound 1 L-arginine salt exhibits an XRPD pattern comprising a Table 5B peak having a relative peak intensity (%) of greater than 60%. In some embodiments, the Compound 1 L-arginine salt exhibits an XRPD pattern comprising a Table 5B peak having a relative peak intensity (%) of greater than 50%. In some embodiments, the Compound 1 L-arginine salt exhibits an XRPD pattern comprising a Table 5B peak having a relative peak intensity (%) of greater than 40%. In some embodiments, the Compound 1 L-arginine salt exhibits an XRPD pattern comprising a Table 5B peak having a relative peak intensity (%) of greater than 30%.

Figure 4B:
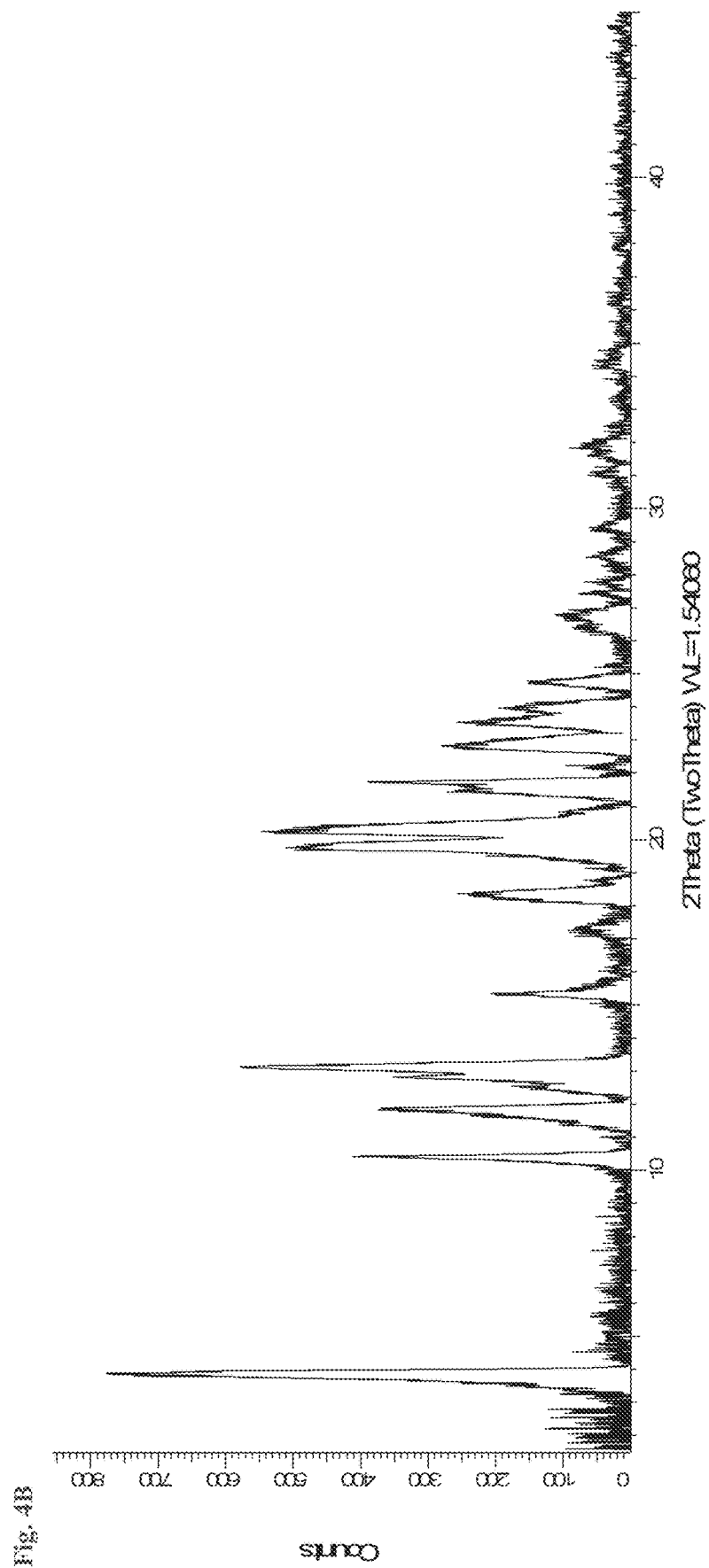
FIG. 4B shows an XRPD pattern of a Compound 1 L-arginine salt obtained as described in Procedure B of Example 4.

In some embodiments, the Compound 1 L-arginine salt exhibits an XRPD pattern that is substantially the same as that depicted in FIG. 4B.

In some embodiments, the Compound 1 L-arginine salt exhibits a differential scanning calorimetry (DSC) thermogram comprising an endothermic peak having a peak maximum of from about 58° C. to about 63° C. In some embodiments, the Compound 1 L-arginine salt exhibits a DSC thermogram comprising an endothermic peak having a peak maximum of from about 60° C. to about 62° C. In some embodiments, the Compound 1 L-arginine salt exhibits a DSC thermogram comprising an endothermic peak having a peak maximum of about 61° C. In some embodiments, the Compound 1 L-arginine salt exhibits a DSC thermogram comprising an endothermic peak that onsets at about 54° C. In some embodiments, the Compound 1 L-arginine salt exhibits a DSC thermogram comprising an endothermic peak that onsets at about 55° C.

In some embodiments, the Compound 1 L-arginine salt exhibits a DSC thermogram comprising an exothermic peak having a peak maximum of from about 148° C. to about 152° C. In some embodiments, the Compound 1 L-arginine salt exhibits a DSC thermogram comprising an exothermic peak having a peak maximum of from about 149° C. to about 151° C. In some embodiments, the Compound 1 L-arginine salt exhibits a DSC thermogram comprising an exothermic peak having a peak maximum of about 150° C. In some embodiments, the Compound 1 L-arginine salt exhibits a DSC thermogram comprising an exothermic peak that onsets at about 143° C. In some embodiments, the Compound 1 L-arginine salt exhibits a DSC thermogram comprising an exothermic peak that onsets at about 145° C.

Figure 4C:
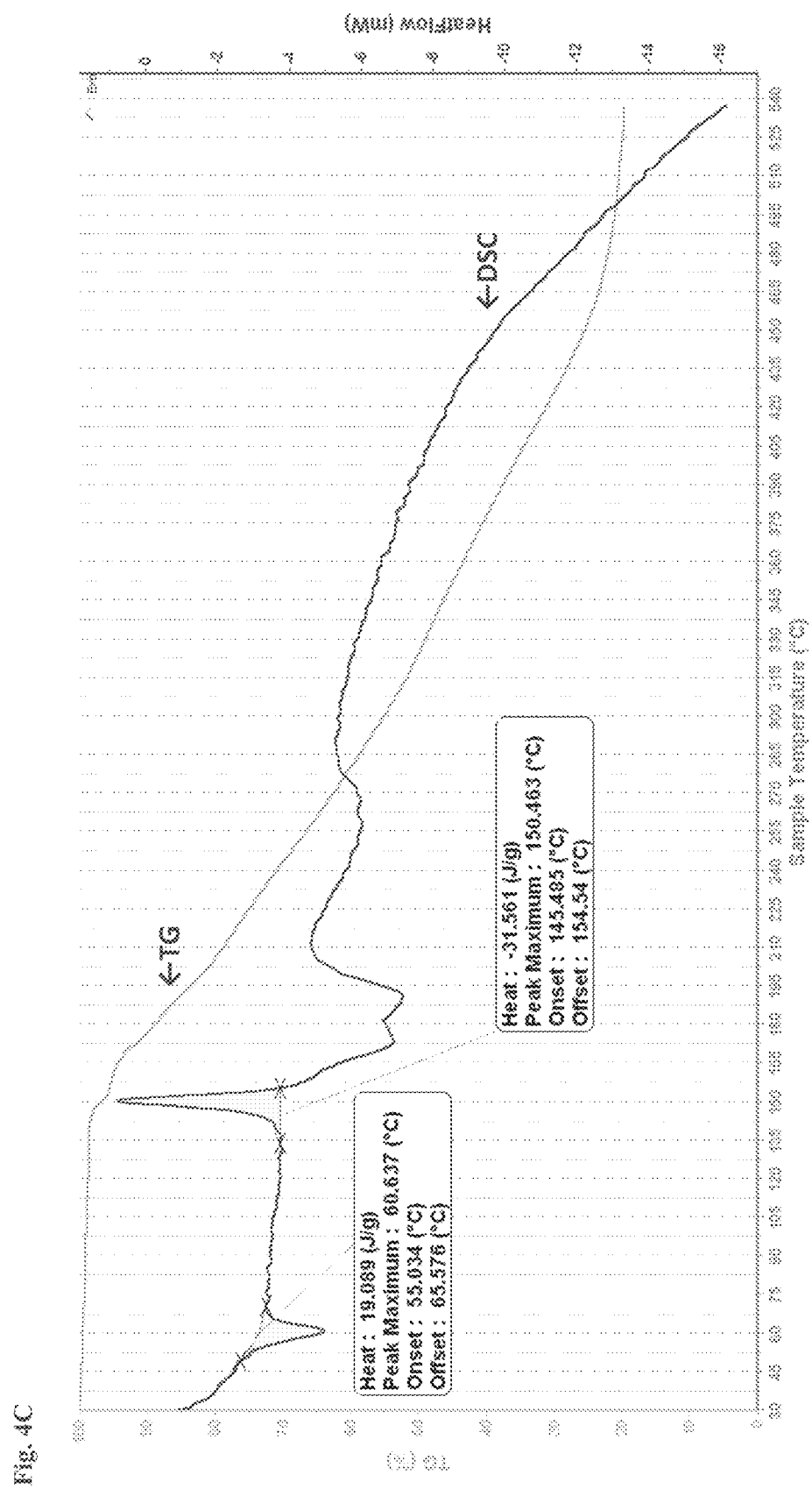
FIG. 4C shows an overlay of a TG thermogram and a DSC thermogram of the Compound 1 L-arginine salt obtained as described in Procedure A of Example 4.

In some embodiments, the Compound 1 L-arginine salt exhibits a DSC thermogram that is substantially the same as that depicted in FIG. 4C.

In some embodiments, the Compound 1 L-arginine salt exhibits a thermo-gravimetric (TG) thermogram that is substantially the same as that depicted in FIG. 4C.

In some embodiments, the Compound 1 L-arginine salt is anhydrous. In some embodiments, the Compound 1 L-arginine salt obtained according to Example 4, Procedure A, is an anhydrate. In some embodiments, the Compound 1 L-arginine salt obtained according to Example 4, Procedure B, is an anhydrate.

In some embodiments, the Compound 1 L-arginine salt is at least about 85% pure by weight. In some embodiments, the Compound 1 L-arginine salt is at least about 90% pure by weight. In some embodiments, the Compound 1 L-arginine salt is at least about 95% pure by weight. In some embodiments, the Compound 1 L-arginine salt is at least about 98% pure by weight. In some embodiments, the Compound 1 L-arginine salt is at least about 99% pure by weight. In some embodiments, the purity or impurity is determined by HPLC. In some embodiments, the purity or impurity is determined by HPLC at 236 nm. In some embodiments, the purity or impurity is determined by HPLC at 266 nm. In some embodiments, the purity or impurity is determined by titration.

In some embodiments, the Compound 1 L-arginine salt obtained according to Example 4, Procedure A, is at least about 85% pure by weight. In some embodiments, the Compound 1 L-arginine salt obtained according to Example 4, Procedure A, is at least about 90% pure by weight. In some embodiments, the Compound 1 L-arginine salt obtained according to Example 4, Procedure A, is at least about 95% pure by weight. In some embodiments, the Compound 1 L-arginine salt obtained according to Example 4, Procedure A, is at least about 98% pure by weight. In some embodiments, the Compound 1 L-arginine salt obtained according to Example 4, Procedure A, is at least about 99% pure by weight.

In some embodiments, the Compound 1 L-arginine salt obtained according to Example 4, Procedure B, is at least about 85% pure by weight. In some embodiments, the Compound 1 L-arginine salt obtained according to Example 4, Procedure B, is at least about 90% pure by weight. In some embodiments, the Compound 1 L-arginine salt obtained according to Example 4, Procedure B, is at least about 95% pure by weight. In some embodiments, the Compound 1 L-arginine salt obtained according to Example 4, Procedure B, is at least about 98% pure by weight. In some embodiments, the Compound 1 L-arginine salt obtained according to Example 4, Procedure B, is at least about 99% pure by weight.

In some embodiments, the compound of the invention is a Compound 1 phenylalanine salt.

In some embodiments, the Compound 1 phenylalanine salt is a racemic phenylalanine salt. In some embodiments, the Compound 1 phenylalanine salt is an L-phenylalanine salt.

In some embodiments, the Compound 1 phenylalanine salt is crystalline.

In some embodiments, the compound of the invention is a Compound 1 histidine salt.

In some embodiments, the Compound 1 histidine salt is a racemic histidine salt. In some embodiments, the Compound 1 histidine salt is an L-histidine salt.

In some embodiments, the Compound 1 histidine salt is crystalline.

In some embodiments, the Compound 1 salt comprises less than 5% of Compound 1 by weight of the salt. In some embodiments, the Compound 1 salt comprises less than 4% of Compound 1 by weight of the salt. In some embodiments, the Compound 1 salt comprises less than 3% of Compound 1 by weight of the salt. In some embodiments, the Compound 1 salt comprises less than 2% of Compound 1 by weight of the salt. In some embodiments, the Compound 1 salt comprises less than 1% of Compound 1 by weight of the salt.

In some embodiments, the Compound 1 salt is greater than 90% pure according to its HPLC chromatogram, based on the HPLC chromatogram's relative peak area. In some embodiments, the Compound 1 salt is greater than 95% pure according to its HPLC chromatogram, based on the HPLC chromatogram's relative peak area. In some embodiments, the Compound 1 salt is greater than 98% pure according to its HPLC chromatogram, based on the HPLC chromatogram's relative peak area. In some embodiments, the Compound 1 salt is greater than 90%, greater than 91%, greater than 92%, greater than 93%, greater than 94%, greater than 95%, greater than 96%, greater than 97%, greater than 98%, or greater than 99% pure according to its HPLC chromatogram, based on the HPLC chromatogram's relative peak area. In some embodiments, purity is determined according to HPLC at 236 nm. In some embodiments, purity is determined according to HPLC at 266 nm.

In some embodiments, the Compound 1 salt is stable at 25° C./60% RH for at least one week. In some embodiments, the Compound 1 salt is stable at 25° C./60% RH for at least one week, at least two weeks, at least three weeks, at least four weeks, at least 1 month, at least 2 months, at least 3 months, at least 4 months, at least 5 months, at least 6 months, at least 7 months, at least 8 months, at least 9 months, at least 10 months, at least 11 months, at least 12 months, at least 18 months, at least 24 months, at least 30 months, or at least 36 months. In some embodiments, 1 month is 28 days, 29 days, 30 days, or 31 days.

In some embodiments, the Compound 1 salt is stable at 40° C./75% RH for at least one week. In some embodiments, the Compound 1 salt is stable at 40° C./75% RH for at least one week, at least two weeks, at least three weeks, at least four weeks, at least 1 month, at least 2 months, at least 3 months, at least 4 months, at least 5 months, or at least 6 months. In some embodiments, 1 month is 28 days, 29 days, 30 days, or 31 days.

In some embodiments, the compound of the invention is a Compound 1 ester having the structure:

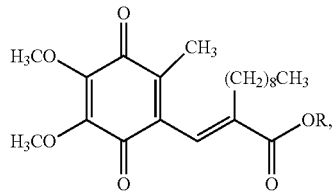

wherein R is $C_{10}$-$C_{24}$ hydrocarbyl.

In some embodiments of the ester of the invention, R is $C_{10}$-$C_{24}$ hydrocarbyl which can be saturated or unsaturated. In some embodiments of the ester of the invention, R is $C_{10}$-$C_{24}$ hydrocarbyl which can be linear or branched. In some embodiments of the ester of the invention, R is $C_{10}$-$C_{24}$ hydrocarbyl which can include a cyclic moiety.

In some embodiments of the ester of the invention, R is $C_{10}$-$C_{24}$ alkyl or $C_{10}$-$C_{24}$ alkenyl. In some embodiments, R is $C_{12}$-$C_{24}$ alkyl or $C_{12}$-$C_{24}$ alkenyl.

In some embodiments of the ester of the invention, R is

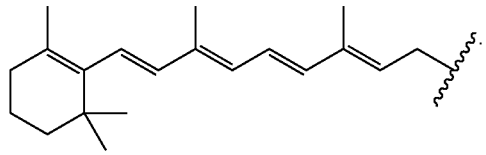 [SMILES: *C/C=C(C)/C=C/C=C(C)/C=C/C1=C(C)CCCC1(C)C]

In some embodiments, R is stearyl, palmitoyl, myristyl, lauryl, palmitoleyl, oleyl, linoleyl or linolenyl.

In some embodiments, the ester of the invention is crystalline.

In some embodiments, the ester of the invention comprises less than 5% of Compound 1 by weight of the ester. In some embodiments, the ester of the invention comprises less than 4% of Compound 1 by weight of the ester. In some embodiments, the ester of the invention comprises less than 3% of Compound 1 by weight of the ester. In some embodiments, the ester of the invention comprises less than 2% of Compound 1 by weight of the ester. In some embodiments, the ester of the invention comprises less than 1% of Compound 1 by weight of the ester.

In some embodiments, the compound of the invention is greater than 90% pure according to its HPLC chromatogram, based on the HPLC chromatogram's relative peak area. In some embodiments, the compound of the invention is greater than 95% pure according to its HPLC chromatogram, based on the HPLC chromatogram's relative peak area. In some embodiments, the compound of the invention is greater than 98% pure according to its HPLC chromatogram, based on the HPLC chromatogram's relative peak area. In some embodiments, the compound of the invention is greater than 90%, greater than 91%, greater than 92%, greater than 93%, greater than 94%, greater than 95%, greater than 96%, greater than 97%, greater than 98%, or greater than 99% pure according to an HPLC chromatogram, based on its HPLC chromatogram's relative peak area. In some embodiments, purity is determined according to a compound's HPLC chromatogram obtained at 236 nm. In some embodiments, purity is determined according to a compound's HPLC chromatogram obtained at 266 nm.

In some embodiments, the compound of the invention is stable at 25° C./60% RH for at least one week. In some embodiments, the compound of the invention is stable at 25° C./60% RH for at least about one week, at least about two weeks, at least about three weeks, at least about four weeks, at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about 18 months, at least about 24 months, at least about 30 months, or at least about 36 months.

In some embodiments, the compound of the invention is stable at 40° C./75% RH for at least about one week. In some embodiments, the compound of the invention is stable at 40° C./75% RH for at least about one week, at least about two weeks, at least about three weeks, at least about four weeks, at least about 1 month, at least about 2 months, at least about 3 months, at least about 4 months, at least about 5 months, or at least about 6 months.

In some embodiments, the compound of the invention is crystalline.

In some embodiments, the compound of the invention is a compound.

In some embodiments, the compound of invention is at least about 98% pure by weight, and a compound of the invention comprises no more than about 2% of an impurity by weight of the compound of the invention. In some embodiments, the compound of the invention is about 95.0% to 100% pure by weight, and the compound of the invention comprises 0% to about 5% of an impurity by weight of the compound of the invention. In some embodiments, the compound of the invention is about 98% to 100% pure by weight, and the compound of the invention comprises 0% to about 2% of an impurity by weight of the compound of the invention. In some embodiments, the compound of the invention is about 98%, about 98.5%, about 99%, about 99.5%, or 100% pure by weight, and the compound of the invention comprises about 2%, about 1.5%, about 1%, about 0.5%, or 0%, respectively, of an impurity by weight of the compound of the invention. In some embodiments, the compound of the invention is about 99.5%, about 99.9%, or about 99.95% pure by weight, and the compound of the invention comprises about 0.5%, about 0.1%, or about 0.05%, respectively, of an impurity by weight of the compound of the invention. In some embodiments, the compound of the invention is about 98%, about 98.5%, about 99%, about 99.5%, or 100% pure by weight, and the compound of the invention comprises about 2%, about 1.5%, about 1%, about 0.5%, or 0%, respectively, of an impurity by weight of the compound of the invention. In some embodiments, the compound of the invention is about 99.5%, about 99.9%, or about 99.95% pure by weight, and a compound of the invention comprises about 0.5%, about 0.1%, or about 0.05%, respectively, of an impurity by weight of the compound of the invention. In some embodiments, the compound of the invention is about 98%, about 98.5%, about 99%, about 99.5%, or 100% pure by weight, and the compound of the invention comprises about 2%, about 1.5%, about 1%, about 0.5%, or 0%, respectively, of an impurity by weight of the compound of the invention. In some embodiments, an impurity is determined by high-performance liquid chromatography (HPLC). In some embodiments, an impurity is determined according to a compound's HPLC chromatogram obtained at about 236 nm to about 266 nm. In some embodiments, an impurity is determined by titration.

In some embodiments, the compound of invention comprises less than about 1% of an impurity by weight of the compound of the invention. In some embodiments, the compound of invention comprises less than about 0.5% of an impurity by weight of the compound of the invention. In some embodiments, the compound of invention comprises less than about 1%, less than about 0.9%, less than about 0.8%, less than about 0.7%, less than about 0.6%, less than about 0.5%, less than about 0.4%, less than about 0.3%, or less than about 0.2% of an impurity by weight of the compound of the invention.

In some embodiments, the compound of invention is dried.

In some embodiments, the compound of invention is purified. In some embodiments, the compound of invention is isolated.

Methods

The present invention further provides methods for treating or preventing an ocular disease, comprising administering to a subject in need thereof an effective amount of: a compound of the invention; a composition of the invention; a compound of formula (I)

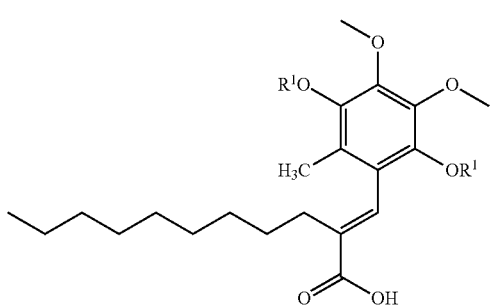

or a pharmaceutically acceptable salt thereof, wherein $R^1$ is each independently H, $C_1$-$C_6$ alkyl, or —C(O)($C_1$-$C_6$ alkyl); a compound of formula (II)

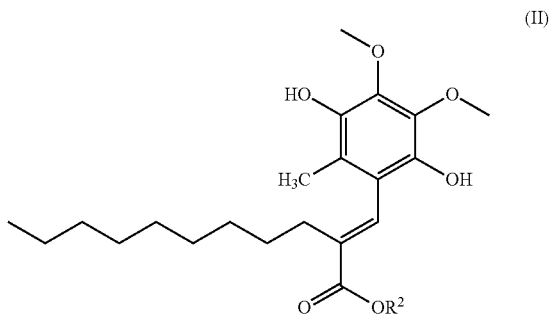

or a pharmaceutically acceptable salt thereof, wherein $R^2$ is $C_1$-$C_{24}$ hydrocarbyl group; a composition comprising a compound of formula (I) or a pharmaceutically acceptable salt thereof and a pharmaceutically acceptable carrier or vehicle; or a composition comprising a compound of formula (II) or a pharmaceutically acceptable salt thereof and a pharmaceutically acceptable carrier or vehicle.

In some embodiments, the ocular disease is diabetic retinal disease. In some embodiments, diabetic retinal disease is diabetic retinopathy (DR) or diabetic macular edema (DME). In some embodiments, the DR is moderately severe non-proliferative DR or mild proliferative DR. In some embodiments, the DME is DME without loss of central vision.

In some embodiments, the ocular disease is retinopathy of prematurity, DR, pathological myopia, hypertensive retinopathy, occlusive vasculitis, polypoidal choroidal vasculopathy, diabetic macular edema, uveitic macular edema, retinal vein occlusion, ocular neovascularization, ocular histoplasmosis, neovascular glaucoma, retinoblastoma, macular degeneration, retrolental fibroplasias, retinal angiomatous proliferation, dry eye disease, uveitis, thyroid eye disease, or sickle cell retinopathy. In some embodiments, the ocular disease is DR, and the DR is proliferative diabetic retinopathy. In some embodiments, the ocular disease is macular degeneration, and the macular degeneration is advanced macular degeneration. In some embodiments, the macular degeneration is wet age-related macular degeneration. In some embodiments, the macular degeneration is dry age-related macular degeneration. In some embodiments, the ocular disease is ocular neovascularization, and the ocular neovascularization is corneal neovascularization or retinal neovascularization. In some embodiments, retinal vein occlusion is central retinal vein occlusion or branch retinal vein occlusion.

The present invention further provides methods for treating diabetic retinopathy (DR), comprising administering to a subject in need thereof an effective amount of a Compound 1 calcium salt exhibiting an X-ray powder diffraction (XRPD) pattern comprising a peak at 5.8±0.2 degrees 2-theta and a peak at 6.3±0.2 degrees 2-theta.

The present invention further provides methods for treating diabetic retinopathy (DR), comprising administering to a subject in need thereof an effective amount of a Compound 1 calcium salt exhibiting an X-ray powder diffraction (XRPD) pattern comprising a peak at 4.1±0.2 degrees 2-theta, a peak at 5.3±0.2 degrees 2-theta, and a peak at 6.3±0.2 degrees 2-theta.

The present invention further provides methods for treating diabetic retinopathy (DR), comprising administering to a subject in need thereof an effective amount of a Compound 1 calcium salt exhibiting an X-ray powder diffraction (XRPD) pattern comprising a peak at 8.0±0.2 degrees 2-theta and a peak at 10.1±0.2 degrees 2-theta.

The present invention further provides methods for treating diabetic retinopathy (DR), comprising administering to a subject in need thereof an effective amount of a Compound 1 calcium salt exhibiting an X-ray powder diffraction (XRPD) pattern comprising a peak at 5.1±0.2 degrees 2-theta, a peak at 5.3±0.2 degrees 2-theta, and a peak at 10.1±0.2 degrees 2-theta.

The present invention further provides methods for treating diabetic macular edema (DME), comprising administering to a subject in need thereof an effective amount of a Compound 1 calcium salt exhibiting an X-ray powder diffraction (XRPD) pattern comprising a peak at 5.8±0.2 degrees 2-theta and a peak at 6.3±0.2 degrees 2-theta.

The present invention further provides methods for treating diabetic macular edema (DME), comprising administering to a subject in need thereof an effective amount of a Compound 1 calcium salt exhibiting an X-ray powder diffraction (XRPD) pattern comprising a peak at 4.1±0.2 degrees 2-theta, a peak at 5.3±0.2 degrees 2-theta, and a peak at 6.3±0.2 degrees 2-theta.

The present invention further provides methods for treating diabetic macular edema (DME), comprising administering to a subject in need thereof an effective amount of a Compound 1 calcium salt exhibiting an X-ray powder diffraction (XRPD) pattern comprising a peak at 8.0±0.2 degrees 2-theta and a peak at 10.1±0.2 degrees 2-theta.

The present invention further provides methods for treating diabetic macular edema (DME), comprising administering to a subject in need thereof an effective amount of a Compound 1 calcium salt exhibiting an X-ray powder diffraction (XRPD) pattern comprising a peak at 5.1±0.2 degrees 2-theta, a peak at 5.3±0.2 degrees 2-theta, and a peak at 10.1±0.2 degrees 2-theta.

The present invention further provides methods for treating or preventing geographic atrophy, choroidal neovascularization, or corneal graft rejection, comprising administering to a subject in need thereof an effective amount of a compound of the invention, a composition of the invention, a compound of formula (I) or a pharmaceutically acceptable salt thereof, a compound of formula (II) or a pharmaceutically acceptable salt thereof, a composition comprising a compound of formula (I) or a pharmaceutically acceptable salt thereof and a pharmaceutically acceptable carrier or vehicle, or a composition comprising a compound of formula (II) or a pharmaceutically acceptable salt thereof and a pharmaceutically acceptable carrier or vehicle.

The present invention further provides methods for treating or preventing Barrett's esophagus (BE), comprising administering to a subject in need thereof an effective amount of a compound of the invention, a composition of the invention, a compound of formula (I) or a pharmaceutically acceptable salt thereof, a compound of formula (II) or a pharmaceutically acceptable salt thereof, a composition comprising a compound of formula (I) or a pharmaceutically acceptable salt thereof and a pharmaceutically acceptable carrier or vehicle, or a composition comprising a compound of formula (II) or a pharmaceutically acceptable salt thereof and a pharmaceutically acceptable carrier or vehicle. In some embodiments, the BE is metaplastic BE.

The present invention further provides methods for treating or preventing cancer, cardiovascular disease, inflammation, chronic inflammatory disease, rheumatoid arthritis, idiopathic pulmonary fibrosis, acute adult respiratory distress syndrome, asthma, endometriosis, a keloid, systemic sclerosis, chemotherapy-induced peripheral neuropathy, stroke, gastro-intestinal dysfunction, chronic gastroesophageal reflux disease, von Hippel-Lindau syndrome, or a skin disorder, comprising administering to a subject in need thereof an effective amount of a compound of the invention, a composition of the invention, a compound of formula (I) or a pharmaceutically acceptable salt thereof, a compound of formula (II) or a pharmaceutically acceptable salt thereof, a composition comprising a compound of formula (I) or a pharmaceutically acceptable salt thereof and a pharmaceutically acceptable carrier or vehicle, or a composition comprising a compound of formula (II) or a pharmaceutically acceptable salt thereof and a pharmaceutically acceptable carrier or vehicle.

In some embodiments, the cancer is liver cancer, breast cancer, prostate cancer, pancreatic cancer, colon cancer, cervical cancer, germ cell tumor, adult glioma, pediatric glioma, osteosarcoma, rhabdomyosarcoma, non-small cell lung cancer, leukemia, or multiple myeloma. In some embodiments, the cancer is a solid tumor, a blood cancer, a leukemia, or a lymphoma. In some embodiments, the cancer is hepatocellular carcinoma (HCC). In some embodiments, the compound of the invention is useful for treating a solid tumor, comprising administering to a subject in need thereof an effective amount of a compound of the invention or a composition of the invention. In some embodiments, the cancer is not liver cancer. In some embodiments, the cancer is breast cancer, prostate cancer, pancreatic cancer, colon cancer, cervical cancer, germ cell tumor, adult glioma, pediatric glioma, osteosarcoma, rhabdomyosarcoma, non-small cell lung cancer, leukemia, or multiple myeloma.

In some embodiments, the cancer is a solid tumor, and the solid tumor is fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, a papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, retinoblastoma, or hepatocellular carcinoma (HCC).

In some embodiments, the cancer is blood cancer, and the blood cancer is leukemia, lymphoma, or myeloma. In some embodiments, the leukemia is acute lymphoblastic B-cell leukemia, acute lymphoblastic T-cell leukemia, acute myeloblastic leukemia, acute promyelocytic leukemia, acute monoblastic leukemia, acute erythroleukemic leukemia, acute megakaryoblastic leukemia, acute myelomonocytic leukemia, acute nonlymphocytic leukemia, acute undifferentiated leukemia, chronic myelocytic leukemia, chronic lymphocytic leukemia, or hairy cell leukemia. In some embodiments, the leukemia is an acute leukemia or a chronic leukemia. In some embodiments, the acute leukemia or the chronic leukemia is lymphoblastic leukemia, myelogenous leukemia, lymphocytic leukemia, or myelocytic leukemia. In some embodiments, the lymphoma is Hodgkin's disease, non-Hodgkin's lymphoma, Waldenström's macroglobulinemia, heavy chain disease, or polycythemia vera. In some embodiments, the myeloma is solitary plasmacytoma, extramedullary plasmacytoma or multiple myeloma.

In some embodiments, the cancer is ocular cancer. In certain embodiments, the cancer is a solid tumor. In certain embodiments, the cancer is a cancer due to human myeloid leukemia mononuclear cell line (THP-1). In certain embodiments, the cancer is an esophageal adenocarcinoma.

In some embodiments, the skin disorder is an inflammatory skin disorder. In some embodiments, the skin disorder is psoriasis, atopic dermatitis, or rosacea.

The present invention further provides methods for inhibiting angiogenesis, comprising administering to a subject in need thereof an effective amount of a compound of the invention, a composition of the invention, a compound of formula (I) or a pharmaceutically acceptable salt thereof, a compound of formula (II) or a pharmaceutically acceptable salt thereof, a composition comprising a compound of formula (I) or a pharmaceutically acceptable salt thereof and a pharmaceutically acceptable carrier or vehicle, or a composition comprising a compound of formula (II) or a pharmaceutically acceptable salt thereof and a pharmaceutically acceptable carrier or vehicle. In some embodiments, angiogenesis is ocular angiogenesis. In some embodiments, inhibiting angiogenesis results in slowing or stopping tumor growth. In some embodiments, inhibiting angiogenesis results in treating cancer.

The present invention further provides methods for inhibiting vascular endothelial growth factor (VEGF) or VEGF protein expression, comprising administering to a subject in need thereof an effective amount of a compound of the invention, a composition of the invention, a compound of formula (I) or a pharmaceutically acceptable salt thereof, a compound of formula (II) or a pharmaceutically acceptable salt thereof, a composition comprising a compound of formula (I) or a pharmaceutically acceptable salt thereof and a pharmaceutically acceptable carrier or vehicle, or a composition comprising a compound of formula (II) or a pharmaceutically acceptable salt thereof and a pharmaceutically acceptable carrier or vehicle. In some embodiments, inhibiting vascular endothelial growth factor (VEGF) or VEGF protein expression results in inhibiting angiogenesis. In some embodiments, angiogenesis is ocular angiogenesis. In some embodiments, inhibiting vascular endothelial growth factor (VEGF) or VEGF protein expression results in slowing or stopping tumor growth. In some embodiments, inhibiting vascular endothelial growth factor (VEGF) or VEGF protein expression results in treating cancer.

The present invention further provides methods for inhibiting capillary tube formation, comprising administering to a subject in need thereof an effective amount of a compound of the invention, a composition of the invention, a compound of formula (I) or a pharmaceutically acceptable salt thereof, a compound of formula (II) or a pharmaceutically acceptable salt thereof, a composition comprising a compound of formula (I) or a pharmaceutically acceptable salt thereof and a pharmaceutically acceptable carrier or vehicle, or a composition comprising a compound of formula (II) or a pharmaceutically acceptable salt thereof and a pharmaceutically acceptable carrier or vehicle.

The present invention further provides methods for treating or preventing a hepatic disease, comprising administering to a subject in need thereof an effective amount of a compound of the invention or a composition of the invention. In some embodiments, the hepatic disease is hepatitis, toxic hepatopathy, jaundice, cirrhosis, nonalcoholic steatohepatitis (NASH), nonalcoholic fatty liver disease (NAFLD), or alcoholic steatosis. In some embodiments, the hepatic disease is hepatitis, and the hepatitis is chronic hepatitis, acute hepatitis, viral hepatitis, or alcoholic hepatitis.

The present invention further provides methods for suppressing neuronal sensitivity, comprising administering to a subject in need thereof an effective amount of a compound of the invention, a composition of the invention, a compound of formula (I) or a pharmaceutically acceptable salt thereof, a compound of formula (II) or a pharmaceutically acceptable salt thereof, a composition comprising a compound of formula (I) or a pharmaceutically acceptable salt thereof and a pharmaceutically acceptable carrier or vehicle, or a composition comprising a compound of formula (II) or a pharmaceutically acceptable salt thereof and a pharmaceutically acceptable carrier or vehicle.

The present invention further provides methods for treating pain, comprising administering to a subject in need thereof an effective amount of a compound of the invention, a composition of the invention, a compound of formula (I) or a pharmaceutically acceptable salt thereof, a compound of formula (II) or a pharmaceutically acceptable salt thereof, a composition comprising a compound of formula (I) or a pharmaceutically acceptable salt thereof and a pharmaceutically acceptable carrier or vehicle, or a composition comprising a compound of formula (II) or a pharmaceutically acceptable salt thereof and a pharmaceutically acceptable carrier or vehicle. In some embodiments, the pain is inflammatory or chronic pain.

The present invention further provides methods for enhancing DNA base excision repair, comprising administering to a subject in need thereof an effective amount of a compound of the invention, a composition of the invention, a compound of formula (I) or a pharmaceutically acceptable salt thereof, a compound of formula (II) or a pharmaceutically acceptable salt thereof, a composition comprising a compound of formula (I) or a pharmaceutically acceptable salt thereof and a pharmaceutically acceptable carrier or vehicle, or a composition comprising a compound of formula (II) or a pharmaceutically acceptable salt thereof and a pharmaceutically acceptable carrier or vehicle.

The present invention further provides methods for enhancing neuronal DNA repair function, comprising administering to a subject in need thereof an effective amount of a compound of the invention, a composition of the invention, a compound of formula (I) or a pharmaceutically acceptable salt thereof, a compound of formula (II) or a pharmaceutically acceptable salt thereof, a composition comprising a compound of formula (I) or a pharmaceutically acceptable salt thereof and a pharmaceutically acceptable carrier or vehicle, or a composition comprising a compound of formula (II) or a pharmaceutically acceptable salt thereof and a pharmaceutically acceptable carrier or vehicle.

In some embodiments of the methods of the invention, the subject has obesity, diabetes, asthma, arthritis, chronic periodontitis, ulcerative colitis, Crohn's disease, chronic sinusitis, chronic active hepatitis, a chronic peptic ulcer, diverticulitis, fibromyalgia, irritable bowel syndrome, irritable bowel disease, Alzheimer's disease, Parkinson's disease, atherosclerosis, or tuberculosis. In some embodiments, the subject has diabetes.

In some embodiments, $R^1$ is each H in the compounds of formula (II) or a pharmaceutically acceptable salt thereof. In some embodiments, $R^1$ is each methyl. In some embodiments, $R^1$ is each —C(O)CH$_3$.

In some embodiments, $R^1$ is each independently $C_1$-$C_6$ alkyl or —C(O)($C_1$-$C_6$ alkyl) in the compounds of formula (I) or a pharmaceutically acceptable salt thereof.

In some embodiments, $R^2$ is $C_1$-$C_{10}$ alkyl in the compounds of formula (II) or a pharmaceutically acceptable salt thereof. In some embodiments, $R^2$ is $C_1$-$C_8$ alkyl in the compounds of formula (II) or a pharmaceutically acceptable salt thereof. In some embodiments, $R^2$ is $C_1$-$C_6$ alkyl in the compounds of formula (II) or a pharmaceutically acceptable salt thereof.

In some embodiments, $R^2$ is $C_{10}$-$C_{24}$ alkyl in the compounds of formula (II) or a pharmaceutically acceptable salt thereof. In some embodiments, $R^2$ is $C_{12}$-$C_{20}$ alkyl in the compounds of formula (II) or a pharmaceutically acceptable salt thereof. In some embodiments, $R^2$ is $C_{12}$-$C_{18}$ alkyl in the compounds of formula (II) or a pharmaceutically acceptable salt thereof.

The $R^2$ $C_{10}$-$C_{24}$ hydrocarbyl can be saturated or unsaturated in the compounds of formula (II) or pharmaceutically acceptable salts thereof. The $R^2$ $C_{10}$-$C_{24}$ hydrocarbyl can be linear or branched. In some embodiments, the $C_{10}$-$C_{24}$ hydrocarbyl includes a cyclic moiety.

The $R^2$ $C_{12}$-$C_{24}$ hydrocarbyl can be saturated or unsaturated in the compounds of formula (II) or pharmaceutically acceptable salts thereof. The $R^2$ $C_{12}$-$C_{24}$ hydrocarbyl can be linear or branched. In some embodiments, the $C_{12}$-$C_{24}$ hydrocarbyl includes a cyclic moiety.

In some embodiments, $R^2$ is $C_1$-$C_{10}$ alkyl in the compounds of formula (II) or a pharmaceutically acceptable salt thereof. In some embodiments, $R^2$ is $C_1$-$C_6$ alkyl. In some embodiments, $R^2$ is $C_1$-$C_4$ alkyl. In some embodiments, $R^2$ is methyl, ethyl, n-propyl, iso-propyl, n-butyl, sec-butyl, or tert-butyl. In some embodiments, $R^2$ is methyl, ethyl, or tert-butyl.

The $R^2$ $C_{10}$-$C_{24}$ hydrocarbyl can be $C_1$-$C_{24}$ alkyl or $C_2$-$C_{24}$ alkenyl in the compounds of formula (II) or pharmaceutically acceptable salts thereof. The $R^2$ $C_{10}$-$C_{24}$ hydrocarbyl can be $C_{10}$-$C_{24}$ alkyl or $C_{10}$-$C_{24}$ alkenyl in the compounds of formula (II) or pharmaceutically acceptable salts thereof.

In some embodiments, $R^2$ is

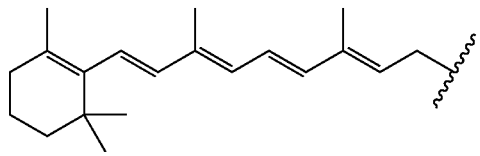 [SMILES: *C/C=C(C)/C=C/C=C(C)/C=C/C1=C(C)CCCC1(C)C]

in the compounds of formula (II) or a pharmaceutically acceptable salt thereof. In some embodiments, $R^2$ is stearyl, palmitoyl, myristyl, lauryl, palmitoleyl, oleyl, linoleyl or linolenyl.

In some embodiments, the salt of the compound of formula (I) or the compound of formula (II) is a calcium salt. In some embodiments, the salt of the compound of formula (I) or the compound of formula (II) is a L-arginine salt. In some embodiments, the salt of the compound of formula (I) or the compound of formula (II) is a phenylalanine salt. In some embodiments, the salt of the compound of formula (I) or the compound of formula (II) is a histidine salt.

In some embodiments, the administering is topically instilling into an eye of the subject.

In some embodiments, the administering is orally administering. In some embodiments, the administering is orally administering a composition that is in an oral dosage, for example, a tablet or a capsule, form.

In some embodiments, the effective amount is an amount per day that is or can be administered to a subject.

In some embodiments, the effective amount of the compound is about 0.01 mg to about 100 mg per day. In some embodiments, the effective amount of the compound is about 0.05 mg to about 50 mg per day. In some embodiments, the effective amount of the compound is about 0.1 mg to about 100 mg per day. In some embodiments, the effective amount of the compound is about 1 mg to about 25 mg per day. In some embodiments, the effective amount of the compound is about 5 mg to about 10 mg per day.

In some embodiments, the effective amount of the compound is molar equivalent to about 10 mg to about 1000 mg of Compound 1 (378.48 g/mol) per day. In some embodiments, the effective amount of the compound is molar equivalent to about 10 mg to about 800 mg of Compound 1 per day. In some embodiments, the effective amount of the compound is molar equivalent to about 10 mg to about 650 mg of Compound 1 per day. In some embodiments, the effective amount of the compound is molar equivalent to about 120 mg to about 600 mg of Compound 1 per day. In some embodiments, the effective amount of the compound is molar equivalent to about 10 mg, about 20 mg, about 30 mg, about 50 mg, about 60 mg, about 100 mg, about 120 mg, about 150 mg, about 180 mg, about 200 mg, about 240 mg, about 250 mg, about 300 mg, about 350 mg, about 360 mg, about 400 mg, about 420 mg, about 450 mg, about 480 mg, about 500 mg, about 540 mg, about 550 mg, about 600 mg, or about 650 mg of Compound 1 per day.

In some embodiments, the effective amount of Compound 1 calcium salt is about 10 mg, about 20 mg, about 30 mg, about 50 mg, about 60 mg, about 100 mg, about 120 mg, about 150 mg, about 180 mg, about 200 mg, about 240 mg, about 250 mg, about 300 mg, about 350 mg, about 360 mg, about 400 mg, about 420 mg, about 450 mg, about 480 mg, about 500 mg, about 540 mg, about 550 mg, about 600 mg, or about 650 mg per day.

In some embodiments, the effective amount of Compound 1 L-arginine salt is about 10 mg, about 20 mg, about 30 mg, about 50 mg, about 60 mg, about 100 mg, about 120 mg, about 150 mg, about 180 mg, about 200 mg, about 240 mg, about 250 mg, about 300 mg, about 350 mg, about 360 mg, about 400 mg, about 420 mg, about 450 mg, about 480 mg, about 500 mg, about 540 mg, about 550 mg, about 600 mg, or about 650 mg per day.

In some embodiments, the effective amount of Compound 1 L-phenylalanine salt is about 10 mg, about 20 mg, about 30 mg, about 50 mg, about 60 mg, about 100 mg, about 120 mg, about 150 mg, about 180 mg, about 200 mg, about 240 mg, about 250 mg, about 300 mg, about 350 mg, about 360 mg, about 400 mg, about 420 mg, about 450 mg, about 480 mg, about 500 mg, about 540 mg, about 550 mg, about 600 mg, or about 650 mg per day.

In some embodiments, the effective amount of Compound 1 L-histidine salt is about 10 mg, about 20 mg, about 30 mg, about 50 mg, about 60 mg, about 100 mg, about 120 mg, about 150 mg, about 180 mg, about 200 mg, about 240 mg, about 250 mg, about 300 mg, about 350 mg, about 360 mg, about 400 mg, about 420 mg, about 450 mg, about 480 mg, about 500 mg, about 540 mg, about 550 mg, about 600 mg, or about 650 mg per day.

In some embodiments, the effective amount of a compound of formula (I) or formula (II), or a pharmaceutically acceptable salt thereof is about 10 mg, about 20 mg, about 30 mg, about 50 mg, about 60 mg, about 100 mg, about 120 mg, about 150 mg, about 180 mg, about 200 mg, about 240 mg, about 250 mg, about 300 mg, about 350 mg, about 360 mg, about 400 mg, about 420 mg, about 450 mg, about 480 mg, about 500 mg, about 540 mg, about 550 mg, about 600 mg, or about 650 mg per day.

In some embodiments, the effective amount of the compound is molar equivalent to about 120 mg to about 600 mg of Compound 1 per day. In some embodiments, the effective amount of the compound is molar equivalent to about 600 mg of Compound 1 per day. In some embodiments, the effective amount of the compound is molar equivalent to about 480 mg of Compound 1 per day. In some embodiments, the effective amount of the compound is molar equivalent to about 360 mg of Compound 1 per day. In some embodiments, the effective amount of the compound is molar equivalent to about 300 mg of Compound 1 per day. In some embodiments, the effective amount of the compound is molar equivalent to about 240 mg of Compound 1 per day. In some embodiments, the effective amount of the compound is molar equivalent to about 120 mg of Compound 1 per day.

In some embodiments, the effective amount is a 600 mg (based on an amount that is molar equivalent to 600 mg of Compound 1) daily dose. In some embodiments, the daily dose is divisible among one or more oral dosage forms, e.g., tablets or capsules. In some embodiments, the daily dose is five, 120 mg (based on an amount that is molar equivalent to 120 mg of Compound 1) tablets. In some embodiments, the administering comprises administering to a subject three, 120 mg tablets in the morning and two, 120 mg tablets in the evening, where the 120 mg is based on an amount that is molar equivalent to 120 mg of Compound 1.

In some embodiments, the effective amount is a 300 mg (based on an amount that is molar equivalent to 300 mg of Compound 1) daily dose. In some embodiments, the daily dose is divisible among one or more oral dosage forms, e.g., tablets. In some embodiments, the daily dose is five, 60 mg tablets (based on an amount that is molar equivalent to 60 mg of Compound 1). In some embodiments, the administering comprises administering to a subject three, 60 mg tablets in the morning and two, 60 mg tablets in the evening, where the 60 mg is based on an amount that is molar equivalent to 60 mg of Compound 1.

In some embodiments, the effective amount of Compound 1 calcium salt is a 600 mg daily dose, based on an amount that is molar equivalent to 600 mg of Compound 1. In some embodiments, the daily dose is divisible among one or more oral dosage forms, e.g., tablets or capsules. In some embodiments, the daily dose is five, 120 mg tablets, based on an amount that is molar equivalent to 120 mg of Compound 1. In some embodiments, the administering comprises administering to a subject three, 120 mg tablets in the morning and two, 120 mg tablets in the evening, based on an amount that is molar equivalent to 120 mg of Compound 1.

In some embodiments, the effective amount of Compound 1 calcium salt is a 300 mg daily dose based on an amount that is molar equivalent to 300 mg of Compound 1. In some embodiments, the daily dose is divisible among one or more oral dosage forms, e.g., tablets. In some embodiments, the daily dose is five, 60 mg tablets based on an amount that is molar equivalent to 60 mg of Compound 1. In some embodiments, the administering comprises administering to a subject three, 60 mg tablets in the morning and two, 60 mg tablets in the evening, based on an amount that is molar equivalent to 60 mg of Compound 1.

In some embodiments, the effective amount of Compound 1 L-arginine salt is a 600 mg daily dose, based on an amount that is molar equivalent to 600 mg of Compound 1. In some embodiments, the daily dose is divisible among one or more oral dosage forms, e.g., tablets or capsules. In some embodiments, the daily dose is five, 120 mg tablets, based on an amount that is molar equivalent to 120 mg of Compound 1. In some embodiments, the administering comprises administering to a subject three, 120 mg tablets in the morning and two, 120 mg tablets in the evening, based on an amount that is molar equivalent to 120 mg of Compound 1.

In some embodiments, the effective amount of Compound 1 L-arginine salt is a 300 mg daily dose, based on an amount that is molar equivalent to 300 mg of Compound 1. In some embodiments, the daily dose is divisible among one or more oral dosage forms, e.g., tablets. In some embodiments, the daily dose is five, 60 mg tablets, based on an amount that is molar equivalent to 60 mg of Compound 1. In some embodiments, the administering comprises administering to a subject three, 60 mg tablets in the morning and two, 60 mg tablets in the evening, based on an amount that is molar equivalent to 60 mg of Compound 1.

In some embodiments, the effective amount of Compound 1 L-phenylalanine salt is a 600 mg daily dose based on an amount that is molar equivalent to 600 mg of Compound 1. In some embodiments, the daily dose is divisible among one or more oral dosage forms, e.g., tablets or capsules. In some embodiments, the daily dose is five, 120 mg tablets, based on an amount that is molar equivalent to 120 mg of Compound 1. In some embodiments, the administering comprises administering to a subject three, 120 mg tablets in the morning and two, 120 mg tablets in the evening, based on an amount that is molar equivalent to 120 mg of Compound 1.

In some embodiments, the effective amount of Compound 1 L-phenylalanine salt is a 300 mg daily dose based on an amount that is molar equivalent to 300 mg of Compound 1. In some embodiments, the daily dose is divisible among one or more oral dosage forms, e.g., tablets. In some embodiments, the daily dose is five, 60 mg tablets based on an amount that is molar equivalent to 60 mg of Compound 1. In some embodiments, the administering comprises administering to a subject three, 60 mg tablets in the morning and two, 60 mg tablets in the evening, based on an amount that is molar equivalent to 60 mg of Compound 1.

In some embodiments, the effective amount of Compound 1 L-histidine salt is a 600 mg daily dose, based on an amount that is molar equivalent to 600 mg of Compound 1. In some embodiments, the daily dose is divisible among one or more oral dosage forms, e.g., tablets or capsules. In some embodiments, the daily dose is five, 120 mg tablets, based on an amount that is molar equivalent to 120 mg of Compound 1. In some embodiments, the administering comprises administering to a subject three, 120 mg tablets in the morning and two, 120 mg tablets in the evening, based on an amount that is molar equivalent to 120 mg of Compound 1.

In some embodiments, the effective amount of Compound 1 L-histidine salt is a 300 mg daily dose based on an amount that is molar equivalent to 300 mg of Compound 1. In some embodiments, the daily dose is divisible among one or more oral dosage forms, e.g., tablets. In some embodiments, the daily dose is five, 60 mg tablets based on an amount that is molar equivalent to 60 mg of Compound 1. In some embodiments, the administering comprises administering to a subject three, 60 mg tablets in the morning and two, 60 mg tablets in the evening, based on an amount that is molar equivalent to 60 mg of Compound 1.

In some embodiments, the effective amount of a compound of formula (I) or formula (II), or a pharmaceutically acceptable salt thereof is a 600 mg daily dose, based on an amount that is molar equivalent to 600 mg of Compound 1. In some embodiments, the daily dose is divisible among one or more oral dosage forms, e.g., tablets or capsules. In some embodiments, the daily dose is five, 120 mg tablets, based on an amount that is molar equivalent to 120 mg of Compound 1. In some embodiments, the administering comprises administering to a subject three, 120 mg tablets in the morning and two, 120 mg tablets in the evening, based on an amount that is molar equivalent to 120 mg of Compound 1.

In some embodiments, the effective amount of a compound of formula (I) or formula (II), or a pharmaceutically acceptable salt thereof is a 300 mg daily dose, based on an amount that is molar equivalent to 300 mg of Compound 1. In some embodiments, the daily dose is divisible among one or more oral dosage forms, e.g., tablets. In some embodiments, the daily dose is five, 60 mg tablets, based on an amount that is molar equivalent to 60 mg of Compound 1. In some embodiments, the administering comprises administering to a subject three, 60 mg tablets in the morning and two, 60 mg tablets in the evening, based on an amount that is molar equivalent to 60 mg of Compound 1.

In some embodiments, the effective amount of the compound is a daily dose. In some embodiments, the effective amount of the compound is administered once a day, twice a day, or three times a day.

In some embodiments, the effective amount of the compound is administered in a single composition or multiple compositions. In some embodiments, the composition is a tablet or a capsule.

Compositions

In some embodiments, the compositions are formulated for administration by a variety of means including orally, parenterally, by inhalation spray, topically, or rectally.

In some embodiments, the compositions are in the form of a solution, a suspension, an emulsion, a tablet, a pill, a capsule, a powder, a cream, or a gel.

In some embodiments, the compositions are in the form of an ophthalmic solution, or the compositions are coated on or incorporated in an ophthalmic drug delivery device.

In some embodiments, the compositions are in the form of a tablet or capsule.

In some embodiments, the compositions comprise a compound invention in an amount that is molar equivalent to about 20 mg to about 600 mg of Compound 1 (378.48 g/mol). In some embodiments, the compositions of the invention comprise a compound disclosed herein in an amount that is molar equivalent to about 50 mg to about 600 mg of Compound 1. In some embodiments, the compositions comprise the compound in an amount that is molar equivalent to about 50 mg to about 400 mg of Compound 1. In some embodiments, the compositions comprise the compound in an amount that is molar equivalent to about 50 mg to about 200 mg of Compound 1. In some embodiments, the compositions comprise the compound in an amount that is molar equivalent to about 50 mg to about 150 mg of Compound 1.

In some embodiments, the compositions comprise the compound in an amount that is molar equivalent to about 50 mg, about 60 mg, about 70 mg, about 80 mg, about 90 mg, about 100 mg, about 110 mg, about 120 mg, about 130 mg, about 140 mg, or about 150 mg of Compound 1. In some embodiments, the compositions comprise the compound in an amount that is molar equivalent to about 60 mg or about 120 mg of Compound 1.

In some embodiments, the compositions comprise Compound 1 calcium salt that is molar equivalent to about 20 mg to about 600 mg of Compound 1. In some embodiments, the compositions comprise Compound 1 calcium salt that is molar equivalent to about 50 mg to about 600 mg of Compound 1. In some embodiments, the compositions comprise Compound 1 calcium salt that is molar equivalent to about 50 mg to about 400 mg of Compound 1. In some embodiments, the compositions comprise Compound 1 calcium salt that is molar equivalent to about 50 mg to about 200 mg of Compound 1. In some embodiments, the compositions comprise Compound 1 calcium salt that is molar equivalent to about 50 mg to about 150 mg of Compound 1.

In some embodiments, the compositions comprise Compound 1 calcium salt that is molar equivalent to about 50 mg, about 60 mg, about 70 mg, about 80 mg, about 90 mg, about 100 mg, about 110 mg, about 120 mg, about 130 mg, about 140 mg, or about 150 mg of Compound 1. In some embodiments, the compositions comprise Compound 1 calcium salt that is molar equivalent to about 60 mg or about 120 mg of Compound 1.

In some embodiments, the compositions comprise Compound 1 L-arginine salt that is molar equivalent to about 20 mg to about 600 mg of Compound 1. In some embodiments, the compositions comprise Compound 1 L-arginine salt that is molar equivalent to about 50 mg to about 600 mg of Compound 1. In some embodiments, the compositions comprise Compound 1 L-arginine salt that is molar equivalent to about 50 mg to about 400 mg of Compound 1. In some embodiments, the compositions comprise Compound 1 L-arginine salt that is molar equivalent to about 50 mg to about 200 mg of Compound 1. In some embodiments, the compositions comprise Compound 1 L-arginine salt that is molar equivalent to about 50 mg to about 150 mg of Compound 1.

In some embodiments, the compositions comprise Compound 1 L-arginine salt that is molar equivalent to about 50 mg, about 60 mg, about 70 mg, about 80 mg, about 90 mg, about 100 mg, about 110 mg, about 120 mg, about 130 mg, about 140 mg, or about 150 mg of Compound 1. In some embodiments, the compositions comprise Compound 1 L-arginine salt that is molar equivalent to about 60 mg or about 120 mg of Compound 1.

In some embodiments, the compositions comprise Compound 1 L-Phenylalanine Salt that is molar equivalent to about 20 mg to about 600 mg of Compound 1. In some embodiments, the compositions comprise Compound 1 L-phenylalanine salt that is molar equivalent to about 50 mg to about 600 mg of Compound 1. In some embodiments, the compositions comprise Compound 1 L-phenylalanine salt that is molar equivalent to about 50 mg to about 400 mg of Compound 1. In some embodiments, the compositions comprise Compound 1 L-phenylalanine salt that is molar equivalent to about 50 mg to about 200 mg of Compound 1. In some embodiments, the compositions comprise Compound 1 L-phenylalanine salt that is molar equivalent to about 50 mg to about 150 mg of Compound 1.

In some embodiments, the compositions comprise Compound 1 L-phenylalanine salt that is molar equivalent to about 50 mg, about 60 mg, about 70 mg, about 80 mg, about 90 mg, about 100 mg, about 110 mg, about 120 mg, about 130 mg, about 140 mg, or about 150 mg of Compound 1. In some embodiments, the compositions comprise Compound 1 L-phenylalanine salt that is molar equivalent to about 60 mg or about 120 mg of Compound 1.

In some embodiments, the compositions comprise Compound 1 L-histidine salt that is molar equivalent to about 20 mg to about 600 mg of Compound 1. In some embodiments, the compositions comprise Compound 1 L-histidine salt that is molar equivalent to about 50 mg to about 600 mg of Compound 1. In some embodiments, the compositions comprise Compound 1 L-histidine salt that is molar equivalent to about 50 mg to about 400 mg of Compound 1. In some embodiments, the compositions comprise Compound 1 L-histidine salt that is molar equivalent to about 50 mg to about 200 mg of Compound 1. In some embodiments, the compositions comprise Compound 1 L-histidine salt that is molar equivalent to about 50 mg to about 150 mg of Compound 1.

In some embodiments, the compositions comprise Compound 1 L-histidine salt that is molar equivalent to about 50 mg, about 60 mg, about 70 mg, about 80 mg, about 90 mg, about 100 mg, about 110 mg, about 120 mg, about 130 mg, about 140 mg, or about 150 mg of Compound 1. In some embodiments, the compositions comprise Compound 1 L-histidine salt that is molar equivalent to about 60 mg or about 120 mg of Compound 1.

In some embodiments, the compositions comprise a compound of formula (I) or formula (II), or a pharmaceutically acceptable salt thereof that is molar equivalent to about 20 mg to about 600 mg of Compound 1. In some embodiments, the compositions comprise a compound of formula (I) or formula (II), or a pharmaceutically acceptable salt thereof that is molar equivalent to about 50 mg to about 600 mg of Compound 1. In some embodiments, the compositions comprise a compound of formula (I) or formula (II), or a pharmaceutically acceptable salt thereof that is molar equivalent to about 50 mg to about 400 mg of Compound 1. In some embodiments, the compositions comprise a compound of formula (I) or formula (II), or a pharmaceutically acceptable salt thereof that is molar equivalent to about 50 mg to about 200 mg of Compound 1. In some embodiments, the compositions comprise a compound of formula (I) or formula (II), or a pharmaceutically acceptable salt thereof that is molar equivalent to about 50 mg to about 150 mg of Compound 1.

In some embodiments, the compositions comprise a compound of formula (I) or formula (II), or a pharmaceutically acceptable salt thereof that is molar equivalent to about 50 mg, about 60 mg, about 70 mg, about 80 mg, about 90 mg, about 100 mg, about 110 mg, about 120 mg, about 130 mg, about 140 mg, or about 150 mg of Compound 1. In some embodiments, the compositions comprise a compound of formula (I) or formula (II), or a pharmaceutically acceptable salt thereof that is molar equivalent to about 60 mg or about 120 mg of Compound 1.

In some embodiments, the compositions comprising a compound of formula (I) or formula (II), or a pharmaceutically acceptable salt thereof, comprise a pharmaceutically acceptable vehicle or carrier.

In some embodiments, the composition is stable at 25° C./60% RH for at least one week. In some embodiments, the composition is stable when stored at 25° C./60% RH for at least about 6 months. In some embodiments, the composition is stable at 25° C./60% RH for at least about 12 months. In some embodiments, the composition is stable at 25° C./60% RH for at least about one week, at least about two weeks, at least about three weeks, at least about four weeks, at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about 18 months, at least about 24 months, at least about 30 months, or at least about 36 months.

In some embodiments, the composition is stable at 40° C./75% RH for at least about one week. In some embodiments, the composition is stable at 40° C./75% RH for at least about 6 months. In some embodiments, the composition is stable at 40° C./75% RH for at least about one week, at least about two weeks, at least about three weeks, at least about four weeks, at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months. In some embodiments, the composition is stable at 40° C./75% RH for at least about 36 months. In some embodiments, the composition is stored in an open container under stability conditions.

In some embodiments, the composition is stable to light exposure for at least about 6 months. In some embodiments, the composition is stable to visible light exposure for at least about 6 months.

In some embodiments, the composition is an ophthalmic solution that is suitable for ocular administration or ophthalmic use. In some embodiments, the ophthalmic solution is suitable for topical, subconjunctival, intravitreal, retrobulbar, intracameral or systemic administration.

In some embodiments, the composition is an ophthalmic solution that is suitable for intravitreal administration and further comprises α,α-trehalose dihydrate or polysorbate 20. In some embodiments, the composition is an ophthalmic solution that is suitable for intravitreal administration and further comprises water for injection. In some embodiments, the composition is an ophthalmic solution that is suitable for intravitreal administration and further comprises a buffer.

In some embodiments, the compositions comprise a Compound 1 salt, a Compound 1 ester or pharmaceutically acceptable salt thereof, or a compound of formula (I) or formula (II), or a pharmaceutically acceptable salt thereof. In some embodiments, the composition comprises a Compound 1 calcium salt, a Compound 1 L-arginine salt, a Compound 1 L-phenylalanine salt, a Compound 1 L-histidine salt, or a compound of formula (I) or formula (II), or a pharmaceutically acceptable salt thereof.

In some embodiments, the compositions comprise a Compound 1 calcium salt obtainable according to the method of Example 1. In some embodiments, the compositions comprise a Compound 1 calcium salt obtainable according to the method of Example 2. In some embodiments, the compositions comprise a Compound 1 calcium salt obtainable according to the method of Example 3. In some embodiments, the compositions comprise a Compound 1 L-arginine salt obtainable according to the method of Example 4, Procedure A. In some embodiments, the compositions comprise a Compound 1 L-arginine salt obtainable according to the method of Example 4, Procedure B.

In some embodiments, the compositions comprising a compound of formula (I) or formula (II), or a pharmaceutically acceptable salt thereof are suitable for topical, subconjunctival, intravitreal, retrobulbar, intracameral or systemic administration. In some embodiments, the composition comprising a compound of formula (I) or formula (II), or a pharmaceutically acceptable salt thereof is suitable for intravitreal administration.

In some embodiments, the compositions comprising a compound of formula (I) or formula (II), or a pharmaceutically acceptable salt thereof is suitable for ocular administration or ophthalmic use. In some embodiments, the composition is an ophthalmic solution. In some embodiments, the ophthalmic solution is suitable for topical, subconjunctival, intravitreal, retrobulbar, intracameral or systemic administration. In some embodiments, the composition is an ophthalmic solution, or the composition is coated on or incorporated in an ophthalmic drug delivery device.

In some embodiments, the pharmaceutically acceptable carrier or vehicle is a stabilizer, binder, filler, diluent, disintegrant, wetting agent, lubricant, glidant, coloring agent, dye-migration inhibitor, sweetening agent, flavoring agent, viscosity modifying agent, pH adjusting agent, buffer, osmotic agent, chelating agent, surfactants, or co-solvent. In some embodiments, the pharmaceutically acceptable carrier or vehicle is a binder, diluent, disintegrant, and/or lubricant.

In some embodiments, a diluent is sugar, mannitol, lactose, lactose monohydrate, cellulose, microcrystalline cellulose, silicified microcrystalline cellulose, microfine cellulose, or starch. In some embodiments, starch is corn starch, potato starch, wheat starch, rice starch, partially pregelatinized starch, or perforated starch. In some embodiments, a diluent is lactose monohydrate, microcrystalline cellulose, dicalcium phosphate dihydrate, calcium carbonate, or partially pregelatinized maize starch. In some embodiments, microcrystalline cellulose has an average particle size from about 50 μm to about 200 μm. In some embodiments, microcrystalline cellulose has an average particle size of about 50 μm or about 100 μm.

In some embodiments, a disintegrant is carboxymethylcellulose, starch, pre-gelatinized starch, partially pre-gelatinized starch, crospovidone, sodium starch glycolate, or hydroxypropyl cellulose. In some embodiments, a disintegrant is carboxymethylcellulose sodium. In some embodiments, a disintegrant is low-substituted hydroxypropyl cellulose.

In some embodiments, a binder is methylcellulose, hydroxypropyl cellulose, hypromellose (hydroxypropyl methylcellulose), ethyl cellulose, povidone (polyvinylpyrrolidone), polyvinyl alcohol, powdered acacia, gelatin, or pullulan. In some embodiments, methylcellulose has a viscosity of about 25 cP.

In some embodiments, a glidant is talc.

In some embodiments, a lubricant is magnesium stearate, calcium stearate, talc, or sodium stearyl fumarate.

In some embodiments, a viscosity modifying agent is polyvinyl alcohol, poloxamers, hyaluronic acid, carbomers, and polysaccharides, that is, cellulose derivatives, gellan gum, or xanthan gum.

In some embodiments, the compositions comprise lactose monohydrate, microcrystalline cellulose, starch, carboxymethylcellulose sodium, methylcellulose, and/or magnesium stearate. In some embodiments, starch is partially pregelatinized maize starch.

In some embodiments, the pharmaceutically acceptable carrier or vehicle is sterile water, sterile buffer solution, or sterile saline.

In some embodiments, the pharmaceutically acceptable carrier or vehicle comprises or is mannitol or sodium acetate.

In some embodiments, the compositions comprise a preservative. In some embodiments, the preservative is benzalkonium chloride, cetrimide, polyquaternium-1, thimerosal, sodium perborate, stabilized oxychloro complex, stabilized chlorite peroxide, chlorhexidine, chlorobutanol, phenylethanol or methylparaben.

In some embodiments, the compositions do not comprise a preservative. In some embodiments, the compositions are preservative free.

In some embodiments, the compositions of the invention are in the form of a tablet. In some embodiments, the tablet comprises a coating. In some embodiments, the coating is a film coating.

In some embodiments, the compositions of the invention are in the form of a tablet having tablet hardness in the range of about 5 kp to about 15 kp. In some embodiments, the tablet hardness is about 5 kp, about 6 kp, about 7 kp, about 8 kp, about 9 kp, about 10 kp, about 11 kp, about 12 kp, about 13 kp, about 14 kp, or about 15 kp. In some embodiments, the tablet hardness is about 6 kp to about 12 kp. In some embodiments, the tablet hardness is about 8 kp to about 14 kp.

In some embodiments, the compositions of the invention are in the form of a tablet having tablet thickness in the range of about 3.0 mm to about 7.0 mm. In some embodiments, the tablet thickness is about 3.0 mm, about 3.5 mm, about 4.0 mm, about 4.5 mm, about 5.0 mm, about 5.5 mm, about 6.0 mm, about 6.5 mm, or about 7.0 mm. In some embodiments, the tablet hardness is about 4.0 mm to about 4.3 mm. In some embodiments, the tablet thickness is about 4.0 mm, about 4.1 mm, about 4.2 mm, or about 4.3 mm. In some embodiments, the tablet hardness is about 4.8 mm to about 5.1 mm. In some embodiments, the tablet thickness is about 4.8 mm, about 4.9 mm, about 5.0 mm, or about 5.1 mm.

In some embodiments, the compositions of the invention are in the form of a tablet having friability (% weight loss) of less than about 1%. In some embodiments, the tablet's friability is less than about 0.9%. In some embodiments, the tablet's friability is less than about 0.8%.

In some embodiments, the compositions of the invention are in the form of a tablet and the tablet has a target weight, wherein the weight variation of the tablet is ±10% of the target weight of the tablet.

In some embodiments, the compositions of the invention are in the form of a tablet, wherein an average dissolution of the compound of the invention from the tablet at 15 minutes in phosphate buffer having pH 6.8 at 37° C. is about 4% to about 10% by weight of the total amount of the compound of the invention in the tablet. In some embodiments, the average dissolution of the compound of the invention from the tablet at 15 minutes in phosphate buffer having pH 6.8 at 37° C. is about 5% to about 7% by weight of the total amount of the compound of the invention in the tablet. In some embodiments, the average dissolution of the compound of the invention from the tablet at 15 minutes in phosphate buffer having pH 6.8 at 37° C. is about 6% by weight of the total amount of the compound of the invention in the tablet. In some embodiments, the dissolution is measuring using USP Apparatus 2 (paddles) set at 100 rpm. In some embodiments, the dissolution of the compound of the invention is analyzed by HPLC based on Compound 1.

In some embodiments, the compositions of the invention are in the form of a tablet, wherein an average dissolution of the compound of the invention from the tablet at 30 minutes in phosphate buffer having pH 6.8 at 37° C. is about 10% to about 25% by weight of the total amount of the compound of the invention in the tablet. In some embodiments, the average dissolution of the compound of the invention from the tablet at 30 minutes in phosphate buffer having pH 6.8 at 37° C. is about 10% to about 20% by weight of the total amount of the compound of the invention in the tablet. In some embodiments, the average dissolution of the compound of the invention from the tablet at 30 minutes in phosphate buffer having pH 6.8 at 37° C. is about 15% by weight of the total amount of the compound of the invention in the tablet. In some embodiments, the dissolution is measuring using USP Apparatus 2 (paddles) set at 100 rpm. In some embodiments, the dissolution of the compound of the invention is analyzed by HPLC based on Compound 1.

In some embodiments, the compositions of the invention are in the form of a tablet, wherein an average dissolution of the compound of the invention from the tablet at 45 minutes in phosphate buffer having pH 6.8 at 37° C. is about 15% to about 35% by weight of the total amount of the compound of the invention in the tablet. In some embodiments, the average dissolution of the compound of the invention from the tablet at 45 minutes in phosphate buffer having pH 6.8 at 37° C. is about 20% to about 30% by weight of the total amount of the compound of the invention in the tablet. In some embodiments, the average dissolution of the compound of the invention from the tablet at 45 minutes in phosphate buffer having pH 6.8 at 37° C. is about 24% by weight of the total amount of the compound of the invention in the tablet. In some embodiments, the dissolution is measuring using USP Apparatus 2 (paddles) set at 100 rpm. In some embodiments, the dissolution of the compound of the invention is analyzed by HPLC based on Compound 1.

In some embodiments, the compositions of the invention are in the form of a tablet, wherein an average dissolution of the compound of the invention from the tablet at 60 minutes in phosphate buffer having pH 6.8 at 37° C. is about 23% to about 50% by weight of the total amount of the compound of the invention in the tablet. In some embodiments, the average dissolution of the compound of the invention from the tablet at 60 minutes in phosphate buffer having pH 6.8 at 37° C. is about 30% to about 40% by weight of the total amount of the compound of the invention in the tablet. In some embodiments, the average dissolution of the compound of the invention from the tablet at 60 minutes in phosphate buffer having pH 6.8 at 37° C. is about 35% by weight of the total amount of the compound of the invention in the tablet. In some embodiments, the dissolution is measuring using USP Apparatus 2 (paddles) set at 100 rpm. In some embodiments, the dissolution of the compound of the invention is analyzed by HPLC based on Compound 1.

In some embodiments, the compositions of the invention are in the form of a tablet, wherein an average dissolution of the compound of the invention from the tablet at 90 minutes in phosphate buffer having pH 6.8 at 37° C. is about 40% to about 75% by weight of the total amount of the compound of the invention in the tablet. In some embodiments, the average dissolution of the compound of the invention from the tablet at 90 minutes in phosphate buffer having pH 6.8 at 37° C. is about 50% to about 65% by weight of the total amount of the compound of the invention in the tablet. In some embodiments, the average dissolution of the compound of the invention from the tablet at 90 minutes in phosphate buffer having pH 6.8 at 37° C. is about 57% by weight of the total amount of the compound of the invention in the tablet. In some embodiments, the dissolution is measuring using USP Apparatus 2 (paddles) set at 100 rpm. In some embodiments, the dissolution of the compound of the invention is analyzed by HPLC based on Compound 1.

In some embodiments, the compositions of the invention have a pH of about 4 to about 8.6. In some embodiments, the compositions have a pH of about 4, about 4.5, about 5, about 5.5, about 6, about 6.5, about 7, about 7.5, about 8, or about 8.5. In some embodiments, the compositions of the invention have a pH of about 4 to about 6. In some embodiments, the compositions of the invention have a pH of about 4.5 to about 5.3. In some embodiments, the compositions have a pH of about 4.5, about 4.6, about 4.7, about 4.8, about 4.9, about 5.0, about 5.1, about 5.2, or about 5.3. In some embodiments, the compositions of the invention have a pH of 4 to 6. In some embodiments, the compositions of the invention have a pH of 4.5 to 5.3. In some embodiments, the compositions have a pH of 4.5, 4.6, 4.7, 4.8, 4.9, 5.0, 5.1, 5.2, or 5.3.

In some embodiments, the compositions of the invention are contained in a capsule.

In some embodiments, the compositions of the invention are contained in a sealed container. In some embodiments, the sealed container further contains an inert gas. In some embodiments, the inert gas is argon or nitrogen.

EXAMPLES

General Procedures: Unless otherwise noted, X-ray powder diffraction (XRPD) analysis was carried out using a Bruker D8 Discover diffractometer with DAVINCI configuration, in transmission mode (scan type: TwoTheta or Offset Coupled TwoTheta/Theta) scanning the samples (~2-3 mg) at between 1.5 and 45° 2-theta angles, and using the following measurements characteristics: acquisition time was 7.58 minutes, increment per step was 0.01°, time per step was 0.1 s, and generator voltage/generator amperage was 40 mA/40 kV to reach 1.6 kW power. The XRPD system was used in Parallel Beam Geometry (Göbel mirror) with an anode of Cu and a detector type LynxEye. Also, the XRPD system used a goniometer type Theta/Theta with a measuring circle diameter of 560 mm and vertical operating position. For transmission mode, 1 UBC collimator magnetic holder 1 mm was mounted to primary optics.

The raw XRPD data were imported in the Diffrac.EVA5.0 software and processed using the subsequent parameters: background subtraction and $K\alpha2$ stripping were performed before peak determination, and the peak search operation was performed with a threshold of 1 and a peak width of 0.153 for all Examples except Examples 2 and 3. Example 3 was performed with a threshold of 0.78 and a peak width of 0.242 (or 0.153). All resulting peaks with relative intensity greater than or equal to 2% were considered.

The XRPD data of Example 2 were obtained using a Bruker AXS with D2 Phaser 2nd Gen configuration (Part Number: A26X1-A2B0B1C) in reflection mode (scan type: Coupled TwoTheta/Theta) scanning the samples at between 3 and 40° 2-theta angles, and using the following measurements characteristics: increment per step was 0.02°, time per step was 0.3 s, and generator voltage/generator amperage was 10 mA/30 kV to reach 0.3 kW power, detector type LynxEye A17-B60 and a goniometer type Theta/Theta. The XRPD data were collected using DIFFRAC.MEASUREMENT 8.6.3.0 software and processed with DIFFRAC.EVA 6.0.0.8 software.

Compound 1 can be obtained according to U.S. Pat. No. 5,210,239.

Example 1. Synthesis of Compound 1 Calcium Salt

About 20 g of Compound 1 (1 eq.) was weighed and added to a 1 L glass reactor and mixed at room temperature with $H_2O$:MeOH (1:1 v/v) to provide a fine suspension having a concentration of 36.3 g of Compound 1/L of H₂O:MeOH (1:1 v/v). The suspension was allowed to stir for 30 minutes with a mechanical stirrer type OS-20 with a rod and PTFE propeller at 300 rpm. Calcium hydroxide (95%; 2.0953 g; 0.5 eq.) was added, and the resultant mixture was allowed to stir at 500 rpm at room temperature for 2 hours. After 2 hours, the resultant precipitate was vacuum filtered, washed with 400 mL of H₂O:MeOH (1:1 v/v). The washed precipitate was dried in a fume hood at atmospheric pressure at 25° C. for about 45 hours to provide a Compound 1 calcium salt as a light orange solid (89.06% yield).

Purity of the Compound 1 calcium salt was determined by HPLC chromatography using an Agilent 1260 Infinity HPLC device, at 30° C. and a HiChrom C18 column (4.6×100 mm, 3.5 µm). The HPLC device was coupled with a UV-Vis Diode Array Detector (HPLC-DAD). Analyses were run with a gradient method (as described in Table below) using 0.1% formic acid in purified MilliQ water (mobile phase A) and 0.1% formic acid in acetonitrile HPLC grade (mobile phase B). A flow rate was 1 mL/min and an injection volume was 5 µL. UV detection was run at 236 nm and 266 nm. The sample was dissolved into MilliQ pure water. Purity of Compound 1 calcium salt determined by HPLC at 236 nm was 99.7% and at 266 nm was 99.8%.

| Time (minutes) | % (v/v) Mobile Phase A | % (v/v) Mobile Phase B |
| --- | --- | --- |
| 0.0 | 50 | 50 |
| 3.0 | 50 | 50 |
| 10.0 | 10 | 90 |
| 13.0 | 10 | 90 |
| 15.0 | 50 | 50 |

The Compound 1 calcium salt was analyzed by XRPD, and thermo-gravimetric (TG)/differential scanning calorimetric (DSC).

FIG. 1A shows an XRPD diffractogram (background subtracted) of the Compound 1 calcium salt obtained as described in this Example, and Table 1 lists XRPD peaks represented in FIG. 1A.

TABLE 1

| XRPD Data for Compound 1 calcium salt from this Example | | | |
| --- | --- | --- | --- |
| 2-theta Angle (°) | d Value (Å) | Net Intensity (Counts) | Rel. Intensity (%) |
| 4.12 | 21.46 | 563.62 | 95.22 |
| 5.35 | 16.50 | 591.88 | 100.00 |
| 5.76 | 15.33 | 162.75 | 27.50 |
| 6.37 | 13.86 | 218.93 | 36.99 |
| 8.29 | 10.66 | 34.36 | 5.81 |
| 9.23 | 9.57 | 21.57 | 3.64 |
| 9.63 | 9.18 | 37.84 | 6.39 |
| 10.80 | 8.19 | 56.31 | 9.51 |
| 11.44 | 7.73 | 73.04 | 12.34 |
| 11.99 | 7.38 | 86.61 | 14.63 |
| 12.31 | 7.19 | 123.50 | 20.87 |
| 12.81 | 6.90 | 76.07 | 12.85 |
| 13.12 | 6.74 | 44.24 | 7.47 |
| 13.77 | 6.43 | 138.15 | 23.34 |
| 14.16 | 6.25 | 110.33 | 18.64 |
| 16.49 | 5.37 | 26.36 | 4.45 |
| 16.57 | 5.35 | 33.45 | 5.65 |
| 17.16 | 5.16 | 37.73 | 6.37 |
| 17.61 | 5.03 | 50.16 | 8.47 |
| 20.35 | 4.36 | 39.70 | 6.71 |

TABLE 1-continued

| XRPD Data for Compound 1 calcium salt from this Example | | | |
| --- | --- | --- | --- |
| 2-theta Angle (°) | d Value (Å) | Net Intensity (Counts) | Rel. Intensity (%) |
| 20.92 | 4.24 | 57.83 | 9.77 |
| 21.89 | 4.06 | 39.48 | 6.67 |
| 23.71 | 3.75 | 44.47 | 7.51 |
| 26.33 | 3.38 | 29.20 | 4.93 |

TG/DSC analysis: A sample of the Compound 1 calcium salt (about 5.3 mg) obtained according to this Example was weighed into an open aluminum pan, loaded into a simultaneous Setaram LABSYS EVO thermo-gravimetric/differential scanning calorimeter (TG-DTA/DSC) and maintained at 30° C. for 15 minutes. The sample was then heated from 30° C. to 550° C., during which time a change in sample weight was recorded along with any differential thermal events. Nitrogen was used as a purge gas, at a flow rate of 180 cm³/min. Prior to the analysis, the instrument mass loss and temperature were calibrated using copper sulfate pentahydrate and reference standards (lead and indium), respectively. The sample analysis was performed using CALISTO software, where the corresponding mass loss and temperatures of thermal events were quoted as the onset temperature, measured according to the manufacturer's specifications. The analysis was carried out with a heating rate of 10° C./minute and the background was subtracted before further processing.

The TG/DSC analysis of the Compound 1 calcium salt obtained according to this Example showed one small endothermic event between 50° C. and 89° C. (peak maximum at about 82° C.) and one exothermic event starting at about 208° C. (peak maximum at about 213) ° C. (FIG. 1B). A mass loss of about 5% was observed on the TG curve, corresponding to the endothermic event. Based on the TG/DSC data, the Compound 1 calcium salt obtained according to this Example is a monohydrate.

Compound 1 calcium salt obtained generally according to this method was further analyzed by FT-IR, FT-Raman, dynamic vapor sorption (DVS), and 1H NMR.

An FT-IR spectrum (FIGS. 1C and 1D) of the Compound 1 calcium salt was recorded at between 3500 and 50 cm-1 showing the following significant bands, expressed in wavenumbers (cm⁻¹): 2924 (m) and 2853 (m) specific to asymmetric —CH₂—, symmetric —CH₃ and —CH₂— stretching vibrations; 1636 (st) characteristic to —C═O stretching and some ═C—H stretching vibrations; 1603 (st) specific to —C═C— stretching and —C—C— skeletal vibrations; 1556 (st) also specific to —C—O— vibrations (e.g. in the —COOR groups) or aromatic —C═C— stretching vibrations; 1418 (st) characteristic for —C—C— stretch (in-ring) aromatics or —C—H bending vibrations; 1298 (m), 1261 (st), 1203 (st) and 1157 (m) specific to —C—O or —C(O)—O stretching vibrations; 1094 (m), 997 (m), 951 (w), 787 (w), 739 (m) and 636 (w) characteristic for ═C—H out-of-plane bending or —C—C— bending vibrations. The intensities of the absorption bands are indicated as follows: (w)=weak; (m)=medium; and (st)=strong intensities.

An FT-Raman spectrum (FIG. 1E) of the Compound 1 calcium salt was recorded at between 4000 and 150 cm⁻¹ showing the following significant bands, expressed in wavenumbers (cm⁻¹): 2927 (m) and 2858 (m) assigned to —CH₂ and —CH₃ vibrations; 1652 (st) assigned to —C═O group, 1600 (m) attributed to —C═C— vibrations; 1440 (m), 1384 (m), 1337 (st) and 1303 (m) attributed to ring deformation and —C—O— vibrations; 957 (w), 874 (w), 499 (m), 443 (m) and 344 (w) assigned to —C—C— vibrations and ring breathing. The intensities of the absorption bands are indicated as follows: (w)=weak; (m)=medium; and (st)=strong intensities. The error margin for all absorption bands of FT-Raman is ±2 cm$^{-1}$.

DVS Analysis: Compound 1 calcium salt had a water content of 0.39% and was equilibrated to 0 before starting the analysis. DVS analysis of the Compound 1 calcium salt (FIG. 1F) showed that the maximum water adsorption at 82% RH was about 1.52%, while at the end of the desorption branch the Compound 1 calcium salt retained 0.19% water. The pattern of a subsequent XRPD analysis revealed the same peaks, although with slightly lower intensities, and supports that post-DVS sample of the Compound 1 calcium salt maintained the same crystalline form as the pre-DVS sample of the Compound 1 calcium salt.

A $^1$H-NMR spectrum of the Compound 1 calcium salt was obtained (FIG. 1G) and no —COOH group peak (~12 ppm) was observed. δ $^1$H (600 MHz, DMSO-d$_6$): 0.84 (3H), 1.12 (6H), 1.18 (4H), 1.23 (2H), 1.33 (2H), 1.83 (3H), 1.98 (2H), 3.88 (3H), 3.91 (3H), 6.85 (1H).

Example 2. Synthesis of Compound 1 Calcium Salt

About 75 g (0.198 mol) of Compound 1 (1 eq.) was charged to a 5 L jacketed reactor. 2025 mL (27.0 vol) of 2:1 H$_2$O:MeOH (v/v) was charged to the 5 L jacketed reactor at room temperature. The reaction mixture was agitated for 25 minutes at 25±5° C. to provide a fine suspension. Calcium hydroxide (7.3 g, 0.5 eq.) was charged to the reactor portion-wise over 25 minutes. The resultant mixture was thick but remained stirrable with some shelling observed near the top of the reactor. The shelled material was scraped down. The mixture was agitated at 25±5° C. for 2 hours and the mixture became very thick. A sample was taken to confirm formation of Compound 1 calcium salt by an XRPD analysis.

The resultant solids were collected via vacuum filtration and were washed twice with 2:1 water/methanol (900 mL, 12.0 vol). The solids were dried under vacuum until they had a water content of about 12% and dried using humidified drying. The humidified drying was performed using a vacuum oven attached to a house vacuum system with a small bleed of nitrogen that was saturated with water vapor. The water vapor-saturated nitrogen was obtained by bubbling nitrogen through water and had 100% humidity at 20±5° C. Humidified drying continued until the solids had a water content of 4-6% (Table 2) to provide Compound 1 calcium salt as an orange solid (80.41 g, 97.2% yield). Purity determined by HPLC at 262 nm was 99.9%. HPLC parameters and conditions are:

Mobile Phase A: 0.1% TFA in Water
Mobile Phase B: 0.1% TFA in Acetonitrile
Diluent: Acetonitrile and Water; 80:20 v/v
Sample Concentration: 0.7 mg/mL

| Column: | Manufacturer: | GL Sciences Inc |
| --- | --- | --- |
| | Name: | Inertsil ODS-2 |
| | Dimensions (mm): | 4.6 × 150 |
| | Particle Size (μm): | 5 |
| | Part Number: | 5020-01124 |
| Pump | Flow (mL/min): | 1.0 |
| | Run Time (min): | 40 |
| | Post time (min): | Off |

| | | Time (min) | % Mobile Phase A | % Mobile Phase B |
| --- | --- | --- | --- | --- |
| Gradient: | | 0 | 50 | 50 |
| | | 5 | 50 | 50 |
| | | 15 | 10 | 90 |
| | | 30 | 10 | 90 |
| | | 32 | 50 | 50 |
| | | 40 | 50 | 50 |

| | Detector Type | Wavelength (nm) | Bandwidth (nm) | Reference Wavelength (nm) | Reference Bandwidth (nm) |
| --- | --- | --- | --- | --- | --- |
| Detector: | Variable Wavelength (VWD) | 262 | N/A | N/A | N/A |
| | Diode Array (DAD) | 262 | 4 | Off | Off |
| | Peak Width (min): | | >0.025 | | |

| Column Compartment: | Temperature (° C.): | 30 |
| --- | --- | --- |
| Autosampler: | Injection Volume (μL): | 5 |
| | Temperature (° C.): | Off |
| | Needle Rinse: | Diluent, Flush Port 3 seconds |

The Compound 1 calcium salt was analyzed by XRPD, TGA, DSC, and ¹H NMR (FIGS. 2A-2D).

TABLE 2

Vacuum Drying Time and Water Content

| Total hours dried | Hours dried with humidified drying | Water Content by KF |
|---|---|---|
| 0 | 0 | 59.10% |
| 4 | 0 | 62.17% |
| 6 | 0 | 55.89% |
| 8 | 0 | 57.95% |
| 10 | 0 | 56.52% |
| 27 | 0 | 16.84% |
| 31 | 0 | 12.14% |
| 34* | 0 | 33.30%* |
| 34* | 0 | 21.63%* |
| 51 | 17 | 7.01% |
| 58 | 24 | 5.67% |

*Inconsistency with this time point due to solids precipitating in the system and sticking to the detector FIG. 2A shows an XRPD diffractogram of the Compound 1 calcium salt obtained by this Example, and Table 3 lists XRPD peaks represented in FIG. 2A.

TABLE 3

XRPD Data for Compound 1 Calcium Salt

| 2-theta Angle (°) | d Value (Å) | Net Intensity (Counts) | Rel. Intensity (%) |
|---|---|---|---|
| 5.060 | 17.45193 | 3343.52 | 100.0% |
| 5.269 | 16.75757 | 2233.80 | 66.8% |
| 7.947 | 11.11557 | 510.340 | 15.3% |
| 8.326 | 10.61072 | 100.391 | 3.0% |
| 10.085 | 8.76359 | 950.469 | 28.4% |
| 10.591 | 8.34620 | 146.969 | 4.4% |
| 11.481 | 7.70099 | 142.132 | 4.3% |
| 12.262 | 7.21232 | 259.658 | 7.8% |
| 12.777 | 6.92287 | 475.224 | 14.2% |
| 13.302 | 6.65079 | 437.195 | 13.1% |
| 14.610 | 6.05806 | 374.263 | 11.2% |
| 15.173 | 5.83474 | 152.680 | 4.6% |
| 17.173 | 5.15931 | 152.009 | 4.5% |
| 17.901 | 4.95104 | 425.727 | 12.7% |
| 18.536 | 4.78292 | 375.464 | 11.2% |
| 19.563 | 4.53410 | 464.238 | 13.9% |
| 20.547 | 4.31902 | 139.854 | 4.2% |
| 22.730 | 3.90898 | 249.891 | 7.5% |
| 23.764 | 3.74119 | 69.3565 | 2.1% |
| 24.555 | 3.62242 | 55.5633 | 1.7% |
| 25.704 | 3.46305 | 87.4043 | 2.6% |
| 27.127 | 3.28460 | 161.520 | 4.8% |

TGA analysis: A sample of the Compound 1 calcium salt (about 2-5 mg) obtained generally according to this Example, was weighed into an aluminum pan (70 µL), loaded into Mettler Toledo TGA 2 Star System (sampling interval: 1 s). The sample was then heated from 25° C. to 350° C. (heating rate of 10 K/min), during which time a change in sample weight was recorded. The sample analysis was performed using STAR 16.20 software.

DSC analysis: A sample of the Compound 1 calcium salt (about 3-6 mg) obtained generally according to this Example, was weighed into an aluminum pan (40 µL), loaded into Mettler Toledo DSC 1 Star System (sampling interval: 1 s). The sample was then heated from 25° C. to 350° C. (heating rate of 10° C./min), during which any differential thermal events were recorded. Nitrogen was used as a purge gas, at a flow rate of 80 cm³/min. The sample analysis was performed using STAR 16.10 software.

¹H NMR analysis: 1H NMR spectrum was obtained on Bruker Advance III HD 300 MHz NMR Spectrometer (sample size: about 8 mg/mL in DMSO-$d_6$) and analyzed with TopSpin 3.6.4 software.

Example 3. Synthesis of Compound 1 Calcium Salt (Predominantly Amorphous)

Compound 1 calcium salt as prepared generally according to Example 1 was heated at about 60° C. for 1 h at atmospheric pressure. The resultant Compound 1 calcium salt was determined to be anhydrous and predominantly (>50%) amorphous, as evidenced by the presence of only a few XRPD peaks.

FIG. 3A shows an XRPD diffractogram (background subtracted) of the anhydrous and predominantly amorphous Compound 1 calcium salt obtained when heated at about 60° C. for 1 h at atmospheric pressure, and Table 4 lists XRPD peaks represented in FIG. 3A.

TABLE 4

| 2-theta Angle (°) | d Value (Å) | Net Intensity (Counts) | Rel. Intensity (%) |
|---|---|---|---|
| 4.45 | 19.85 | 719.68 | 100.00 |
| 6.00 | 14.72 | 60.49 | 8.40 |
| 9.11 | 9.70 | 27.73 | 3.85 |

Figure 3B:
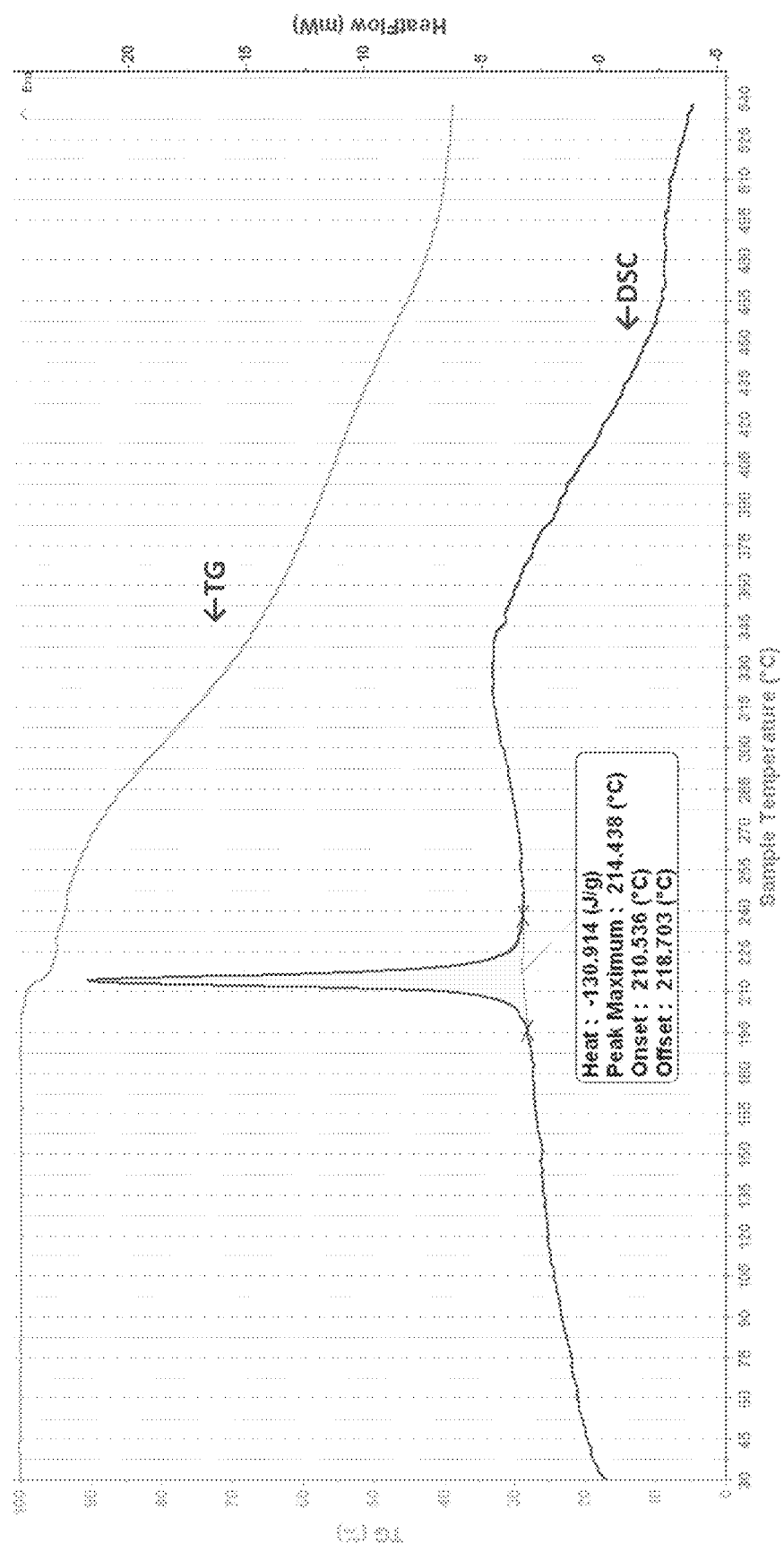
FIG. 3B shows an overlay of a TG thermogram and a DSC thermogram of the anhydrous and predominantly amorphous Compound 1 calcium salt obtained as described in Example 3.

The TG/DSC analysis of the predominantly amorphous Compound 1 calcium salt showed only one exothermic event starting at about 210° C. that was attributed to the degradation process of the salt (FIG. 3B). No mass loss was attributed to the thermal event. Based on the TG/DSC data, the predominantly amorphous Compound 1 calcium salt is anhydrous.

Hydration Experiment: Water (1.60 mL) was added to the Compound 1 calcium salt (anhydrous and predominantly amorphous) as obtained above (about 200 mg). The resultant mixture was allowed to stir at 700 rpm for 1 h. The resultant mixture was heated at about 40° C. for 2 h at atmospheric pressure then at 50° C. for 4 h at atmospheric pressure. The resultant solids showed an XRPD pattern and a TG/DSC consistent with Compound 1 calcium salt monohydrate obtained generally according to Example 1.

Example 4. Synthesis of Compound 1 L-Arginine Salts

Procedure A: About 100 mg of Compound 1 (1 eq.) was placed in a flask and admixed at room temperature with acetonitrile to provide a solution having a concentration of 100.94 mg of Compound 1/mL of acetonitrile. The solution was allowed to stir (500 rpm) for 1 h. L-Arginine (1.1 eq.) was added, and the resultant mixture was allowed to stir for 3 h at room temperature. The resultant precipitate was filtered, washed with 4 mL acetonitrile, and vacuum dried (30° C. and 22 mbar) overnight to obtain a dark yellow solid (88.81% yield).

Purity of the Compound 1 calcium salt was determined by HPLC chromatography using an Agilent 1260 Infinity HPLC device, at 30° C. and a HiChrom C18 column (4.6×100 mm, 3.5 µm). The HPLC device was coupled with a UV-Vis Diode Array Detector (HPLC-DAD). Analyses were run with a gradient method using 0.1% formic acid in purified MilliQ water (mobile phase A) and 0.1% formic acid in acetonitrile HPLC grade (mobile phase B). The gradient went from 50% phase A 3 min., switched to 10% phase A after 10 min. then held at 10% phase A for 3 min. and then returned to 50% phase A for 15 min., with a flow rate of 1 mL/min and an injection volume of 5 μL. UV detection was run at 236 nm and 266 nm. The sample was dissolved into MilliQ pure water.

HPLC purity of the Compound 1 L-arginine salt obtained by Procedure A of this Example at 236 nm was 98.9% and at 266 nm was 99.6%.

FIG. 4A shows an XRPD diffractogram (background subtracted) of Compound 1 L-arginine salt obtained as described in Procedure A, and Table 5A lists XRPD peaks represented in FIG. 4A.

TABLE 5A

XRPD Data for Compound 1 L-arginine salt

| 2-theta Angle (°) | d Value (Å) | Net Intensity (Counts) | Rel. Intensity (%) |
|---|---|---|---|
| 3.92 | 22.51 | 255.86 | 11.57 |
| 10.36 | 8.53 | 431.21 | 19.51 |
| 11.34 | 7.80 | 77.55 | 3.51 |
| 11.63 | 7.60 | 304.95 | 13.79 |
| 11.88 | 7.44 | 1208.44 | 54.67 |
| 12.48 | 7.08 | 90.80 | 4.11 |
| 13.12 | 6.74 | 752.95 | 34.06 |
| 15.34 | 5.77 | 150.98 | 6.83 |
| 15.66 | 5.65 | 50.22 | 2.27 |
| 17.28 | 5.13 | 60.06 | 2.72 |
| 18.20 | 4.87 | 103.57 | 4.68 |
| 18.41 | 4.81 | 118.80 | 5.37 |
| 18.83 | 4.71 | 58.54 | 2.65 |
| 19.29 | 4.60 | 291.43 | 13.18 |
| 19.68 | 4.51 | 1413.12 | 63.93 |
| 20.20 | 4.39 | 2210.58 | 100.00 |
| 20.80 | 4.27 | 101.86 | 4.61 |
| 21.32 | 4.16 | 148.17 | 6.70 |
| 21.72 | 4.09 | 298.90 | 13.52 |
| 22.12 | 4.02 | 187.19 | 8.47 |
| 22.72 | 3.91 | 916.46 | 41.46 |
| 22.99 | 3.87 | 180.04 | 8.14 |
| 23.48 | 3.79 | 599.49 | 27.12 |
| 23.96 | 3.71 | 214.58 | 9.71 |
| 24.02 | 3.70 | 231.86 | 10.49 |
| 24.74 | 3.60 | 232.76 | 10.53 |
| 26.32 | 3.38 | 200.12 | 9.05 |
| 26.46 | 3.37 | 161.70 | 7.31 |
| 26.71 | 3.34 | 108.01 | 4.89 |
| 27.70 | 3.22 | 116.56 | 5.27 |
| 28.53 | 3.13 | 72.08 | 3.26 |
| 29.40 | 3.04 | 177.73 | 8.04 |
| 30.99 | 2.88 | 85.14 | 3.85 |
| 30.99 | 2.88 | 82.16 | 3.72 |
| 31.58 | 2.83 | 127.11 | 5.75 |
| 32.01 | 2.79 | 155.44 | 7.03 |
| 34.28 | 2.61 | 54.60 | 2.47 |
| 36.32 | 2.47 | 52.22 | 2.36 |

Procedure B: About 20 mg of Compound 1 (1 eq.) was placed in a 2 mL vial containing acetonitrile to provide a solution having a concentration of about 101.00 mg of Compound 1/mL of acetonitrile. The resultant solution was allowed to stir (500 rpm) for 1 h. L-Arginine (1.1 eq.) was added at room temperature, and the resultant mixture was allowed to stir for 4 h at room temperature. The resultant precipitate was filtered and vacuum dried (30° C. and 21 mbar) for 4 h to obtain Compound 1 L-arginine salt as a yellow solid (yield not determined).

HPLC purity (see Procedure A for HPLC conditions) of the Compound 1 L-arginine salt obtained by Procedure B at 236 nm was 89.4% and at 266 nm was 93.0%.

FIG. 4B shows an XRPD diffractogram (background subtracted) of the Compound 1 L-arginine salt obtained as described in Procedure B, and Table 5B lists XRPD peaks represented in FIG. 4B.

TABLE 5B

XRPD Data for Compound 1 L-arginine salt

| 2-theta Angle (°) | d Value (Å) | Net Intensity (Counts) | Rel. Intensity (%) |
|---|---|---|---|
| 3.85 | 22.94 | 526.45 | 100.00 |
| 10.41 | 8.49 | 247.31 | 46.98 |
| 11.02 | 8.02 | 43.19 | 8.20 |
| 11.46 | 7.72 | 68.57 | 13.02 |
| 11.69 | 7.57 | 164.22 | 31.19 |
| 11.85 | 7.46 | 273.02 | 51.86 |
| 12.53 | 7.06 | 82.50 | 15.67 |
| 12.82 | 6.90 | 222.57 | 42.28 |
| 13.13 | 6.74 | 366.03 | 69.53 |
| 15.35 | 5.77 | 131.22 | 24.92 |
| 18.28 | 4.85 | 163.75 | 31.10 |
| 18.35 | 4.83 | 149.86 | 28.46 |
| 19.80 | 4.48 | 339.67 | 64.52 |
| 19.86 | 4.47 | 328.67 | 62.43 |
| 20.25 | 4.38 | 351.75 | 66.82 |
| 20.36 | 4.36 | 309.19 | 58.73 |
| 20.86 | 4.26 | 73.57 | 13.97 |
| 21.49 | 4.13 | 157.89 | 29.99 |
| 21.76 | 4.08 | 271.44 | 51.56 |
| 22.17 | 4.01 | 48.74 | 9.26 |
| 22.83 | 3.89 | 191.26 | 36.33 |
| 23.03 | 3.86 | 112.35 | 21.34 |
| 23.26 | 3.82 | 28.13 | 5.34 |
| 23.54 | 3.78 | 128.50 | 24.41 |
| 23.98 | 3.71 | 121.62 | 23.10 |
| 24.76 | 3.59 | 105.71 | 20.08 |
| 27.45 | 3.25 | 61.24 | 11.63 |
| 28.55 | 3.12 | 39.98 | 7.59 |
| 29.45 | 3.03 | 34.43 | 6.54 |
| 34.29 | 2.61 | 26.70 | 5.07 |

Compound 1 L-arginine salt obtained as described in Procedure A (HPLC purity at 236 nm was 98.9% and at 266 nm was 99.6%) was analyzed by TG/DSC.

The TG/DSC analysis of Compound 1 L-arginine salt obtained as described in Procedure A showed one small endothermic event between 55° C. and 66° C. (peak maximum at about 61° C.) and one exothermic event starting at about 146° C. (peak maximum at about 150° C.) (FIG. 4C). No mass loss was attributed to the first thermal event. Based on the TG/DSC data, the Compound 1 L-arginine salt obtained according to Procedure A is anhydrous.

The threshold solubility of Compound 1 L-arginine salt obtained according to Procedure A in Milli-Q® water (c=1 mg/mL concentration, 37° C., stirred for 24 hours) was determined by HPLC to be about 630 μg/mL, after 24 h at 37° C. (release efficiency >90%).

Example 5. Synthesis of Compound 1 L-Phenylalanine Salt and Compound 1 L-Histidine Salt An ethanol solution of Compound 1 (concentration of 201.60 mg/mL) was apportioned among six vials such that each vial contained about 25 mg of Compound 1 (1 eq.). Solid L-phenylalanine (1.1 eq.) or solid L-histidine (1.1 eq.) and a base or a mixture of bases (9.21 μL triethylamine, 2.64 mg NaOH, or 3.71 mg KOH) was added to each vial containing Compound 1. The resultant mixtures were allowed to stir for 4 hours at about 25-27° C. Precipitates formed and were collected.

Compound 1 L-phenylalanine salt was obtained as dark yellow solids.

Compound 1 L-histidine salt was obtained as a dark yellow solid, brown solid, or dark red solid.

Example 6. Preparation of Tablets Containing a Compound 1 Salt

Tablets containing a Compound 1 salt, such as a Compound 1 calcium salt disclosed herein, are prepared. The manufacturing process steps include pre-mixing, granulation, milling, blending, tableting, and coating.

Granulation Process: A Compound 1 salt and one or more excipients, such as a diluent, binder, disintegrant, anticaking agent, surfactant, and lubricant, are individually de-lumped and collected in a suitable tared container. The combined powders are then charged into a fluid bed granulator and sprayed with the granulating solution. After a granulating solution is applied, additional purified water is sprayed onto the fluidized powders to a visually acceptable endpoint. At this endpoint, the liquid spraying is stopped, and drying is started. Granulated powders are dried in the fluid bed until the Loss on Drying (LOD) become less than or equal to 3%.

The bulk dried granulation is milled and blended. The combined granulation is milled in preparation for the blending process. Approximately half of the granulation is added to a v-blender. One or more excipients, such as a diluent, binder, or disintegrant, are de-lumped and then added to the v-blender. The other half of the granulation is then added to v-blender, and the powders are pre-blended. A visually equivalent volume of the pre-blend is added to a container of one or more excipients, such as a lubricant, and is bag blended. This blend is de-lumped by passing through a 30-mesh screen by hand, adding to the v-blender, and blending. The completed final blend is discharged and weighed prior to the tablet compression steps.

Compression: The granulation is compressed on a press equipped with a force feeder and the appropriate round compression tooling. The final blend is added to the press and the tablet weight is established. The main compression force is then adjusted to achieve a target tablet hardness (about 8-14 kp) and thickness (about 5.0 mm). After initial startup sample testing confirms acceptable weight variation, hardness, thickness, and friability, the bulk final blends are compressed into tablet cores. The cores are collected into tared and double lined fiber drums. During the compression run, tablets are collected every 10 minutes and a composite weight of 10 tablets is recorded along with the breaking force and thickness of five tablets. From this in-process sample, 5 tablets are placed into a composite sample container for end of batch tablet physical testing.

Coating: A coating suspension is prepared, such as using an Opadry® Yellow coating and purified water. Tablets are coated to a target weight gain of about 4.0 to 5.0%.

Table 6 presents the in-process controls.

TABLE 6

In-Process Control

| Process Step | In-process test | Limits |
| --- | --- | --- |
| Granulation | Moisture (% LOD) | ≤3.0% |
| Compression | Tablet Hardness (kp) | 8-14 |
|  | Friability (% Weight Loss) | <0.8% |
|  | Weight Variation | ±10% of target wt. (430 mg) |
|  | Tablet thickness (mm) | 4.80-5.10 (target 5.0 mm) |

Example 7. Safety and Efficacy Study of Compound 1 Calcium Salt in Patients with an Ocular Disease This study is randomized, placebo-controlled, double-masked study of the safety and efficacy of orally administered Compound 1 calcium salt prepared according to any one of Examples 2-4 twice daily for 24 weeks in subjects with an ocular disease as described herein, such as moderately severe to severe non-proliferative diabetic retinopathy (NPDR) or mild proliferative diabetic retinopathy (PDR).

The study has a 1:1 randomization (placebo:the Compound 1 calcium salt). Randomization is stratified by level of disease severity.

Compound 1 calcium salt arm: 600 mg/day of Compound 1 calcium salt are taken by mouth divided as morning dose and evening dose (e.g., 360 mg every morning and 240 mg every evening).

Placebo arm: placebo tablets are identical to Compound 1 calcium salt tablets except for the absence of Compound 1 calcium salt. Five placebo tablets are taken by mouth as follows: 3 tablets every morning and 2 tablets every evening.

Study medication is taken at approximately the same time each day and may be taken with or without food. If a subject is considering discontinuing the study due to an adverse event, a dose reduction from 600 mg to 480 mg per day as an alternative can be offered (2 tablets every morning and 2 tablets every evening). The Screening Visit (Visit 1) occurs 1 to 21 days prior to Qualification/Baseline Visit (Visit 2), which occurs before dosing on Day 1. There are 3 scheduled treatment site visits: Visit 4 Week 4 (±2 days), Visit 6 Week 12 (±2 days), and Visit 9 Week 24 (±2 days). In between these visits, subjects are contacted by telephone on Visit 3 Week 1 (±2 days), Visit 5 Week 8 (±2 days), Visit 7 Week 16 (±2 days), and Visit 8 Week 20 (±2 days) for a safety assessment to include adverse events (AEs), concomitant medications, and drug compliance.

Analysis of efficacy: For the analysis of the primary efficacy endpoint, appropriate imputation techniques are performed for missing observations or for subjects requiring rescue if applicable. If the analysis using the per-protocol (PP) population shows a positive effect for Compound 1 calcium salt at the 0.05 level of significance, the primary endpoint is considered met. Confirmatory analyses may be performed using the all randomized population, with imputation performed for missing data. If warranted, confirmatory analyses with imputation for missing data or subjects requiring rescue are also performed for the secondary efficacy endpoints.

For all efficacy endpoints, baseline values are defined as the last observation prior to randomization. The primary efficacy endpoint is the difference between treatment groups in percent of subjects with a ≥2-step improvement from baseline in disease severity score, such as diabetic retinopathy severity score, in the study eye at Week 24. The primary efficacy endpoint is analyzed using a logistic regression model with treatment as factor and the baseline severity score as a covariate. The percent of subjects in each treatment group meeting the criteria, the odds ratio (OR) with 95% confidence interval (CI), and p-value are provided.

What is claimed is:

1. Compound 1 calcium salt that exhibits an X-ray powder diffraction (XRPD) pattern comprising a peak at 8.0±0.2 degrees 2-theta and a peak at 10.1±0.2 degrees 2-theta, wherein said Compound 1 calcium salt is a calcium salt of (2E)-2-[(4,5-dimethoxy-2-methyl-3,6-dioxo-1,4-cyclohexadien-1-yl)methylene]-undecanoic acid.

2. The Compound 1 calcium salt of claim 1, wherein the XRPD pattern further comprises a peak at 13.3±0.2 degrees 2-theta or a peak at 14.6 degrees 2-theta.

3. The Compound 1 calcium salt of claim 1, wherein the Compound 1 calcium salt exhibits an X-ray powder diffraction (XRPD) pattern comprising a peak at 5.1±0.2 degrees 2-theta, a peak at 8.0±0.2 degrees 2-theta, a peak at 10.1±0.2 degrees 2-theta, a peak at 13.3±0.2 degrees 2-theta, a peak at 14.6±0.2 degrees 2-theta, and a peak at 18.5±0.2 degrees 2-theta.

4. Compound 1 calcium salt that exhibits an XRPD pattern that is substantially the same as that depicted in FIG. 2A, wherein said Compound 1 calcium salt is a calcium salt of (2E)-2-[(4,5-dimethoxy-2-methyl-3,6-dioxo-1,4-cyclohexadien-1-yl)methylene]-undecanoic acid.

5. The Compound 1 calcium salt of claim 1, wherein the Compound 1 calcium salt is 95.0% pure by weight according to HPLC chromatogram, based on the HPLC chromatogram's relative peak area.

6. The Compound 1 calcium salt of claim 1, wherein the Compound 1 calcium salt is 98% pure by weight according to HPLC chromatogram, based on the HPLC chromatogram's relative peak area.

7. A composition comprising the Compound 1 calcium salt of claim 1, and a pharmaceutically acceptable carrier or excipient.

8. The Compound 1 calcium salt of claim 2, wherein the Compound 1 calcium salt is 98% pure by weight according to HPLC chromatogram, based on the HPLC chromatogram's relative peak area.

9. The Compound 1 calcium salt of claim 3, wherein the Compound 1 calcium salt is 98% pure by weight according to HPLC chromatogram, based on the HPLC chromatogram's relative peak area.

10. The Compound 1 calcium salt of claim 4, wherein the Compound 1 calcium salt is 98% pure by weight according to HPLC chromatogram, based on the HPLC chromatogram's relative peak area.

11. A composition comprising the Compound 1 calcium salt of claim 2, and a pharmaceutically acceptable carrier or excipient.

12. A composition comprising the Compound 1 calcium salt of claim 3, and a pharmaceutically acceptable carrier or excipient.

13. A composition comprising the Compound 1 calcium salt of claim 4, and a pharmaceutically acceptable carrier or excipient.

14. A composition comprising the Compound 1 calcium salt of claim 5, and a pharmaceutically acceptable carrier or excipient.

15. A composition comprising the Compound 1 calcium salt of claim 8, and a pharmaceutically acceptable carrier or excipient.

16. A composition comprising the Compound 1 calcium salt of claim 9, and a pharmaceutically acceptable carrier or excipient.

17. A composition comprising the Compound 1 calcium salt of claim 10, and a pharmaceutically acceptable carrier or excipient.

18. The Compound 1 calcium salt of claim 1, wherein the Compound 1 calcium salt is 99.9% pure by weight according to HPLC chromatogram, based on the HPLC chromatogram's relative peak area.

19. The Compound 1 calcium salt of claim 2, wherein the Compound 1 calcium salt is 99.9% pure by weight according to HPLC chromatogram, based on the HPLC chromatogram's relative peak area.

20. The Compound 1 calcium salt of claim 3, wherein the Compound 1 calcium salt is 99.9% pure by weight according to HPLC chromatogram, based on the HPLC chromatogram's relative peak area.

21. The Compound 1 calcium salt of claim 4, wherein the Compound 1 calcium salt is 99.9% pure by weight according to HPLC chromatogram, based on the HPLC chromatogram's relative peak area.

22. The Compound 1 calcium salt of claim 18, wherein the purity is determined by HPLC at 262 nm.

23. A composition comprising the Compound 1 calcium salt of claim 18, and a pharmaceutically acceptable carrier or excipient.

24. A composition comprising the Compound 1 calcium salt of claim 19, and a pharmaceutically acceptable carrier or excipient.

25. A composition comprising the Compound 1 calcium salt of claim 20, and a pharmaceutically acceptable carrier or excipient.

26. A composition comprising the Compound 1 calcium salt of claim 21, and a pharmaceutically acceptable carrier or excipient.

27. A composition comprising the Compound 1 calcium salt of claim 22, and a pharmaceutically acceptable carrier or excipient.

\* \* \* \* \*